United States Patent
Siadak et al.

(10) Patent No.: US 8,466,262 B2
(45) Date of Patent: *Jun. 18, 2013

(54) VARIABLE REGION SEQUENCES OF IL-31 MONOCLONAL ANTIBODIES AND METHODS OF USE

(75) Inventors: Anthony W. Siadak, Kent, WA (US); Janine M. Bilsborough, Seattle, WA (US); Shirley A. Rene, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 248 days.

This patent is subject to a terminal disclaimer.

(21) Appl. No.: 12/439,079

(22) PCT Filed: Sep. 4, 2007

(86) PCT No.: PCT/US2007/077555
§ 371 (c)(1),
(2), (4) Date: Aug. 19, 2009

(87) PCT Pub. No.: WO2008/028192
PCT Pub. Date: Mar. 6, 2008

(65) Prior Publication Data
US 2010/0008909 A1    Jan. 14, 2010

(51) Int. Cl.
| | |
|---|---|
| C07K 16/00 | (2006.01) |
| C12P 21/08 | (2006.01) |
| A61K 39/00 | (2006.01) |
| A61K 39/395 | (2006.01) |

(52) U.S. Cl.
USPC ............... 530/388.1; 530/388.23; 424/133.1; 424/141.1

(58) Field of Classification Search
None
See application file for complete search history.

(56) References Cited

U.S. PATENT DOCUMENTS

| | | | |
|---|---|---|---|
| 7,064,186 B2 * | 6/2006 | Sprecher et al. | 530/351 |
| 7,514,077 B2 | 4/2009 | Yao et al. | |
| 7,531,636 B2 | 5/2009 | Sprecher et al. | |
| 7,531,637 B2 | 5/2009 | Siadak et al. | |
| 7,638,126 B2 | 12/2009 | Yao et al. | |
| 7,939,068 B2 | 5/2011 | Yao et al. | |
| 7,943,132 B2 | 5/2011 | Yao et al. | |
| 8,013,124 B2 | 9/2011 | Sprecher et al. | |
| 8,017,122 B2 | 9/2011 | Siadak et al. | |
| 8,101,183 B2 | 1/2012 | Siadak et al. | |
| 8,105,590 B2 | 1/2012 | Yao et al. | |
| 8,105,591 B2 | 1/2012 | Yao et al. | |
| 2003/0224487 A1 * | 12/2003 | Sprecher et al. | 435/69.5 |
| 2006/0188500 A1 | 8/2006 | Leung et al. | |
| 2009/0149635 A1 | 6/2009 | Sprecher et al. | |
| 2009/0208494 A1 | 8/2009 | Bondensgaard et al. | |
| 2009/0252732 A1 | 10/2009 | Siadak et al. | |
| 2011/0293514 A1 | 12/2011 | Siadak et al. | |
| 2012/0107310 A1 | 5/2012 | Yao et al. | |
| 2012/0207757 A1 | 8/2012 | Yao et al. | |

FOREIGN PATENT DOCUMENTS

| | | |
|---|---|---|
| WO | WO 03/060090 | 7/2003 |
| WO | WO 2006/122079 | 11/2006 |

OTHER PUBLICATIONS

Dillon, Sprecher, Hammond, Bilsborough, Rosenfeld-Franklin, Presnell, Haugen, Maurer, Harder, Johnston, Bort, Mudri, Kuikper, Bokowski, Shea, Dong, Dasovich, Grant, Lockwood, Levin, Le Ciel, Waggie, Day, et al. Interleukin 31, a cytokine produced by activated T cells, induces dermatitis in mice. Nature Immunology, 2004. vol. 5, pp. 752-760.*

"Monoclonal Anti-human IL-31 Antibody", Apr. 18, 2006, R&D Systems, Inc., XP002461764, ISBN: 1-800-343-7475, retrieved from the Internet: URL: http://www.rndsystems.com/pdf/MAB2824.pdf> the whole document.

Presta, L.G. et al., "Engineering of therapeutic antibodies to minimize immunogenicity and optimize function", Advanced Drug Delivery Reviews, vol. 58, pp. 640-656 (2006).

U.S. Appl. No. 13/359,049, filed Jan. 26, 2012, Sprecher et al.
U.S. Appl. No. 13/329,392, filed Dec. 19, 2012, Siadak et al.

* cited by examiner

*Primary Examiner* — Elizabeth C Kemmerer
(74) *Attorney, Agent, or Firm* — Brian J. Walsh; Robyn Adams

(57) ABSTRACT

Novel compositions derived from antigen-binding sites of immunoglobulins having affinity for IL-31 are provided. The compositions exhibit immunological binding properties of antibody molecules capable of binding specifically to a human IL-31. CDR regions derived from same or different immunoglobulin moieties are provided. Also provided are single chain polypeptides wherein VH and VL domains are attached. The sFv molecules can include ancillary polypeptide moieties which can be bioactive, or which provide a site of attachment for other useful moieties. The compositions are useful in specific binding assays, affinity purification schemes, drug or toxin targeting, imaging, and genetic or immunological therapeutics for inflammatory diseases. The invention thus provides novel polypeptides, the DNAs encoding those polypeptides, expression cassettes comprising those DNAs, and methods of inducing the production of the polypeptides. The invention further provides the amino acid sequences of the variable regions of the monoclonal antibodies and use of these monoclonal antibody or antibody fragment in conjunction with an human IgG4 Fc molecule.

9 Claims, 4 Drawing Sheets

Figure 1: Sequences numbered according to Kabat. The CDRs are indicated by underline.

VL

```
NAME          1          10         20         30    35   40         50         60         70         80         90         100
292.12.3.1    DIQMTQSPASLSASVGETVTITCRASG-----NIHNYLAWYQQKPGKSPQLLVYNAKTLADGVPSRFSGSRSETQYSLKINSLQPEDFGSYYCQHFWSTPWTFGGGTKLEIK  (SEQ ID NO:8)
292.84.1.6    DIQMTQSPASLSASVGETVTITCRASG-----NIHNYLAWYQQKQGRSPQLLVYNAKTLADGVPSRFSGSRSETQYSLKINSLQPEDFGSYYCQHFWSTPWTFGGGTKLEIK  (SEQ ID NO:8)
292.63.5.3    DIVMTQSPSSLDMSEGQKVTMICKSSQSLLNGSNQKNYLAWYQQKPGQSPKLLVSFASTRDSGVPDRFIGSGSGTDFTLTITNVQAEDLADYFCQQHYDTPYTFGGGTKLEIR  (SEQ ID NO:10)
294.144.3.5   ENVLTQSPAIMSASPGERVTMTCSASS------SVSYMHWYQQKSSNSPKLWIYDTTKLASGVPGRFSGSGSGNSYSLTISSMEAEDVATYFCFQGSEHPLTFGGGTLEIK    (SEQ ID NO:86)
```

VH

```
Name          1          10         20         30  36  40         50         65   70         80         90         103   110
292.12.3.1    QVQLQQSGAELARPGASVNLSCKASGYTLTRYWMQWVKQRPGQGLEWIGAIYPGDGDTRYSQKFKGKATLTADKSSSTAYMQLNNLASEDSAVYYCAFPDGYYAAPYGMDYWGQGTSVTVSS     (SEQ ID NO:9)
292.84.1.6    QVQLQQSGAELARPGASVNLSCKASGYTLTRYWMQWVKQRPGQGLEWIGTIYPGDGDTRYSQKFKGKASLTADKSNTAYMQLNNLASEDSAVYFCAFPDGYYAAPYGMDYWGQGTSVTVSS      (SEQ ID NO:9)
292.63.5.3    EVQLVESGGDLVKPGGSLKLSCAASGFTFSTFIMSWVRQSPEKRLEWVATINSGGYYTFHPDSVKGRFTISRDNAKNTLYLQMSLRSEDTAIYYCARQEGWSSA--YFSYWGQGTLVTVSA       (SEQ ID NO:87)
294.144.3.5   QVQLQQSGPELMKPGASVKISCKATGYTFSTYWIEWIKQRPGHGLEWIGEILPGRGTTNYNAKFQGKATFTAETSSNTAYMQLSSLTSEDSAVYYCTTESKL----GDDDYWGQSTTLTVSS      (SEQ ID NO:88)
```

Figure 2: Sequences numbered according to Kabat. The CDRs are indicated by underline

VL

| NAME | | | | | | | | | | |
|---|---|---|---|---|---|---|---|---|---|---|
| | 1 | 10 | 20 | 35 40 | 50 | 60 | 70 | 80 | 90 100 | |
| 292.12.3.1 | DIQMTQSPASLSASVGETVTITCRASGNIHNYLAWYQQKQGKSPQLLVYNAKTLADGVPSRFSGSSRSETQYSLKINSLQPEDFGSYYCQHFWSTPWTFGGGTKLEIK | | | | | | | | | (SEQ ID NO:8) |
| 292.84.1.6 | DIQMTQSPASLSASVGETVTITCRASGNIHNYLAWYQQKQGRSPQLLVYNAKTLADGVPSRFSGSSRSETQYSLKINSLQPEDFGSYYCQHFWSTPWTFGGGTKLEIK | | | | | | | | | (SEQ ID NO:8) |

VH

| Name | | | | | | | | | | |
|---|---|---|---|---|---|---|---|---|---|---|
| | 1 | 10 | 20 | 30 | 36 40 | 50 | 65 70 | 80 | 90 | 103 110 |
| 292.12.3.1 | QVQLQQSGAELARPGASVNLSCKASGYTLTRYWMQWVKQRPGQGLEWIGAIYPGDGDTRYSQKFKGKATLTADKSSTAYMQLNNLASEDSAVYYCAFPDGYYAAPYGMDYWGQGTSVTVSS | | | | | | | | | (SEQ ID NO:9) |
| 292.84.1.6 | QVQLQQSGAELARPGASVNLSCKASGYTLTRYWMQWVKQRPGQGLEWIGTIYPGDGDTRYSQKFKGKASLTADKSSNTAYMQLNNLASEDSAVYFCAFPDGYYAAPYGMDYWGQGTSVTVSS | | | | | | | | | (SEQ ID NO:9) |

Figure 3: Alignment of VL and VH predicted amino acid sequences from mouse anti-human IL31 hybridomas from Bin 1A. Residues are numbered and CDRs are defined according to Kabat. The CDRs are underlined. N-linked carbohydrate motifs are highlighted in grey. An "." indicates identity with sequence above.

| VL | | | | | | | | | | | |
|---|---|---|---|---|---|---|---|---|---|---|---|
| | 1 | 10 | 20 | 35 | 40 | 50 | 60 | 70 | 80 | 90 | 100 |
| ABPC48 | DIVMTQSPSSLAMSVGQKVTMSCKSSQSLLSSSNQKNYLAWYQQKPGQSPKLLVYFASTRESGXPDRFIGSGSGTDFTLTISSVQAEDLALYYCQQHYSTP | | | | | | | | | | (SEQ ID NO:89) |
| 292.63.5.3 | ..........D.E..............I..N........................S...D.V..............TN.....D.F....D.YTFGGGTKLEIR | | | | | | | | | | (SEQ ID NO:10) |
| 292.39.5.3 | ............................I.N............................G...V................N......D.F...F........... | | | | | | | | | | (SEQ ID NO:14) |
| 292.51.5.2 | ............................I..............H....S.T.........V.................TNM....D.F...D........... | | | | | | | | | | (SEQ ID NO:16) |
| 292.64.6.5.5 | ............................I.N............R.I...........G..V.................N......D.F...F........... | | | | | | | | | | (SEQ ID NO:18) |
| 292.105.4.1 | ............................I.N............R..............G..V.................N......D.F...F........... | | | | | | | | | | (SEQ ID NO:20) |
| 292.109.4.4 | ............................I.N............R..............G..V.....M...........N......D.F...F........... | | | | | | | | | | (SEQ ID NO:22) |
| 292.118.6.4 | ............................I.N..........R................G..V.................N......D.F...F........... | | | | | | | | | | (SEQ ID NO:24) |
| | | | CDR 1 | | | CDR 2 | | | | CDR 3 | |

| VH | | | | | | | | | | |
|---|---|---|---|---|---|---|---|---|---|---|
| | 1 | 10 | 20 | 30 | 36 40 | 50 | 65 70 | 80 | 90 | 103 110 |
| Vh718 | EVKLVESGGGLVKPGGSLKLSCAASGFTFSSYTMSWVRQSPEKRLEWVATISSGGSYTYYPDSVKGRFTISRDNAKNTLYLQMSSLKSEDTAMYYCTR | | | | | | | | | (SEQ ID NO:90) |
| 292.63.5.3 | ..Q.........D.................TFI........N..Y.FH............................R....I..A.QEGWSSAYFSYWGQGTLVTVSA | | | | | | | | | (SEQ ID NO:11) |
| 292.39.5.3 | ..Q.........D.................T.I........N..Y.L......V......................R....F.A........W.A. | | | | | | | | | (SEQ ID NO:15) |
| 292.51.5.2 | ..Q.........D.................FV.........N..Y.SFH...........................R....I..A..............W.A. | | | | | | | | | (SEQ ID NO:17) |
| 292.64.6.5.5 | ..Q.........D.................T.I........N..Y.L..........S..L..R............R....F.A........W.A. | | | | | | | | | (SEQ ID NO:19) |
| 292.105.4.1 | ..Q.........D.................T.I........N..Y.L..........S..L..R............R....F.A........W.A. | | | | | | | | | (SEQ ID NO:21) |
| 292.109.4.4 | ..Q.........D.................T.I........N..Y.L..........S..L..R............R....F.A........W.A. | | | | | | | | | (SEQ ID NO:23) |
| 292.118.6.4 | ..Q..............V.............KT.I......N..Y.I.............................R....A.............W.A. | | | | | | | | | (SEQ ID NO:25) |
| | | | CDR 1 | | CDR 2 | | | | CDR 3 | |

Figure 4. Alignment of VL and VH predicted amino acid sequences from mouse anti-human IL31 hybridomas from Bin 1B Residues are numbered and CDRs are defined according to Kabat. The CDRs are underlined. N-linked carbohydrate motifs are highlighted in grey. An "." indicates identity with sequence above.

```
VL          1          10         20         30         40         50         60         70         80         90         100
            |          |          |          |          |          |          |          |          |          |          |
Kk2/MMIG27  DIQMTQSPASLSASVGETVTITCRASGNIHNYLAWYQQKQGKSPQLLVYNAKTLADGVPSRFSGSGSGTQYSLKINSLQPEDFGSYYCQHFWSTP                  (SEQ ID NO:91)
292.12.3.1  .................................................................R.E......................WTFGGGTKLEIK         (SEQ ID NO:8)
292.84.1.6  ....................................R........................... R.E......................                      (SEQ ID NO:8)
292.72.3.1  ....S...........................S..........E...................S.........T....I                                 (SEQ ID NO:26)
                                             CDR 1                         CDR 2                                CDR 3

VH          1          10         20         30    36    40         50         65    70         80         90         103    110
            |          |          |          |          |          |          |          |          |          |          |       |
VH3         QVQLQQPGAELVRPGSSVKLSCKASGYTFTSYWMDWVKQRPGQGLEWIGNIYPSDSETHYNQKFKDKATLTVDKSSSTAYMQLSSLTSEDSAVYYCAI  FPDGYYAAPYGMDYWGQGTSVTVSS  (SEQ ID NO:92)
292.12.3.1  ....S...A..A..N.c...........L.R..Q.............A...G.GD.R.S....G...A.........NN.A.........F.F..........Y..S..N.E......S......  (SEQ ID NO:9)
292.84.1.6  ....S...A..A........  ......L.R..Q.............T..G.GD.R.S....G.S.A....N......NN.A.........A.................................  (SEQ ID NO:9)
292.72.3.1  ..V.S...A..A........  ......L.R..Q.............A..R.GD.R.S....G....A....T................................Y..S..N.E......S......  (SEQ ID NO:27)
                                CDR 1                  CDR 2                                                    CDR 3
```

VARIABLE REGION SEQUENCES OF IL-31 MONOCLONAL ANTIBODIES AND METHODS OF USE

BACKGROUND OF THE INVENTION

The skin plays an important role in the immune system and consists of layers. The epidermis is a surface layer. Underneath the epidermis is the dermis, a layer of connective tissue. Underneath the dermis, is the hypodermis, a layer of large amounts of adipose tissue. Circulating T lymphocytes migrate to the skin under normal and inflammatory conditions. The cutaneous lymphocyte antigen (CLA) is considered a homing receptor for T cells with tropism for the skin. Santamaria-Babi, L., *Eur. J. Dermatol.* 14:13-18, 2004.

Several diseases of the skin are known to express high levels of CLA+ T cells, including atopic dermatitis, contact dermatitis, drug-induced allergic reactions, skin-tropic viruses and viral associated pruritis, vitiligo, cutaneous T cell lymphoma, alopecia aerata, acne rosacea, acne vulgaris, prurigo nodularis, and bullous pemphigoid. There is a need to treat such skin T cell mediated diseases.

The demonstrated in vivo activities of the cytokine family illustrate the enormous clinical potential of, and need for, other cytokines, cytokine agonists, and cytokine antagonists. IL-31, a newly identified cytokine. IL-31, when over-expressed in mice, results in dermatitis-like symptoms. Both skin-homing T cells and epidermal kerationcytes have been implicated in the pathology of skin diseases in humans. The present invention addresses these needs by providing antagonists to pro-inflammatory cytokine IL-31. Such antagonists of the present invention, which may block, inhibit, reduce, antagonize or neutralize the activity of IL-31, include soluble IL-31RA receptors and neutralizing anti-IL-31 antibodies. The invention further provides uses therefore in inflammatory disease, as well as related compositions and methods.

Monoclonal antibody technology has provided a vast array of therapeutics as well as diagnostics for use in identifying and treating disease. Many clinical applications have been focused on murine antihuman monoclonal antibodies, which are raised in mouse cells but which specifically bind a human antigen. In addition, chimeric antibodies composed of human and non-human amino acid sequences are being developed. Particularly, hybrid antibody molecules having variable regions derived from, for example, a murine immunoglobulin fused to constant regions derived from a human immunoglobulin have been described. See e.g., U.S. Pat. No. 4,816,567; Winter et al. (1991) Nature 349:293-299; and Lobuglio et al. (1989) Proc. Nat. Acad. Sci. USA 86:4220-4224. Further, since constant regions are not required for antigen recognition or binding, antibody fragments such as F(ab), F(ab')$_2$ and Fv which do not comprise the Fc portion have been indicated as useful candidates for clinical therapy.

A number of recombinant or biosynthetic molecules comprising rodent antigen-binding sites have been described. Particularly, molecules having rodent antigen-binding sites built directly onto human antibodies by grafting only the rodent binding site, rather than the entire variable domain, into human immunoglobulin heavy and light chain domains have been described. See, e.g., Riechmann et al. (1988) Nature 332:323-327 and Verhoeyen et al. (1988) Science 239:1534-1536. Molecules having an antigen-binding site wherein at least one of the complementarity determining regions (CDRS) of the variable domain is derived from a murine monoclonal antibody and the remaining immunoglobulin-derived parts of the molecule are derived from human immunoglobulin have been described in U.K Patent Publication No. GB 2,276,169, published Sep. 21, 1994. A number of single chain antigen-binding site polypeptides and single chain Fv (sFv) molecules have also been described. See, e.g., U.S. Pat. Nos. 5,132,405 and 5,091,513 to Huston et al.; and U.S. Pat. No. 4,946,778 to Ladner et al.

The effector function(s) of the Fc domain of an antibody include phagocytosis, release of inflammatory mediators, regulation of antibody production, and most importantly antibody-dependent cell-mediated cytotoxicity (ADCC) and complement dependent cytotoxicity (CDC). The degree with which any of these effector functions are induced depends on the interaction of the Fc domain with the relevant protein mediators, the Fcγ receptors and C1q, and differs depending on the IgG subclass constant regions (Fe) and their interaction with these proteins.

The Fc domain of IgG1 interacts with FcγRI, FcγRIIa, and FcγRIII on immune system effector cells. The precise role of the different Fcγ receptors remains to be elucidated but FcγRIIIA is thought to be the most important ADCC mediating receptor expressed primarily on NK cells but also monocytes and macrophages. IgG1 also binds C1q and can trigger CDC which is mediated principally by NK cells expressing FcγRIII. The IgG4 Fc domain has largely reduced binding affinity to the different Fcγ receptors and C1q, corresponding to reduced ADCC and CDC. While IgG1 shows generally high activity towards both ADCC and CDC, IgG4 is regarded as having low to no ADCC or CDC activity.

The binding affinity of the effector negative IgG4 mAb is greatly reduced if not abolished when compared to other IgG isotype mAbs. However, the ability to interact with the Brambell receptor (FcRn) is retained in IgG4 thus affecting the pharmacokinetics of the IgG4 isotype mAb through an increased half-life.

Thus, there is a need for molecules which provide the amino acid sequences of anti-human IL-31 in conjunction with a human IgG4 Fc molecule for treating IL-31 mediated inflammation.

BRIEF DESCRIPTION OF THE FIGURES

FIG. 1 is an alignment of the amino acid sequences of the variable domains from the light chains and heavy chains of clones 292.12.3.1, 292.84.1.6, 292.63.5.3, and 294.144.3.5.

FIG. 2 is an alignment of the amino acid sequences of the variable domains from the light chains and heavy chains of clones 292.12.3.1 and 292.84.1.6.

FIGS. 3 and 4 are an alignment of the amino acid sequences of the light and heavy variable regions of mouse anti-human IL-31 monoclonal antibodies.

DETAILED DESCRIPTION OF THE INVENTION

Prior to setting forth the invention in detail, it may be helpful to the understanding thereof to define the following terms:

As used herein, the term "antibodies" includes polyclonal antibodies, affinity-purified polyclonal antibodies, monoclonal antibodies, and antigen-binding fragments, such as F(ab')$_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced.

The term "chimeric antibody" or "chimeric antibodies" refers to antibodies whose light and heavy chain genes have been constructed, typically by genetic engineering, from immunoglobulin variable and constant region genes belonging to different species. For example, the variable segments of the genes from a mouse monoclonal antibody may be joined to human constant segments, such as gamma 1 and gamma 3. A typical therapeutic chimeric antibody is thus a hybrid protein composed of the variable or antigen-binding domain from a mouse antibody and the constant domain from a human antibody, although other mammalian species may be used.

As used herein, the term "immunoglobulin" refers to a protein consisting of one or more polypeptides substantially encoded by immunoglobulin genes. One form of immunoglobulin constitutes the basic structural unit of an antibody. This form is a tetramer and consists of two identical pairs of immunoglobulin chains, each pair having one light and one heavy chain. In each pair, the light and heavy chain variable regions are together responsible for binding to an antigen, and the constant regions are responsible for the antibody effector functions.

Full-length immunoglobulin "light chains" (about 25 Kd or 214 amino acids) are encoded by a variable region gene at the NH2-terminus (about 110 amino acids) and a kappa or lambda constant region gene at the COOH-terminus. Full-length immunoglobulin "heavy chains" (about 50 Kd or 446 amino acids), are similarly encoded by a variable region gene (about 116 amino acids) and one of the other aforementioned constant region genes (about 330 amino acids). Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids. (See generally, Fundamental Immunology (Paul, W., ed., 2nd ed. Raven Press, N.Y., 1989), Ch. 7 (incorporated by reference in its entirety for all purposes).

An immunoglobulin light or heavy chain variable region consists of a "framework" region interrupted by three hypervariable regions. Thus, the term "hypervariable region" refers to the amino acid residues of an antibody which are responsible for antigen binding. The hypervariable region comprises amino acid residues from a "Complementarity Determining Region" or "CDR" (i.e., residues 24-34 (L1), 50-56 (L2) and 89-97 (L3) in the light chain variable domain and 31-35 (H1), 50-65 (H2) and 95-102 (H3) in the heavy chain variable domain (Kabat et al., Sequences of Proteins of Immunological Interest, 5th Ed. Public Health Service, National Institutes of Health, Bethesda, Md. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, 1987, J. Mol. Biol. 196: 901-917) (both of which are incorporated herein by reference). "Framework Region" or "FR" residues are those variable domain residues other than the hypervariable region residues as herein defined. The sequences of the framework regions of different light or heavy chains are relatively conserved within a species. Thus, a "human framework region" is a framework region that is substantially identical (about 85% or more, usually 90-95% or more) to the framework region of a naturally occurring human immunoglobulin. The framework region of an antibody, that is the combined framework regions of the constituent light and heavy chains, serves to position and align the CDR's. The CDR's are primarily responsible for binding to an epitope of an antigen.

Accordingly, the term "humanized" immunoglobulin refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor". Constant regions need not be present, but if they are, they must be substantially identical to human immunoglobulin constant regions, i.e., at least about 85-90%, preferably about 95% or more identical. Hence, all parts of a humanized immunoglobulin, except possibly the CDR's, are substantially identical to corresponding parts of natural human immunoglobulin sequences. A "humanized antibody" is an antibody comprising a humanized light chain and a humanized heavy chain immunoglobulin. For example, a humanized antibody would not encompass a typical chimeric antibody as defined above, e.g., because the entire variable region of a chimeric antibody is non-human.

The term "genetically altered antibodies" means antibodies wherein the amino acid sequence has been varied from that of a native antibody. Because of the relevance of recombinant DNA techniques in the generation of antibodies, one need not be confined to the sequences of amino acids found in natural antibodies; antibodies can be redesigned to obtain desired characteristics. The possible variations are many and range from the changing of just one or a few amino acids to the complete redesign of, for example, the variable or constant region. Changes in the constant region will, in general, be made in order to improve or alter characteristics, such as complement fixation, interaction with membranes and other effector functions. Changes in the variable region will be made in order to improve the antigen binding characteristics.

In addition to antibodies, immunoglobulins may exist in a variety of other forms including, for example, single-chain or Fv, Fab, and (Fab')$_2$, as well as diabodies, linear antibodies, multivalent or multispecific hybrid antibodies (as described above and in detail in: Lanzavecchia et al., Eur. J. Immunol. 17, 105 (1987)) and in single chains (e.g., Huston et al., Proc. Natl. Acad. Sci. U.S.A., 85, 5879-5883 (1988) and Bird et al., Science, 242, 423-426 (1988), which are incorporated herein by reference). (See, generally, Hood et al., "Immunology", Benjamin, N.Y., 2nd ed. (1984), and Hunkapiller and Hood, Nature, 323, 15-16 (1986), which are incorporated herein by reference).

As used herein, the terms "single-chain Fv," "single-chain antibodies," "Fv" or "scFv" refer to antibody fragments that comprises the variable regions from both the heavy and light chains, but lacks the constant regions, but within a single polypeptide chain. Generally, a single-chain antibody further comprises a polypeptide linker between the VH and VL domains which enables it to form the desired structure which would allow for antigen binding. Single chain antibodies are discussed in detail by Pluckthun in The Pharmacology of Monoclonal Antibodies, vol. 113, Rosenburg and Moore eds. Springer-Verlag, New York, pp. 269-315 (1994); see also International Patent Application Publication No. WO 88/01649 and U.S. Pat. Nos. 4,946,778 and 5,260,203, the disclosures of which are incorporated by reference for any purpose. In specific embodiments, single-chain antibodies can also be bi-specific and/or humanized.

A "Fab fragment" is comprised of one light chain and the $C_{H1}$ and variable regions of one heavy chain. The heavy chain of a Fab molecule cannot form a disulfide bond with another heavy chain molecule.

A "Fab' fragment" contains one light chain and one heavy chain that contains more of the constant region, between the $C_{H1}$ and $C_{H2}$ domains, such that an interchain disulfide bond can be formed between two heavy chains to form a F(ab')$_2$ molecule.

A "F(ab')$_2$ fragment" contains two light chains and two heavy chains containing a portion of the constant region between the $C_{H1}$ and $C_{H2}$ domains, such that an interchain disulfide bond is formed between two heavy chains.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to 110%.

All references cited herein are incorporated by reference in their entirety.

The present invention is based in part upon the determination of the amino acid sequences of monoclonal antibodies that were described in co-owned U.S. patent application Ser. No. 11/430,066, filed May 8, 2006, which was published on Dec. 7, 2006 as U.S. Patent Publication No. 2006-0275296, incorporated herein by reference. Hybridomas expressing the neutralizing monoclonal antibodies to human IL-31 described above were deposited with the American Type Tissue Culture Collection (ATCC; 10801 University Blvd, Manassas Va. 20110-2209) patent depository as original deposits under the Budapest Treaty and were given the following ATCC Accession No.s: clone 292.12.3.1 (ATCC Patent Deposit Designation PTA-6815, deposited Jun. 29, 2005); clone 292.72.3.1 (ATCC Patent Deposit Designation PTA-6816, deposited Jun. 29, 2005); clone 292.63.5.3 (ATCC Patent Deposit Designation PTA-6829, deposited Jul. 6, 2005); clone 292.118.6.4 (ATCC Patent Deposit Designation PTA-6830, deposited Jul. 6, 2005); clone 294.163.2.1 (ATCC Patent Deposit Designation PTA-6831, deposited Jul. 6, 2005); clone 292.84.1.6 (ATCC Patent Deposit Designation PTA-6871, deposited Jul. 19, 2005); clone 294.35.2.6.3 (ATCC Patent Deposit Designation PTA-6872, deposited Jul. 19, 2005); clone 294.154.5.6 ATCC Patent Deposit Designation PTA-6875, deposited Jul. 19, 2005); and clone 294.144.3.5 (ATCC Patent Deposit Designation PTA-6873, deposited Jul. 19, 2005).

The present invention provides the amino acid sequences of the light and heavy chain variable regions of the monoclonal antibodies produced by these hybridomas to be used to generate antibodies and antibody fragments, which bind to the IL-31 ligand and can be used in conjunction with an human IgG4 Fc molecule, for example by expression as a fusion protein, to antagonize IL-31 thereby inhibiting, blocking, reducing, or neutralizing inflammation in general, and the symptoms of dermatitis and pruritic diseases. Such antibodies can comprise antibodies or antibody fragments, comprising or consisting of a light chain variable region and a heavy chain variable region, and can be chimeric, humanized, or antibody fragments that neutralize, inhibit, reduce, prevent or minimize the effects of IL-31 on its receptor. Clinical outcomes of the antibody or antibody fragments can be a reduction in inflammatory diseases, such as dermatitis and pruritic diseases as further described herein. In an embodiment, the dermatitis is atopic dermatitis. In another embodiment the dermatitis is prurigo nodularis. In another embodiment, the dermatitis is eczema.

IL-31 is a recently discovered T cell cytokine which, when over-expressed in mice, results in dermatitis-like symptoms. See also, Dillon, et al., Nature Immunol. 5:752-760, 2004. Both skin-homing T cells and epidermal kerationcytes have been implicated in the pathology of skin diseases in humans. IL-31 mRNA and protein expression is restricted to the skin-homing CLA+ T cell population in both atopic dermatitis (AD) patients and normal individuals, while analysis of the receptor for IL-31, IL-31RA, by immunohistochemistry (IHC) suggests slightly higher levels of IL-31RA expression on skin keratinocytes in skin biopsies from acute and chronic AD sufferers compared to normal individuals.

IL-31 is the HUGO name for a cytokine that has been previously described as Zcyto17rlig in a published U.S. patent application (See publication number 20030224487, Sprecher, Cindy et al., 2003, incorporated herein by reference). See also, Dillon, et al., Nature Immunol., supra. The heterodimeric receptor for IL-31 was also described in 20030224487 as zcytor17 (HUGO name, IL-31RA) which forms a heterodimer with OncostatinM receptor beta (OS-MRbeta). IL-31 was isolated from a cDNA library generated from activated human peripheral blood cells (hPBCs), which were selected for CD3. CD3 is a cell surface marker unique to cells of lymphoid origin, particularly T cells. The polypeptide sequence for human IL-31 is shown in SEQ ID NO:2. The polypeptide sequence for murine IL-31 is shown in SEQ ID NO:4. As used herein the term, IL-31 means IL-31 as used in U.S. patent publication number 20030224487, as shown above. The secretory signal sequence of IL-31 is comprised of amino acid residues 1 (Met) to 23 (Ala), and the mature polypeptide is comprised of amino acid residues 24 (Ser) to 164 (Thr) (as shown in SEQ ID NO:2). Further N-terminal sequencing analysis of purified IL-31 from 293T cells showed an N-terminus at residue 27 (Leu) as shown in SEQ ID NO:2, with the mature polypeptide comprised of amino acid residues 27 (Leu) to 164 (Thr) (as shown in SEQ ID NO:2).

IL-31 is the HUGO name for a cytokine that has been previously described as Zcyto17rlig in a published U.S. patent application (See publication number 20030224487, Sprecher, Cindy et al., 2003, incorporated herein by reference). See also, Dillon, et al., Nature Immunol., supra. The heterodimeric receptor for IL-31 was also described in 20030224487 as zcytor17 (HUGO name, IL-31RA) which forms a heterodimer with OncostatinM receptor beta (OS-MRbeta). IL-31 was isolated from a cDNA library generated from activated human peripheral blood cells (hPBCs), which were selected for CD3. CD3 is a cell surface marker unique to cells of lymphoid origin, particularly T cells. The polynucleotide and polypeptide sequences for human IL-31 are shown in SEQ ID NOs: 1 and 2, respectively. The polynucleotide and polypeptide sequences for murine IL-31 are shown in SEQ ID NOs: 3 and 4, respectively. As used herein the term, IL-31 means IL-31 as used in U.S. patent publication number 20030224487, as shown above. The secretory signal sequence of IL-31 is comprised of amino acid residues 1 (Met) to 23 (Ala), and the mature polypeptide is comprised of amino acid residues 24 (Ser) to 164 (Thr) (as shown in SEQ ID NO:2). Further N-terminal sequencing analysis of purified IL-31 from 293T cells showed an N-terminus at residue 27 (Leu) as shown in SEQ ID NO:2, with the mature polypeptide comprised of amino acid residues 27 (Leu) to 164 (Thr) (as shown in SEQ ID NO:2).

The polypeptide sequence for the IL-31RA (IL-31 receptor) is shown in SEQ ID NO:5, and the polypeptide sequence for OncostatinM receptor beta (OSMRbeta) is shown in SEQ ID NO:6.

The IL-31RA and OSMRbeta receptors belong to the Class I cytokine receptor subfamily that includes, but is not limited to, the receptors for IL-2, IL-4, IL-7, Lif, IL-12, IL-15, EPO, TPO, GM-CSF and G-CSF (for a review see, Cosman, "The Hematopoietin Receptor Superfamily" in *Cytokine* 5(2): 95-106, 1993). The IL-31RA subunit is fully described in commonly-owned PCT Patent Application No. US01/20484 (WIPO publication No. WO 02/00721). Analysis of the tissue distribution of the mRNA of the IL-31RA subunit revealed expression in activated CD4+ and CD8+ T-cell subsets, CD14+ monocytes, and weaker expression in CD19+ B-cells. Moreover, the mRNA was present in both resting or activated monocytic cell lines THP-1 (ATCC No. TIB-202), U937 (ATCC No. CRL-1593.2) and HL60 (ATCC No. CCL-240).

Inhibition, neutralization, or blocking signal transduction by the molecules comprising a light chain variable domain and or a heavy chain variable domain, termed "IL-31 binding molecules" or "IL-31 antagonists" herein, can be measured by a number of assays known to one skilled in the art. For example, assays measuring a reduction in proliferation include assays for reduction of a dye such as AlamarBlue™ (AccuMed International, Inc. Westlake, Ohio), 3-(4,5-dimethylthiazol-2-yl)-2,5-diphenyl tetrazolium bromide (Mosman, *J. Immunol. Meth.* 65: 55-63, 1983); 3,(4,5 dimethyl thiazol-2-yl)-5-3-carboxymethoxyphenyl-2H-tetrazolium; 2,3-bis(2-methoxy-4-nitro-5-sulfophenyl)-5-[(phenylamino)carbonyl]-2H-tetrazolium hydroxide; and cyanoditolyl-tetrazolium chloride (which are commercially available from Polysciences, Inc., Warrington, Pa.); mitogenesis assays, such as measurement of incorporation of $^3$H-thymidine; dye exclusion assays using, for example, naphthalene black or trypan blue; dye uptake using diacetyl fluorescein; and chromium release. See, in general, Freshney, *Culture of Animal Cells: A Manual of Basic Technique,* 3rd ed., Wiley-Liss, 1994, which is incorporated herein by reference. In addition to the above, see published U.S. patent publication number 20030224487, (Sprecher, Cindy et al., 2003) for an example of BaF3 cells expressing IL-31RA and full-length OSMRbeta.

Methods for preparing the polynucleotides encoding the antibodies described herein (including DNA and RNA) are well known in the art. Total RNA can be prepared using guanidinium isothiocyanate extraction followed by isolation by centrifugation in a CsCl gradient (Chirgwin et al., *Biochemistry* 18:52-94, 1979). Poly (A)$^+$ RNA is prepared from total RNA using the method of Aviv and Leder (*Proc. Natl. Acad. Sci. USA* 69:1408-12, 1972). Complementary DNA (cDNA) is prepared from poly(A)$^+$ RNA using known methods. In the alternative, genomic DNA can be isolated. Polynucleotides encoding IL-31 antibodies are then identified and isolated by, for example, hybridization or PCR.

The present invention also includes IL-31 binding molecules or IL-31 antagonists that bind functional fragments of IL-31 polypeptides and nucleic acid molecules encoding such functional fragments. A "functional" IL-31 or fragment thereof as defined herein is characterized by its proliferative or differentiating activity, by its ability to induce or inhibit specialized cell functions, or by its ability to bind specifically to an anti-IL-31 antibody or IL-31 RA or antibody or IL-31RA/OSMRbeta heterodimers of these receptors (either soluble or immobilized). As previously described herein, IL-31 is characterized by a four-helical-bundle structure comprising helix A (amino acid residues 38-52), helix B (amino acid residues 83-98), helix C (amino acid residues 104-117) and helix D (amino acid residues 137-152), as shown in SEQ ID NO:2. Thus, the present invention further provides fusion proteins encompassing: (a) polypeptide molecules comprising one or more of the helices described above; and (b) functional fragments comprising one or more of these helices. The other polypeptide portion of the fusion protein may be contributed by another four-helical-bundle cytokine, such as IL-15, IL-2, IL-4 and GM-CSF, or by a non-native and/or an unrelated secretory signal peptide that facilitates secretion of the fusion protein.

The present invention also provides IL-31 binding molecules or IL-31 antagonists that bind to polypeptide fragments or peptides comprising an epitope-bearing portion of a IL-31 polypeptide described herein. Such fragments or peptides may comprise an "immunogenic epitope," which is a part of a protein that elicits an antibody response when the entire protein is used as an immunogen. Immunogenic epitope-bearing peptides can be identified using standard methods (see, for example, Geysen et al., *Proc. Nat'l Acad. Sci. USA* 81:3998 (1983)). The binding of the antibodies to these functional fragments results in inhibition, blocking, neutralization, and/or reduction in signal transduction of IL-31 on its cognate receptor.

In contrast, polypeptide fragments or peptides may comprise an "antigenic epitope," which is a region of a protein molecule to which an antibody can specifically bind. Certain epitopes consist of a linear or contiguous stretch of amino acids, and the antigenicity of such an epitope is not disrupted by denaturing agents. It is known in the art that relatively short synthetic peptides that can mimic epitopes of a protein can be used to stimulate the production of antibodies against the protein (see, for example, Sutcliffe et al., *Science* 219:660 (1983)). Accordingly, antigenic epitope-bearing peptides and polypeptides of the present invention are useful to raise antibodies (e.g., neutralizing antibodies) that bind with the polypeptides described herein. Hopp/Woods hydrophilicity profiles can be used to determine regions that have the most antigenic potential (Hopp et al., 1981, ibid. and Hopp, 1986, ibid.). For example, in human IL-31, hydrophilic regions include amino acid residues 54-59 of SEQ ID NO:2, amino acid residues 129-134 of SEQ ID NO:2, amino acid residues 53-58 of SEQ ID NO:2, amino acid residues 35-40 of SEQ ID NO:2, and amino acid residues 33-38 of SEQ ID NO:2. For example, in mouse IL-31, hydrophilic regions include amino acid residues 34-39 of SEQ ID NO:4, amino acid residues 46-51 of SEQ ID NO:4, amino acid residues 131-136 of SEQ ID NO:4, amino acid residues 158-163 of SEQ ID NO:4, and amino acid residues 157-162 of SEQ ID NO:4.

Antigenic epitope-bearing peptides and polypeptides preferably contain at least four to ten amino acids, at least ten to fourteen amino acids, or about fourteen to about thirty amino acids of SEQ ID NO:2 or SEQ ID NO:4. Such epitope-bearing peptides and polypeptides can be produced by fragmenting a IL-31 polypeptide, or by chemical peptide synthesis, as described herein. Moreover, epitopes can be selected by phage display of random peptide libraries (see, for example, Lane and Stephen, *Curr. Opin. Immunol.* 5:268 (1993); and Cortese et al, *Curr. Opin. Biotechnol.* 7:616 (1996)). Standard methods for identifying epitopes and producing antibodies from small peptides that comprise an epitope are described, for example, by Mole, "Epitope Mapping," in *Methods in Molecular Biology*, Vol. 10, Manson (ed.), pages 105-116 (The Humana Press, Inc. 1992); Price, "Production and Characterization of Synthetic Peptide-Derived Antibodies," in *Monoclonal Antibodies: Production Engineering and Clinical Application*, Ritter and Ladyman (eds.), pages 60-84 (Cambridge University Press 1995), and Coligan et al (eds.), *Current Protocols in Immunology*, pages 9.3.1-9.3.5 and pages 9.4.1-9.4.11 (John Wiley & Sons 1997).

The activity of the antibodies as described herein can be measured by their ability to inhibit, or reduce proliferation using a variety of assays that measure proliferation of and/or binding to cells expressing the IL-31RA receptor. Of particular interest are changes in IL-31-dependent cells. Suitable cell lines to be engineered to be IL-31-dependent include the IL-3-dependent BaF3 cell line (Palacios and Steinmetz, *Cell* 41: 727-734, 1985; Mathey-Prevot et al., *Mol. Cell. Biol.* 6: 4133-4135, 1986), FDC-P1 (Hapel et al., *Blood* 64: 786-790, 1984), and MO7e (Kiss et al., *Leukemia* 7: 235-240, 1993). Growth factor-dependent cell lines can be established according to published methods (e.g. Greenberger et al., *Leukemia Res.* 8: 363-375, 1984; Dexter et al., in Baum et al. Eds., *Experimental Hematology Today*, 8th Ann. Mtg. Int. Soc. Exp. Hematol. 1979, 145-156, 1980).

The activity of the anti-IL-31 antibodies described herein can be measured by a silicon-based biosensor microphysiometer which measures the extracellular acidification rate or proton excretion associated with receptor binding and subsequent physiologic cellular responses. An exemplary device is the Cytosensor™ Microphysiometer manufactured by Molecular Devices, Sunnyvale, Calif. A variety of cellular responses, such as cell proliferation, ion transport, energy production, inflammatory response, regulatory and receptor activation, and the like, can be measured by this method. See, for example, McConnell, H. M. et al., *Science* 257:1906-1912, 1992; Pitchford, S. et al., *Meth. Enzymol.* 228:84-108, 1997; Arimilli, S. et al., *J. Immunol. Meth.* 212:49-59, 1998; Van Liefde, I. et al., *Eur. J. Pharmacol.* 346:87-95, 1998.

Antagonists are also useful as research reagents for characterizing sites of ligand-receptor interaction. Antagonists are useful to inhibit expansion, proliferation, activation, and/ or differentiation of cells involved in regulating hematopoiesis. Inhibitors of IL-31 activity (IL-31 antagonists) include anti-IL-31 antibodies and soluble IL-31 receptors, as well as other peptidic and non-peptidic agents (including ribozymes).

Inhibition the activity of IL-31 can be measured by a number of assays. In addition to those assays disclosed herein, samples can be tested for inhibition of IL-31 activity within a variety of assays designed to measure receptor binding, the stimulation/inhibition of IL-31-dependent cellular responses or proliferation of IL-31RA receptor-expressing cells.

A IL-31-binding polypeptide, including IL-31 binding molecules or IL-31 antagonists can also be used for purification of ligand. The polypeptide is immobilized on a solid support, such as beads of agarose, cross-linked agarose, glass, cellulosic resins, silica-based resins, polystyrene, cross-linked polyacrylamide, or like materials that are stable under the conditions of use. Methods for linking polypeptides to solid supports are known in the art, and include amine chemistry, cyanogen bromide activation, N-hydroxysuccinimide activation, epoxide activation, sulfhydryl activation, and hydrazide activation. The resulting medium will generally be configured in the form of a column, and fluids containing ligand are passed through the column one or more times to allow ligand to bind to the receptor polypeptide. The ligand is then eluted using changes in salt concentration, chaotropic agents (guanidine HCl), or pH to disrupt ligand-receptor binding.

An assay system that uses a ligand-binding receptor (or an antibody, one member of a complement/anti-complement pair) or a binding fragment thereof, and a commercially available biosensor instrument (BIAcore, Pharmacia Biosensor, Piscataway, N.J.) may be advantageously employed. Such receptor, antibody, member of a complement/anti-complement pair or fragment is immobilized onto the surface of a receptor chip. Use of this instrument is disclosed by Karlsson, J. *Immunol. Methods* 145:229-40, 1991 and Cunningham and Wells, *J. Mol. Biol.* 234:554-63, 1993. A receptor, antibody, member or fragment is covalently attached, using amine or sulfhydryl chemistry, to dextran fibers that are attached to gold film within the flow cell. A test sample is passed through the cell. If a ligand, epitope, or opposite member of the complement/anti-complement pair is present in the sample, it will bind to the immobilized receptor, antibody or member, respectively, causing a change in the refractive index of the medium, which is detected as a change in surface plasmon resonance of the gold film. This system allows the determination of on- and off-rates, from which binding affinity can be calculated, and assessment of stoichiometry of binding. Alternatively, ligand/receptor binding can be analyzed using SELDI™ technology (Ciphergen, Inc., Palo Alto, Calif.).

IL-31 binding molecules or IL-31 antagonists can be used to block the biological action of pro-inflammatory IL-31 and are useful as anti-inflammatory therapeutics in a variety of diseases as described herein. One of skill in the art would recognize that antigenic, epitope-bearing polypeptides contain a sequence of at least 6, preferably at least 9, and more preferably at least 15 to about 30 contiguous amino acid residues of a IL-31 polypeptide (e.g., SEQ ID NO:2). Polypeptides comprising a larger portion of a IL-31 polypeptide, i.e., from 30 to 100 residues up to the entire length of the amino acid sequence are included. Antigens or immunogenic epitopes can also include attached tags, adjuvants, vehicles and carriers, as described herein. Suitable antigens include the IL-31 polypeptide encoded by SEQ ID NO:2 from amino acid number 24 to amino acid number 164, or a contiguous 9 to 141 amino acid fragment thereof. Other suitable antigens include, the full length and the mature IL-31, helices A-D, and individual or multiple helices A, B, C, and D, of the IL-31 four-helical-bundle structure, as described herein. Preferred peptides to use as antigens are hydrophilic peptides such as those predicted by one of skill in the art from a hydrophobicity plot, as described herein, for example, amino acid residues 114-119, 101-105, 126-131, 113-118, and 158-162 of SEQ ID NO:2; and amino acid residues 34-39, 46-51, 131-136, 158-163 and 157-162 of SEQ ID NO:4. Moreover, IL-31 antigenic epitopes as predicted by a Jameson-Wolf plot, e.g., using DNASTAR Protean program (DNASTAR, Inc., Madison, Wis.) serve as preferred antigens, and are readily determined by one of skill in the art.

IL-31 binding molecules or IL-31 antagonists are considered to be specifically binding if: 1) they exhibit a threshold level of binding activity, and 2) they do not significantly cross-react with related polypeptide molecules. A threshold level of binding is determined if IL-31 binding molecules or IL-31 antagonists herein bind to a IL-31 polypeptide, peptide or epitope with an affinity at least 10-fold greater than the binding affinity to control (non-IL-31) polypeptide. It is preferred that the antibodies exhibit a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of IL-31 binding molecules or IL-31 antagonists can be readily determined by one of ordinary skill in the art, for example, by Scatchard analysis (Scatchard, G., *Ann. NY Acad. Sci.* 51: 660-672, 1949).

Whether IL-31 binding molecules or IL-31 antagonists do not significantly cross-react with related polypeptide molecules is shown, for example, by the IL-31 binding molecules or IL-31 antagonists detecting IL-31 polypeptide but not known related polypeptides using a standard Western blot analysis (Ausubel et al., ibid.). Examples of known related polypeptides are those disclosed in the prior art, such as known orthologs, and paralogs, and similar known members of a protein family. Screening can also be done using non-human IL-31, and IL-31 mutant polypeptides. Moreover, IL-31 binding molecules or IL-31 antagonists can be "screened against" known related polypeptides, to isolate a population that specifically binds to the IL-31 polypeptides. For example, IL-31 binding molecules or IL-31 antagonists are adsorbed to related polypeptides adhered to insoluble matrix; IL-31 binding molecules or IL-31 antagonists specific to IL-31 will flow through the matrix under the proper buffer conditions. *Antibodies: A Laboratory Manual*, Harlow and Lane (eds.), Cold Spring Harbor Laboratory Press, 1988; *Current Protocols in Immunology*, Cooligan, et al. (eds.), National Institutes of Health, John Wiley and Sons, Inc., 1995.

Monoclonal antibodies purified from tissue culture media are characterized for their ability to block or reduce the receptor binding activity ("neutralization assay") of purified recombinant huIL-31 on BaF3/MPL-IL-31 cells.

Binding affinity of the IL-31 binding molecules and IL-31 antagonist can be determined. Goat-anti-Rat IgG-Fc gamma specific Antibody (Jackson) is immobilized onto a CM5 Biacore chip. The assay is optimized to bind each mAb onto the anti-Rat capture surface and then a concentration series of IL-31 is injected across the mAb to see association (Ka) and dissociation (Kd). After each run, the surface is regenerated back to the anti-Rat Antibody with 2 injections of 20 mM HCl. Data is generated for each and evaluation software (BlAevaluation software version 3.2, Pharmacia BIAcore, Uppsala, Sweden) is used to assess the kinetics of the anti-IL-31 antibody binding to the IL-31 protein.

The polynucleotide and polypeptide sequence of the light chain and heavy chain variable regions of clones numbers 292.12.3.1, 292.84.1.6, 292.63.5.3, 294.144.3.5, 292.39.5.3, 292.51.5.2, 292.64.6.5.5, 292.105.4.1, 292.109.4.4, 292.118.6.4, 292.72.3.1. were determined as shown in Example 1. The polypeptide sequence of the amino terminus of the light and heavy chain variable regions of clones numbers were determined as shown in Example 2.

IL-31 binding molecules or IL-31 antagonists in tissue culture media are characterized for their ability to block, inhibit, prevent, or reduce receptor binding when grown in the presence of the purified recombinant proteins human IL-31. For example, the IL-31 binding molecules or IL-31 antagonists can be characterized in a number of ways including binding (i.e, determining if each antibody could inhibit the binding of any other binding), relative affinity, and neutralization.

IL-31 binding molecules or IL-31 antagonists generated by the methods described herein can be tested for neutralization by a variety of methods. For example the luciferase assay as described in published U.S. patent application (See publication number 20030224487, Sprecher, Cindy et al., 2003) can be used. In addition neutralization can be tested by measuring a decrease in the production of pro-inflammatory chemokines such as TARC and MDC from keratinocyte cultures in the presence of ligand and the monoclonal antibody. Neutralization can also be measured by the in vivo models described herein.

In one embodiment, the IL-31 binding molecules or IL-31 antagonists of the present invention are human antigen-binding antibody fragments of the present invention and include, but are not limited to, Fab, Fab' and F(ab')$_2$, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) (i.e., SEQ ID NO: 1, 2, 3, or 4) alone or in combination with the entirety or a portion of the following: hinge region, $C_{H1}$, $C_{H2}$, and $C_{H3}$ domains. Also included in the invention are antigen-binding fragments also comprising any combination of variable region(s) with a hinge region, $C_{H1}$, $C_{H2}$, and $C_{H3}$ domains.

In another embodiment, the IL-31 binding molecules or IL-31 antagonists of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992).

The present invention also includes genetically altered IL-31 binding molecules or IL-31 antagonists that are functionally equivalent to the above-described IL-31 binding molecules or IL-31 antagonists. Modified IL-31 binding molecules or IL-31 antagonists providing improved stability and/or therapeutic efficacy are preferred. Examples of modified antibodies include those with conservative substitutions of amino acid residues, and one or more deletions or additions of amino acids which do not significantly deleteriously alter the antigen binding utility. Substitutions can range from changing or modifying one or more amino acid residues to complete redesign of a region as long as the therapeutic utility is maintained. IL-31 binding molecules or IL-31 antagonists of the present invention can be can be modified post-translationally (e.g., acetylation, and phosphorylation) or can be modified synthetically (e.g., the attachment of a labeling group).

The IL-31 binding molecules or IL-31 antagonists also include chimeric antibodies or chimeric fragments, comprising a variable region as described herein and a constant region derived from a human so that the chimeric antibody or chimeric fragment has a longer half-life, and is less immunogenic when administered to a human subject. The method of making chimeric antibodies and chimeric fragments is known in the art. The variable regions of these IL-31 binding molecules or IL-31 antagonists can be connected with a constant region of a human IgG to form the desired chimeric antibody. An IgG Fc molecule can be fused to the IL-31 binding molecules. To avoid induction of effector function, the IgG Fc molecule can be from an IgG4 Fc molecule. Thus, the amino acid sequences of the variable regions and variable regions as disclosed herein can be used to generate chimeric antibodies wherein the constant region is a human IgG molecule and the light chain and heavy chain variable regions can be selected from those of clones 292.12.3.1, 292.84.1.6, 292.63.5.3, 294.144.3.5, 292.39.5.3, 292.51.5.2, 292.64.6.5.5, 292.105.4.1, 292.109.4.4, 292.118.6.4, and 292.72.3.1. Such chimeric antibodies would have: a) a light chain variable region comprising the amino acid sequence of SEQ ID NO: 8 and a heavy chain variable region comprising the amino acid sequence of SEQ ID NO: 9; b) a light chain variable region comprising the amino acid sequence of SEQ ID NO: 10 and a heavy chain variable region comprising the amino acid sequence of SEQ ID NO: 11; c) a light chain variable region comprising the amino acid sequence of SEQ ID NO: 12 and a heavy chain variable region comprising the amino acid sequence of SEQ ID NO: 13; d) a light chain variable region comprising the amino acid sequence of SEQ ID NO: 14 and a heavy chain variable region comprising the amino acid sequence of SEQ ID NO: 15; e) a light chain variable region comprising the amino acid sequence of SEQ ID NO: 16 and a heavy chain variable region comprising the amino acid sequence of SEQ ID NO: 17; f) a light chain variable region comprising the amino acid sequence of SEQ ID NO: 18 and a heavy chain variable region comprising the amino acid sequence of SEQ ID NO: 19; g) a light chain variable region comprising the amino acid sequence of SEQ ID NO: 20 and a heavy chain variable region comprising the amino acid sequence of SEQ ID NO: 21; h) a light chain variable region comprising the amino acid sequence of SEQ ID NO: 22 and a heavy chain variable region comprising the amino acid sequence of SEQ ID NO: 23; i) a light chain variable region comprising the amino acid sequence of SEQ ID NO: 24 and a heavy chain variable region comprising the amino acid sequence of SEQ ID NO: 25; or j) a light chain variable region comprising the amino acid sequence of SEQ ID NO: 26 and a heavy chain variable region comprising the amino acid sequence of SEQ ID NO: 27 and used in conjunction with an human IgG4 Fc molecule.

Such variable regions can also be generated with or without the signal sequences. Thus, the amino acid sequences of the variable regions and variable regions as disclosed herein can be used to generate chimeric antibodies wherein the constant region is a human IgG molecule and the light chain and heavy chain variable regions can have a signal sequence and can be selected from those of clones 292.12.3.1, 292.84.1.6, 292.63.5.3, 294.144.3.5, 292.39.5.3, 292.51.5.2, 292.64.6.5.5, 292.105.4.1, 292.109.4.4, 292.118.6.4, and 292.72.3.1. Such chimeric antibodies would have: a) a light chain variable region comprising the amino acid sequence of SEQ ID NO: 31 and a heavy chain variable region comprising the amino acid sequence of SEQ ID NO: 32; b) a light chain variable region comprising the amino acid sequence of SEQ ID NO: 2 and a heavy chain variable region comprising the amino acid sequence of SEQ ID NO:4; c) a light chain variable region comprising the amino acid sequence of SEQ ID NO: 35 and a heavy chain variable region comprising the amino acid sequence of SEQ ID NO: 36; d) a light chain variable region comprising the amino acid sequence of SEQ ID NO: 37 and a heavy chain variable region comprising the amino acid sequence of SEQ ID NO: 38; e) a light chain variable region comprising the amino acid sequence of SEQ ID NO: 39 and a heavy chain variable region comprising the amino acid sequence of SEQ ID NO: 40; f) a light chain variable region comprising the amino acid sequence of SEQ ID NO: 41 and a heavy chain variable region comprising the amino acid sequence of SEQ ID NO: 42; g) a light chain variable region comprising the amino acid sequence of SEQ ID NO: 43 and a heavy chain variable region comprising the amino acid sequence of SEQ ID NO: 44; h) a light chain variable region comprising the amino acid sequence of SEQ ID NO: 45 and a heavy chain variable region comprising the amino acid sequence of SEQ ID NO: 46; i) a light chain variable region comprising the amino acid sequence of SEQ ID NO: 47 and a heavy chain variable region comprising the amino acid sequence of SEQ ID NO: 48; or j) a light chain variable region comprising the amino acid sequence of SEQ ID NO: 49 and a heavy chain variable region comprising the amino acid sequence of SEQ ID NO: 50 and used in conjunction with an human IgG4 Fc molecule. Such variable regions can be generated with or without the signal sequences.

The IL-31 binding molecules or IL-31 antagonists include humanized version of the IL-31 binding molecules or IL-31 antagonists described herein. Humanized IL-31 binding molecules or IL-31 antagonists comprise CDRs of a mouse donor immunoglobulin and heavy chain and light chain frameworks of a human acceptor immunoglobulin. The method of making humanized antibody is disclosed in U.S. Pat. Nos. 5,530,101; 5,585,089; 5,693,762; and 6,180,370 (each of which is incorporated by reference in its entirety). The CDRs of these antibodies can then be grafted to any selected human frameworks, which are known in the art, to generate the desired humanized antibody.

The invention also provides IL-31 binding molecules or IL-31 antagonists that competitively inhibit the binding of a monoclonal antibody to a polypeptide of the invention, preferably the polypeptide of SEQ ID NO:2 or SEQ ID NO:4. Competitive inhibition can be determined by any method known in the art, for example, using the competitive binding assays described herein. In preferred embodiments, the antibody competitively inhibits the binding of a monoclonal antibody of the invention by at least 90%, at least 80%, at least 70%, at least 60%, or at least 50% to the polypeptide of SEQ ID NO:2 or SEQ ID NO:4.

The invention also provides IL-31 binding molecules or IL-31 antagonists that competitively inhibit binding of an antibody to an epitope of the invention as determined by any method known in the art for determining competitive binding, for example, the immunoassays described herein. In preferred embodiments, the antibody competitively inhibits binding to the epitope by at least 90%, at least 80%, at least 70%, at least 60%, or at least 50%.

The IL-31 binding molecules or IL-31 antagonists of the present invention include derivatives that are modified, for example, but not by way of limitation, the derivatives include IL-31 binding molecules or IL-31 antagonists that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The IL-31 binding molecules or IL-31 antagonists of the present invention also encompass IL-31 binding molecules or IL-31 antagonists that have half-lives (e.g., serum half-lives) in a mammal, preferably a human, of greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the antibodies of the present invention or fragments thereof in a mammal, preferably a human, result in a higher serum titer of said antibodies or antibody fragments in the mammal, and thus, reduce the frequency of the administration of said antibodies or antibody fragments and/or reduces the concentration of said antibodies or antibody fragments to be administered.

The in vivo half-lives of the IL-31 binding molecules or IL-31 antagonists can be increased by modifying (e.g., substituting, deleting or adding) amino acid residues identified as involved in the interaction between the Fc domain and the FcRn receptor (see, e.g., International Publication Nos. WO 97/34631 and WO 02/060919, which are incorporated herein by reference in their entireties), or by attaching polymer molecules such as high molecular weight polyethyleneglycol (PEG). PEG can be attached with or without a multifunctional linker either through site-specific conjugation of the PEG to the N- or C-terminus of said antibodies or antibody fragments or via epsilon-amino groups present on lysine residues. Linear or branched polymer derivatization that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography.

It is understood that the humanized IL-31 binding molecules or IL-31 antagonists designed by the present method may have additional conservative amino acid substitutions which have substantially no effect on antigen binding or other immunoglobulin functions. By conservative substitutions is intended combinations such as gly, ala; val, ile, leu; asp, glu; asn, gln; ser, thr; lys, arg; and phe, tyr.

Methods for humanizing non-human antibodies are well known in the art. Generally, humanized immunoglobulins, including humanized antibodies, have been constructed by means of genetic engineering. Most humanized immunoglobulins that have been previously described (Jones et al., op. cit.; Verhoeyen et al., op. cit.; Riechmann et al., op. cit.) have comprised a framework that is identical to the framework of a particular human immunoglobulin chain, the acceptor, and three CDR's from a non-human donor immunoglobulin chain. Specifically, humanized antibodies are antibody molecules from non-human species antibody that binds the desired antigen having one or more complementarity determining regions (CDRs) from the non-human species and framework regions from a human immunoglobulin molecule.

The present invention includes criteria by which a limited number of amino acids in the framework of a humanized immunoglobulin chain are chosen to be the same as the amino acids at those positions in the donor rather than in the acceptor, in order to increase the affinity of an antibody comprising the humanized immunoglobulin chain.

The IL-31 binding molecules or IL-31 antagonists of the present invention are generated based in part on the model that two contributing causes of the loss of affinity in prior means of producing humanized antibodies (using as examples mouse antibodies as the source of CDR's) are:

(1) When the mouse CDR's are combined with the human framework, the amino acids in the framework close to the CDR's become human instead of mouse. Without intending to be bound by theory, these changed amino acids may slightly distort the CDR's, because they create different electrostatic or hydrophobic forces than in the donor mouse antibody, and the distorted CDR's may not make as effective contacts with the antigen as the CDR's did in the donor antibody; and Amino acids in the original mouse antibody that are close to, but not part of, the CDR's (i.e., still part of the framework), may make contacts with the antigen that contribute to affinity. These amino acids are lost when the antibody is humanized, because all framework amino acids are made human.

To avoid these problems, and to produce humanized antibodies that have a very strong affinity for a desired antigen, the present invention uses one or more of the following principles for designing humanized immunoglobulins. Also, the criteria may be used singly, or when necessary in combination, to achieve the desired affinity or other characteristics.

A principle is that as acceptor, a framework is used from a particular human immunoglobulin that is unusually homologous to the donor immunoglobulin to be humanized, or use a consensus framework from many human antibodies. For example, comparison of the sequence of a mouse heavy (or light) chain variable region against human heavy (or light) variable regions in a data bank (for example, the National Biomedical Research Foundation Protein Identification Resource) shows that the extent of homology to different human regions varies greatly, typically from about 40% to about 60-70%. By choosing as the acceptor immunoglobulin one of the human heavy (respectively light) chain variable regions that is most homologous to the heavy (respectively light) chain variable region of the donor immunoglobulin, fewer amino acids will be changed in going from the donor immunoglobulin to the humanized immunoglobulin. Hence, and again without intending to be bound by theory, it is believed that there is a smaller chance of changing an amino acid near the CDR's that distorts their conformation. Moreover, the precise overall shape of a humanized antibody comprising the humanized immunoglobulin chain may more closely resemble the shape of the donor antibody, also reducing the chance of distorting the CDR's.

Typically, one of the 3-5 most homologous heavy chain variable region sequences in a representative collection of at least about 10 to 20 distinct human heavy chains will be chosen as acceptor to provide the heavy chain framework, and similarly for the light chain. Preferably, one of the 1-3 most homologous variable regions will be used. The selected acceptor immunoglobulin chain will most preferably have at least about 65% homology in the framework region to the donor immunoglobulin.

In many cases, it may be considered preferable to use light and heavy chains from the same human antibody as acceptor sequences, to be sure the humanized light and heavy chains will make favorable contacts with each other. In this case, the donor light and heavy chains will be compared only against chains from human antibodies whose complete sequence is known, e.g., the Eu, Lay, Pom, Wol, Sie, Gal, Ou and WEA antibodies (Kabat et al., op. cit.; occasionally, the last few amino acids of a human chain are not known and must be deduced by homology to other human antibodies). The human antibody will be chosen in which the light and heavy chain variable regions sequences, taken together, are overall most homologous to the donor light and heavy chain variable region sequences. Sometimes greater weight will be given to the heavy chain sequence. The chosen human antibody will then provide both light and heavy chain acceptor sequences. In practice, it is often found that the human Eu antibody will serve this role.

According to the "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151: 2296 (1993); Chothia et al., J. Mol. Biol., 196: 901 (1987)). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89: 4285 (1992); Presta et al., J. Immunol., 151: 2623 (1993)).

Regardless of how the acceptor immunoglobulin is chosen, higher affinity may be achieved by selecting a small number of amino acids in the framework of the humanized immunoglobulin chain to be the same as the amino acids at those positions in the donor rather than in the acceptor. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585, 089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332). Accordingly, such "humanized" antibodies are chimeric antibodies (U.S. Pat. No. 4,816, 567) wherein substantially less than an intact human variable domain has been substituted by the corresponding sequence from a non-human species.

Humanized antibodies generally have at least three potential advantages over mouse or in some cases chimeric antibodies for use in human therapy:

(1) Because the effector portion is human, it may interact better with the other parts of the human immune system (e.g., destroy the target cells more efficiently by complement-dependent cytotoxicity (CDC) or antibody-dependent cellular cytotoxicity (ADCC)).

(2) The human immune system should not recognize the framework or constant region of the humanized antibody as foreign, and therefore the antibody response against such an injected antibody should be less than against a totally foreign mouse antibody or a partially foreign chimeric antibody.

(3) Injected mouse antibodies have been reported to have a half-life in the human circulation much shorter than the half-life of normal antibodies (D. Shaw et al., J. Immunol., 138, 4534-4538 (1987)). Injected humanized antibodies will presumably have a half-life more similar to naturally occurring human antibodies, allowing smaller and less frequent doses to be given.

In one aspect, the present invention is directed to designing humanized antibodies that are produced by expressing recombinant DNA segments encoding the heavy and light chain CDR's from a donor immunoglobulin capable of binding to a desired antigen, such as IL-31. attached to DNA segments encoding acceptor human framework regions.

The DNA segments will typically further include an expression control DNA sequence operably linked to the humanized immunoglobulin coding sequences, including naturally-associated or heterologous promoter regions. The expression control sequences will be eukaryotic promoter systems in vectors capable of transforming or transfecting eukaryotic host cells, but control sequences for prokaryotic hosts may also be used. Once the vector has been incorporated into the appropriate host, the host is maintained under conditions suitable for high level expression of the nucleotide sequences, and, as desired, the collection and purification of the humanized light chains, heavy chains, light/heavy chain dimers or intact antibodies, binding fragments or other immunoglobulin forms may follow (see, S. Beychok, Cells of Immunoglobulin Synthesis, Academic Press, N.Y., (1979), which is incorporated herein by reference). The anti-IL_31 molecules can be made by expression in mammalian host cells, such as Chinese Hamster Ovary cells, and HEK 293F cells, for example.

Human constant region DNA sequences can be isolated in accordance with well known procedures from a variety of human cells, but preferably immortalized B-cells (see, Kabat op. cit. and WP87/02671). The CDR's for producing the immunoglobulins of the present invention will be similarly derived from monoclonal antibodies capable of binding to the predetermined antigen, such as IL-31, and produced by well known methods in any convenient mammalian source including, mice, rats, rabbits, or other vertebrates, capable of producing antibodies. Suitable source cells for the constant region and framework DNA sequences, and host cells for immunoglobulin expression and secretion, can be obtained from a number of sources, such as the American Type Culture Collection ("Catalogue of Cell Lines and Hybridomas," sixth edition (1988) Rockville, Md. U.S.A., which is incorporated herein by reference).

In addition to the humanized immunoglobulins specifically described herein, other "substantially homologous" modified immunoglobulins to the native sequences can be readily designed and manufactured utilizing various recombinant DNA techniques well known to those skilled in the art. A variety of different human framework regions may be used singly or in combination as a basis for the humanized immunoglobulins of the present invention. In general, modifications of the genes may be readily accomplished by a variety of well-known techniques, such as site-directed mutagenesis (see, Gillman and Smith, Gene, 8, 81-97 (1979) and S. Roberts et al., Nature, 328, 731-734 (1987), both of which are incorporated herein by reference).

The humanized antibodies of the invention include fragments as well as intact antibodies. Typically, these fragments compete with the intact antibody from which they were derived for antigen binding. The fragments typically bind with an affinity of at least $10^7$ M.$^{-1}$, and more typically $10^8$ or $10^9$ M.$^{-1}$ (i.e., within the same ranges as the intact antibody). Humanized antibody fragments include separate heavy chains, light chains Fab, Fab' F(ab')$_2$, and Fv. Fragments are produced by recombinant DNA techniques, or by enzymic or chemical separation of intact immunoglobulins.

For further details in humanizing antibodies, see European Patent Nos. EP 239,400, EP 592,106, and EP 519,596; International Publication Nos. WO 91/09967 and WO 93/17105; U.S. Pat. Nos. 5,225,539, 5,530,101, 5,565,332, 5,585,089, 5,766,886, and 6,407,213; and Padlan, 1991, Molecular Immunology 28(4/5): 489 498; Studnicka et al., 1994, Protein Engineering 7(6): 805 814; Roguska et al., 1994, PNAS 91: 969 973; Tan et al., 2002, J. Immunol. 169: 1119 25; Caldas et al., 2000, Protein Eng. 13: 353 60; Morea et al., 2000, Methods 20: 267 79; Baca et al., 1997, J. Biol. Chem. 272: 10678 84; Roguska et al., 1996, Protein Eng. 9: 895 904; Couto et al., 1995, Cancer Res. 55 (23 Supp): 5973s 5977s; Couto et al., 1995, Cancer Res. 55: 1717 22; Sandhu, 1994, Gene 150: 409 10; Pedersen et al., 1994, J. Mol. Biol. 235: 959 73; Jones et al., 1986, Nature 321: 522-525; Reichmann et al., 1988, Nature 332: 323-329; and Presta, 1992, Curr. Op. Struct. Biol. 2: 593-596.

Various techniques have been developed for the production of antibody fragments. Traditionally, these fragments were derived via proteolytic digestion of intact antibodies (see, e.g., Morimoto et al., Journal of Biochemical and Biophysical Methods 24: 107-117 (1992) and Brennan et al., Science, 229:81 (1985)). However, these fragments can now be produced directly by recombinant host cells. For example, the antibody fragments can be isolated from the antibody phage libraries discussed above. Alternatively, Fab'-SH fragments can be directly recovered from E. coli and chemically coupled to form F(ab').sub.2 fragments (Carter et al., Bio/Technology 10: 163-167 (1992)). According to another approach, F(ab').sub.2 fragments can be isolated directly from recombinant host cell culture. Other techniques for the production of antibody fragments will be apparent to the skilled practitioner. Further, examples of techniques which can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240: 1038-1040 (1988).

The present invention encompasses antibodies recombinantly fused or chemically conjugated (including both covalently and non-covalently conjugations) to a polypeptide (or portion thereof, preferably at least 10, 20 or 50 amino acids of the polypeptide) of the present invention to generate fusion proteins. Thus, the invention also pertains to immunoconjugates comprising the antibody described herein conjugated to a cytotoxic agent such as a chemotherapeutic agent, toxin (e.g. an enzymatically active toxin of bacterial, fungal, plant or animal origin, or fragments thereof), or a radioactive isotope (i.e., a radioconjugate).

The present invention encompasses antibodies recombinantly fused or chemically conjugated (including both covalently and non-covalently conjugations) to a polypeptide (or portion thereof, preferably at least 10, 20 or 50 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20 or 50 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91-99 (1994); U.S. Pat. No. 5,474,981; Gillies et al., PNAS 89:1428-1432 (1992); Fell et al., J. Immunol. 146:2446-2452 (1991), which are incorporated by reference in their entireties.

The present invention further includes compositions comprising the polypeptides of the present invention (e.g., those comprising an immunogenic or antigenic epitope) fused or conjugated to heterologous polypeptide sequences (e.g., antibody domains other than the variable regions). For example, the polypeptides of the present invention may be fused or conjugated to an antibody Fc region, or portion thereof. For example, polypeptides of the present invention (including fragments or variants thereof), may be fused with the constant domain of immunoglobulins (IgA, IgE, IgG, IgM), or portions thereof ($C_H1$, $C_{H2}$, $C_{H3}$, or any combination thereof and portions thereof, resulting in chimeric polypeptides. The antibody portion fused to a polypeptide of the present invention may comprise the constant region, hinge region, $C_{H1}$ domain, $C_{H2}$ domain, and $C_{H3}$ domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535-10539 (1991); Zheng et al., J. Immunol. 154:5590-5600 (1995); and Vil et al., Proc. Natl. Acad. Sci. USA 89:11337-11341 (1992) (said references incorporated by reference in their entireties). By way of another non-limiting example, polypeptides and/or antibodies of the present invention (including fragments or variants thereof) may be fused with albumin (including but not limited to recombinant human serum albumin or fragments or variants thereof (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)). Polypeptides and/or antibodies of the present invention (including fragments or variants thereof) may be fused to either the N- or C-terminal end of the heterologous protein (e.g., immunoglobulin Fc polypeptide or human serum albumin polypeptide). Polynucleotides encoding fusion proteins of the invention are also encompassed by the invention.

As discussed above, the polypeptides of the present invention may be fused or conjugated to the above antibody portions to increase the in vivo half life of the polypeptides or for use in immunoassays using methods known in the art. Further, the polypeptides of the present invention may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (See, e.g., EP 394,827; Traunecker et al., Nature 331:84-86 (1988)). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958-3964 (1995)). In many cases, the Fc part in a fusion protein is beneficial in therapy and diagnosis, and thus can result in, for example, improved pharmacokinetic properties. (EP A 232, 262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52-58 (1995); K. Johanson et al., J. Biol. Chem. 270:9459-9471 (1995)0. Such techniques also include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety).

Moreover, the polypeptides of the invention (e.g., antibodies or fragments thereof) can be fused to marker sequences, such as a peptide to facilitates their purification. In a further embodiment, nucleic acids encoding the polypeptides of the invention (including, but not limited to nucleic acids encoding immunogenic and/or antigenic epitopes) can also be recombined with a gene of interest as an epitope tag (e.g., the hemagglutinin tag ("HA") or flag tag) to aid in detection and purification of the expressed polypeptide. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses IL-31 binding molecules or IL-31 antagonists conjugated to a diagnostic or therapeutic agent. The IL-31 binding molecules or IL-31 antagonists can be used diagnostically to, for example, monitor the development or progression of a tumor as part of a clinical testing procedure to, e.g., determine the efficacy of a given treatment, diagnosis, detection, and/or prevention regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{111}In$ or $^{99}Tc$.

Further, IL-31 binding molecules or IL-31 antagonists may be conjugated to a therapeutic moiety such as a cytotoxin, e.g., a cytostatic or cytocidal agent, a therapeutic agent or a radioactive metal ion. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, .beta.-interferon, nerve growth factor, platelet derived growth factor, tissue plasminogen activator, a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

IL-31 binding molecules or IL-31 antagonists may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies'84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev. 62:119-58 (1982).

Alternatively, IL-31 binding molecules or IL-31 antagonists can be conjugated to a second antibody to form an antibody heteroconjugate as described by Segal in U.S. Pat. No. 4,676,980, which is incorporated herein by reference in its entirety.

An IL-31 binding molecules or IL-31 antagonists, with or without a therapeutic moiety conjugated to it, administered alone or in combination with cytotoxic factor(s) and/or cytokine(s) can be used as a therapeutic.

A variety of assays known to those skilled in the art can be utilized to detect binding of IL-31 binding molecules or IL-31 antagonists to IL-31 proteins or polypeptides. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radioimmunoassay, radioimmuno-precipitation, enzyme-linked immunosorbent assay (ELISA), dot blot or Western blot assay, inhibition or competition assay, and sandwich assay. In addition, antibodies can be screened for binding to wild-type versus mutant IL-31 protein or polypeptide.

IL-31 binding molecules or IL-31 antagonists to IL-31 may be used for tagging cells that express IL-31; for isolating IL-31 by affinity purification; for diagnostic assays for determining circulating levels of IL-31 polypeptides; for detecting or quantitating soluble IL-31 as a marker of underlying pathology or disease; in analytical methods employing FACS; for screening expression libraries; for generating anti-idiotypic antibodies; and as neutralizing antibodies or as antagonists to block IL-31 activity in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications. Moreover, antibodies to IL-31 or fragments thereof may be used in vitro to detect denatured IL-31 or fragments thereof in assays, for example, Western Blots or other assays known in the art.

The choice of the Fc domain may have implications on (i) the antibody's effector functions (FcγR binding (ADCC)/C1q binding (CDC)) and potentially associated side-effects, (ii) its pharmacokinetic properties (FcRn binding) including half-life, and (iii) possibly on immune complex clearance. The effector function(s) of the Fc domain include phagocytosis, release of inflammatory mediators, regulation of antibody production, and most importantly antibody-dependent cell-mediated cytotoxicity (ADCC) and complement dependent cytotoxicity (CDC). The degree with which any of these effector functions are induced depends on the interaction of the Fc domain with the relevant protein mediators, the Fcγ receptors and C1q, and differs depending on the IgG subclass constant regions (Fc) and their interaction with these proteins.

The Fc domain of IgG1 interacts with FcγRI, FcγRIIa, and FcγRIII on immune system effector cells. The precise role of the different Fcγ receptors remains to be elucidated but FcγRIIIA is thought to be the most important ADCC mediating receptor expressed primarily on NK cells but also monocytes and macrophages. IgG1 also binds C1q and can trigger CDC which is mediated principally by NK cells expressing FcγRIII. See Gessner, J. E., et al., The IgG Fc Receptor Family, Ann. Hematol. 1998 June: 76(6): 231-248. The IgG4 Fc domain has largely reduced binding affinity to the different Fcγ receptors and C1q, corresponding to reduced ADCC and CDC. For example, Sharma et al. examined a direct comparison of an IgG1 mAb and its IgG4 derivative, each with identical variable regions that targeted CD4. Both mAbs decreased CD4 expression at equal dose levels and had equivalent pharmacokinetic properties, but the IgG1 form showed a more potent ADCC effect. See Sharma A., et al., Comparative pharmacodynamics of keliximab and clenoliximab in transgenic mice bearing human CD4. J Pharmacol Exp Ther. 2000 April; 293(1):33-41.

The binding affinity of the effector negative IgG4 mAb is greatly reduced if not abolished when compared to other IgG isotype mAbs. However, the ability to interact with the Brambell receptor (FcRn) is retained in IgG4 thus affecting the pharmacokinetics of the IgG4 isotype mAb through an increased half-life. While IgG1 shows generally high activity towards both ADCC and CDC, IgG4 is regarded as having low to no ADCC or CDC activity.

Several examples of IgG4 isotype mAbs that are either on the market, in the clinic or at various stages of research and development. These therapeutic mAbs are developed for a variety of indications in oncology, autoimmunity & inflammation as well as in anti-viral therapy.

As reported by Aalberse et al. (See Aalberse R C, Schuurman, J. IgG4 breaking the rules, Immunology 2002, 105: 9-19), human (IgG4) exists in two molecular forms due to the heterogeneity of the inter-heavy chain disulfide bridges in the hinge region in a portion of secreted human IgG4. This heterogeneity is only revealed under denaturing, non-reducing conditions in which an HL "half antibody" is detected, a phenomenon not seen in other human IgG isotypes. Taylor report that artifactual phenomena during sample handling such as rapid disulfide scrambling and reoxidation upon exposure to reductant can contribute to the amount of half-antibody present (Taylor F R, et al., Suppression of Sodium Dodecyl Sulfate-Polyacrylamide Gel Electrophoresis Sample Preparation Artifacts for Analysis of IgG4 Half-Antibody. Analytical Biochemistry 2006, 353: 204-208). Under native conditions, noncovalent interactions ensure that the antibody is held together as the H2L2 tetramer. Though, IgG4 has been reported to hetero-dimerize with other IgG4 molecules in circulation. Analysis of the hinge sequences that connect the F[ab] and Fc portion of the antibody of human IgG heavy chains suggests that the presence of serine at residue 241 might be the cause of this heterogeneity: the IgG4 hinge region contains a Cys-Pro-Ser-Cys sequence rather than a Cys-Pro-Pro-Cys sequence as in IgG1. Changing the serine at 241 to proline (found at that position in IgG1 and IgG2) in a mouse/human chimeric heavy chain leads to the production of a homogeneous antibody and abolishes the heterogeneity. Further, the variant IgG4 has significantly extended serum half-life and shows an improved tissue distribution compared to the original chimeric IgG4.

Suitable detectable molecules may be directly or indirectly attached to the polypeptide or antibody, and include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria, toxin, saporin, Pseudomonas exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Polypeptides or antibodies may also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the polypeptide or antibody portion. For these purposes, biotin/streptavidin is an exemplary complementary/anticomplementary pair.

IL-31 binding molecules or IL-31 antagonists can also act as IL-31 "antagonists" to block IL-31 binding and signal transduction in vitro and in vivo. These IL-31 binding molecules or IL-31 antagonists would be useful for inhibiting IL-31 activity or protein-binding.

Polypeptide-toxin fusion proteins or antibody-toxin fusion proteins can be used for targeted cell or tissue inhibition or ablation (for instance, to treat cancer cells or tissues). Alternatively, if the polypeptide has multiple functional domains (i.e., an activation domain or a receptor binding domain, plus a targeting domain), a fusion protein including only the targeting domain may be suitable for directing a detectable molecule, a cytotoxic molecule or a complementary molecule to a cell or tissue type of interest. In instances where the domain only fusion protein includes a complementary molecule, the anti-complementary molecule can be conjugated to a detectable or cytotoxic molecule. Such domain-complementary molecule fusion proteins thus represent a generic targeting carrier or vehicle for cell/tissue-specific delivery of generic anti-complementary-detectable/cytotoxic molecule conjugates.

A further object of the present invention is an isolated nucleic acid molecule encoding any of the antibodies here above or below described, or a complementary strand or degenerate sequence thereof. In this regard, the term "nucleic acid molecule" encompasses all different types of nucleic acids, including without limitation deoxyribonucleic acids (e.g., DNA, cDNA, gDNA, synthetic DNA, etc.), ribonucleic acids (e.g., RNA, mRNA, etc.) and peptide nucleic acids (PNA). In a preferred embodiment, the nucleic acid molecule is a DNA molecule, such as a double-stranded DNA molecule or a cDNA molecule. The term "isolated" means nucleic acid molecules that have been identified and separated from at least one contaminant nucleic acid molecule with which it is ordinarily associated in the natural source. An isolated nucleic acid molecule is other than in the form or setting in which it is found in nature. Isolated nucleic acid molecules therefore are distinguished from the specific nucleic acid molecule as it exists in natural cells. A degenerate sequence designates any nucleotide sequence encoding the same amino acid sequence as a reference nucleotide sequence, but comprising a distinct nucleotide sequence as a result of the genetic code degeneracy.

A further object of this invention is a vector comprising DNA encoding any of the above or below described antibodies. The vector may be any cloning or expression vector, integrative or autonomously replicating, functional in any prokaryotic or eukaryotic cell. In particular, the vector may be a plasmid, cosmid, virus, phage, episome, artificial chromosome, and the like. The vector may comprise regulatory elements, such as a promoter, terminator, enhancer, selection marker, origin of replication, etc. Specific examples of such vectors include prokaryotic plasmids, such as pBR, pUC or pcDNA plasmids; viral vectors, including retroviral, adenoviral or AAV vectors; bacteriophages; baculoviruses; BAC or YAC, etc., as will be discussed below. The appropriate nucleic acid sequence may be inserted into the vector by a variety of procedures. In general, DNA is inserted into an appropriate restriction endonuclease site(s) using techniques known in the art. Construction of suitable vectors containing one or more of these components employs standard ligation techniques which are known to the skilled artisan.

A further aspect of the present invention is a recombinant host cell, wherein said cell comprises a nucleic acid molecule or a vector as defined above. The host cell may be a prokaryotic or eukaryotic cell. Examples of prokaryotic cells include bacteria, such as *E. coli*. Examples of eucaryotic cells are yeast cells, plant cells, mammalian cells and insect cells including any primary cell culture or established cell line (e.g., 3T3, Véro, HEK293, TN5, etc.). Suitable host cells for the expression of glycosylated proteins are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., J. Gen Virol., 36:59 (1977)); Chinese hamster ovary cells/-DHFR (CHO, Urlaub and Chasin, Proc. Natl, Acad. Sci. USA, 77:4216 (1980)); mouse sertoli cells (TM4, Mather, Biol. Reprod., 23:243-251 (1980)); human lung cells (W138, ATCC CCL 75); human liver cells (Hep G2, HB 8065); and mouse mammary tumor (MMT 060562, ATCC CCL51). Particularly preferred mammalian cells of the present invention are CHO cells.

As disclosed here above, the antibodies of the present invention may be produced by any technique known per se in the art, such as by recombinant technologies, chemical synthesis, cloning, ligations, or combinations thereof. In a particular embodiment, the antibodies are produced by recombinant technologies, e.g., by expression of a corresponding nucleic acid in a suitable host cell. Another object of this invention is therefore a method of producing an antibody of the present invention, the method comprising culturing a recombinant host cell of the invention under conditions allowing expression of the nucleic acid molecule, and recovering the polypeptide produced. The polypeptide produced may be glycosylated or not, or may contain other post-translational modifications depending on the host cell type used. Many books and reviews provide teachings on how to clone and produce recombinant proteins using vectors and prokaryotic or eukaryotic host cells, such as some titles in the series "A Practical Approach" published by Oxford University Press ("DNA Cloning 2: Expression Systems", 1995; "DNA Cloning 4: Mammalian Systems", 1996; "Protein Expression", 1999; "Protein Purification Techniques", 2001).

The vectors to be used in the method of producing an antibody according to the present invention can be episomal or non-/homologously integrating vectors, which can be introduced into the appropriate host cells by any suitable means (transformation, transfection, conjugation, protoplast fusion, electroporation, calcium phosphate-precipitation, direct microinjection, etc.). Factors of importance in selecting a particular plasmid, viral or retroviral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species. The vectors should allow the expression of the polypeptide or fusion proteins of the invention in prokaryotic or eukaryotic host cells, under the control of appropriate transcriptional initiation/termination regulatory sequences, which are chosen to be constitutively active or inducible in said cell. A cell line substantially enriched in such cells can be then isolated to provide a stable cell line.

Host cells are transfected or transformed with expression or cloning vectors described herein for protein production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in Mammalian Cell Biotechnology: a Practical Approach, M. Butler, ed. (IRL Press, 1991) and Sambrook et al., supra.

Preferred cells to be used in the present invention are eukaryotic host cells, e.g. mammalian cells, such as human, monkey, mouse, and Chinese Hamster Ovary (CHO) cells, because they provide post-translational modifications to protein molecules, including correct folding or glycosylation at correct sites. Examples of suitable mammalian host cells include African green monkey kidney cells (Vero; ATCC CRL 1587), human embryonic kidney cells (293-HEK; ATCC CRL 1573), baby hamster kidney cells (BHK-21, BHK-570; ATCC CRL 8544, ATCC CRL 10314), canine kidney cells (MDCK; ATCC CCL 34), Chinese hamster ovary cells (CHO-K1; ATCC CCL61; CHO DG44 (Chasin et al., Som. Cell. Molec. Genet. 12:555, 1986)), rat pituitary cells (GH1; ATCC CCL82), HeLa S3 cells (ATCC CCL2.2), rat hepatoma cells (H-4-II-E; ATCC CRL 1548), SV40-transformed monkey kidney cells (COS-1; ATCC CRL 1650), Bowes melanoma and human hepatocellular carcinoma (for example Hep G2), murine embryonic cells (NIH-3T3; ATCC CRL 1658) and a number of other cell lines. Alternative eukaryotic host cells are yeast cells (e.g., *Saccharomyces, Kluyveromyces*, etc.) transformed with yeast expression vectors. Also yeast cells can carry out post-translational peptide modifications including glycosylation. A number of recombinant DNA strategies exist which utilize strong promoter sequences and high copy number of plasmids that can be utilized for production of the desired proteins in yeast. Yeast cells recognize leader sequences in cloned mammalian gene products and secrete polypeptides bearing leader sequences (i.e., pre-peptides).

For long-term, high-yield production of a recombinant polypeptide, stable expression is preferred. For example, cell lines which stably express the polypeptide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells that successfully express the introduced sequences. Resistant clones of stably transformed cells may be proliferated using tissue culture techniques appropriate to the cell type. A cell line substantially enriched in such cells can be then isolated to provide a stable cell line.

A particularly preferred method of high-yield production of a recombinant polypeptide of the present invention is through the use of dihydrofolate reductase (DHFR) amplification in DHFR-deficient CHO cells, by the use of successively increasing levels of methotrexate as described in U.S. Pat. No. 4,889,803. The polypeptide obtained may be in a glycosylated form.

Antibodies disclosed herein can also be expressed in other eukaryotic cells, such as avian, fungal, insect, yeast, or plant cells. The baculovirus system provides an efficient means to introduce cloned genes into insect cells. The materials for baculovirus/insect cell expression systems are commercially available in kit form from, inter alia, Invitrogen.

In addition to recombinant DNA technologies, the antibodies of this invention may be prepared by chemical synthesis technologies. Examples of chemical synthesis technologies are solid phase synthesis and liquid phase synthesis. As a solid phase synthesis, for example, the amino acid corresponding to the carboxy-terminus of the polypeptide to be synthesised is bound to a support which is insoluble in organic solvents and, by alternate repetition of reactions (e.g., by sequential condensation of amino acids with their amino groups and side chain functional groups protected with appropriate protective groups), the polypeptide chain is extended. Solid phase synthesis methods are largely classified by the tBoc method and the Fmoc method, depending on the type of protective group used. Totally synthetic proteins are disclosed in the literature (Brown A et al., 1996).

The antibodies of the present invention can be produced, formulated, administered, or generically used in other alternative forms that can be preferred according to the desired method of use and/or production. The proteins of the invention can be post-translationally modified, for example by glycosylation. The polypeptides or proteins of the invention can be provided in isolated (or purified) biologically active form, or as precursors, derivatives and/or salts thereof.

In another embodiment, IL-31 binding molecules or IL-31 antagonists fusion proteins can be used for in vivo killing of target tissues where the IL-31 receptors are expressed) (See, generally, Hornick et al., *Blood* 89:4437-47, 1997). The described fusion proteins enable targeting of the IL-31 binding molecules or IL-31 antagonists a desired site of action, thereby providing an elevated local concentration of IL-31 binding molecules or IL-31 antagonists, targeting an undesirable cell or tissue (i.e., a tumor or a leukemia), and the fused cytokine mediated improved target cell lysis by effector cells. Suitable cytokines for this purpose include interleukin 2 and granulocyte-macrophage colony-stimulating factor (GM-CSF), for instance.

The IL-31 binding molecules or IL-31 antagonists of the present invention can be measured for their ability to inhibit, block, or neutralize the IL-31 ligand as determined by various in vivo models known in the art and described herein, including but not limited to the NC/Nga model, the Ova epicutaneous model, the chronic hypersensitivity model, and the chronic hapten model.

Both skin-homing T cells and epidermal keratinocytes have been implicated in the pathology of skin diseases in humans. IL-31 mRNA and protein expression is restricted to the skin-homing CLA+ T cell population in humans. See U.S. patent application Ser. No. 11/353,427, filed Feb. 14, 2006, incorporated herein by reference. As such, an antagonist to IL-31, including an antibody or receptor antagonist will be useful in treating skin and epidermal diseases which have expression of CLA+ T cells. Such diseases include, for example, atopic dermatitis, contact dermatitis, drug-induced allergic reactions, skin-tropic viruses and viral associated pruritis, vitiligo, cutaneous T cell lymphoma, alopecia aerata, acne rosacea, acne vulgaris, prurigo nodularis, and bullous pemphigoid. Chemokine markers such as TARC and MDC are useful to measure the effect of a neutralizing monoclonal antibody to IL-31. The inhibitory effects of treatment with IL-31 binding molecules or IL-31 antagonists described herein can be measured by monitoring the levels of TARC and MDC.

Contact Dermatitis

Allergic contact dermatitis is defined as a T cell mediated immune reaction to an antigen that comes into contact with the skin. The CLA+ T cell population is considered to be involved in the initiation of dermatitis since allergen dependent T cell responses are largely confined to the CLA+ population of cells (See Santamaria-Babi, L. F., et al., *J Exp Med:* 181, 1935, (1995)). Recent data has found that only memory (CD45RO+) CD4+ CLA+ and not CD8+ T cells proliferate and produce both type-1 (IFN-) and type-2 (IL-5) cytokines in response to nickel, a common contact hypersensitivity allergen. Furthermore, cells expressing CLA in combination with CD4, CD45RO (memory) or CD69 are increased after nickel-specific stimulation and express the chemokine receptors CXCR3, CCR4, CCR10 but not CCR6. See Moed H., et al., *Br J Dermatol:* 51, 32, (2004).

In animal models, it has been demonstrated that allergic contact dermatitis is T-cell dependent and that the allergic-responsive T cells migrate to the site of allergen application. See generally: Engeman T. M., et al., *J Immunol:* 164, 5207, (2000); Ferguson T. A. & Kupper T. S. *J Immunol:* 150, 1172, (1993); and Gorbachev A. V. & Fairchild R. L. *Crit. Rev Immunol:* 21, 451 (2001). Since CLA+ T cells produce IL-31 and IL-31 stimulation of skin keratinocytes can induce pro-inflammatory chemokines, such as TARC and MDC, IL-31 may be involved in the pathophysiology of contact dermatitis. By using a neutralizing IL-31 antibody in a mouse model of contact hypersensitivity. See Example 5.

Thus, neutralization of IL-31 by the IL-31 binding molecules or IL-31 antagonists described herein may be used to improve clinical outcome of Contat Hypersenstivity by inhibition, reduction, neutralization, prevention or blocking the inflammation and/or scratching associated with disease.

Atopic Dermatitis

Atopic dermatitis (AD) is a chronically relapsing inflammatory skin disease with a dramatically increasing incidence over the last decades. Clinically AD is characterized by highly pruritic often excoriated plaques and papules that show a chronic relapsing course. The diagnosis of AD is mostly based on major and minor clinical findings. See Hanifin J. M., *Arch Dermatol:* 135, 1551 (1999). Histopathology reveals spongiosis, hyper and focal parakeratosis in acute lesions, whereas marked epidermal hyperplasia with hyper and parakeratosis, acanthosis/hypergranulosis and perivascular infiltration of the dermis with lymphocytes and abundant mast cells are the hallmarks of chromic lesions.

T cells play a central role in the initiation of local immune responses in tissues and evidence suggests that skin-infiltrating T cells in particular, may play a key role in the initiation and maintenance of disregulated immune responses in the skin. Approximately 90% of infiltrating T cells in cutaneous inflammatory sites express the cutaneous lymphocyte-associated Ag (CLA+) which binds E-selectin, an inducible adhesion molecule on endothelium (reviewed in Santamaria-Babi L. F., et al., *Eur J Dermatol:* 14, 13, (2004)). A significant increase in circulating CLA+ T cells among AD patients compared with control individuals has been documented (See Teraki Y., et al., *Br J Dermatol:* 143, 373 (2000), while others have demonstrated that memory CLA+ T cells from AD patients preferentially respond to allergen extract compared to the CLA-population (See Santamaria-Babi, L. F., et al., *J Exp Med:* 181, 1935, (1995)). In humans, the pathogenesis of atopic disorders of the skin have been associated with increases in CLA+ T cells that express increased levels of Th-2-type cytokines like IL-5 and IL-13 9, 10. See Akdis M., et al., *Eur J Immunol:* 30, 3533 (2000); and Hamid Q., et al., *J Allergy Clin Immunol:* 98, 225 (1996).

NC/Nga Mice spontaneously develop AD-like lesions that parallel human AD in many aspects, including clinical course and signs, histophathology and immunopathology when housed in non-specified pathogen-free (non-SPF) conditions at around 6-8 weeks of age. In contrast, NC/Nga mice kept under SPF conditions do not develop skin lesions. However, onset of spontaneous skin lesions and scratching behaviour can be synchronized in NC/Nga mice housed in a SPF facility by weekly intradermal injection of crude dust mite antigen. See Matsuoka H., et al., *Allergy:* 58, 139 (2003). Therefore, the development of AD in NC/Nga is a useful model for the evaluation of novel therapeutics for the treatment of AD.

In addition to the NC/Nga model of spontaneous AD, epicutaneous sensitization of mice using OVA can also be used as a model to induce antigen-dependent epidermal and dermal thickening with a mononuclear infiltrate in skin of sensitized mice. This usually coincides with elevated serum levels of total and specific IgE, however no skin barrier dysfunction or pruritus normally occurs in this model. See Spergel J. M., et al., *J Clin Invest,* 101: 1614, (1998). This protocol can be modified in order to induce skin barrier disregulation and pruritus by sensitizing DO11.10 OVA TCR transgenic mice with OVA. Increasing the number of antigen-specific T cells that could recognize the sensitizing antigen may increase the level of inflammation in the skin to induce visible scratching behaviour and lichenification/scaling of the skin.

Both the NC/Nga spontaneous AD model and the OVA epicutaneous DO11.10 model are used to evaluate the ability of the IL-31 binding molecules or IL-31 antagonists described herein to inhibit, reduce, or neutralize the effects of IL-31. Administration of IL-31 binding molecules or IL-31 antagonists can result in a reduction in scratching that can be effective in treating pruritic diseases including, but not limited to, atopic dermatitis, prurigo nodularis, and eczema, since cessation of scratching will stop progression of dermatitis, the development of which is dependent on scratching.

Additional models to measure the inhibitory effects of the IL-31 binding molecules or IL-31 antagonists described herein are described by Umeuchi, H. et al., European Journal of Pharmacology, 518: 133-139, 2005; and by Yoo, J. et al., J. Experimental Medicine, 202:541-549, 2005.

Thus, neutralization of IL-31 by the IL-31 binding molecules or IL-31 antagonists described herein may be used to improve clinical outcome of dermatitis and pruritic diseases including atopic dermatitis, prurigo nodularis, and eczema by inhibition, reduction, prevention or blocking the inflammation and/or scratching associated with disease.

Drug-Induced Delayed Tape Cutaneous Allergic Reactions

Drug-induced delayed type cutaneous allergic reactions are very heterogeneous and may mirror many distinct pathophysiological events. See Brockow K., et al., *Allergy:* 57, 45 (2002). Immunological mechanisms involved in these reactions have been shown as either antibody or cell mediated. In immediate drug allergy an IgE-mediated antibody reaction can be demonstrated by a positive skin prick and/or intradermal test after 20 min, whereas non-immediate reactions to drugs can occur more than one hour after last drug intake and are often T-cell mediated. Non-immediate T-cell mediated delayed type reactions can occur in patients with adverse drug reactions to penicillins for example. Proliferative T cell responses to penicillins have been shown to be restricted to the memory (CD45RO+) CLA+ subpopulation of T cells from penicillin allergic patients whereas the CD45RO+ CLA- subset shows no proliferative response. See Blanca M., Leyva L., et al., *Blood Cells Mol Dis:* 31, 75 (2003). Delayed-type hypersensitivity (DTH) reactions can be artificially reproduced in mice, allowing assessment of factors that may be involved in the initiation and perpetuation of the DTH response. Il-31 neutralizing IL-31 binding molecules or IL-31 antagonists could be effective in delayed type hypersensitivity reactions.

Toxic epidermal necrolysis (TEN) is a very rare but extremely severe drug reaction characterized by widespread apoptosis of epidermis with extensive blisters. Studies have shown that lymphocytes infiltrating the blister are CLA+ T cells and can exhibit cytotoxicity towards epidermal keratinocytes. See Leyva L., et al., *J Allergy Clin Immunol:* 105, 157 (2000); and Nassif A., Bensussan A., et al., *J Allergy Clin Immunol:* 114, 1209 2004). A transgenic mouse system, whereby OVA is expressed under the control of the keratin-5 (K5) promoter in the epidermal and hair follicular keratinocytes of mice, has been generated to establish an animal model for TEN. OVA specific CD8+ T cells, when adoptively transferred into K5-OVA mice, undergo activation and proliferation in the skin-draining lymph nodes and target the skin of K5-OVA mice, resulting in development of skin lesions that are reminiscent of TEN. See Azukizawa H., et al., *Eur J Immunol:* 33, 1879 (2003).

Thus, neutralization of IL-31 by the IL-31 binding molecules or IL-31 antagonists described herein may be used to improve clinical outcome of TEN by inhibition, reduction, prevention or blocking the inflammation and/or scratching associated with disease.

Bullous Pemphigoid

Bullous pemphigoid is a subepidermal disorder which manifests as subepidermal blisters with a dermal infiltrate of neutrophils and eosinophils. Diagnosis is characterized by the presence of antigen-specific antibodies against specific adhesion proteins of the epidermis and dermal-epidermal junction. See Jordon R. E., et al., *JAMA:* 200, 751 (1967). Studies analyzing the role of T cells in the pathogenesis of bullous pemphigoid by analysis of PBL and skin blister T cells have found a predominance of CLA+ T cells expressing increased levels of Th2-cytokines like IL-4 and IL-13. See Teraki Y., et al., *J Invest Dermatol:* 117, 1097 (2001). In bullous pemphigoid patients following therapy with systemic corticosteroids, the frequency of $CLA^+$, but not CLA-, interleukin-13-producing cells is significantly decreased.

Decreases in CLA+ cells following corticosteroid treatment is associated with clinical improvement. See Teraki, ibid.

Thus, neutralization of IL-31 by the IL-31 binding molecules or IL-31 antagonists described herein may be used to improve clinical outcome of bullous pemphigoid by inhibition, reduction, prevention or blocking the inflammation and/or scratching associated with disease.

Alopecia Greata

Alopecia greata (AA) is regarded as a tissue-restricted autoimmune disease of hair follicles in which follicular activity is arrested because of the continued activity of lymphocytic infiltrates. AA results in patches of complete hair loss anywhere on the body, though actual loss of hair follicles does not occur, even in hairless lesions. Although clinical signs of inflammation are absent, skin biopsies from sites of active disease show perifollicular lymphocytic inflammation of primarily CD4+ cells, along with a CD8+ intrafollicular infiltrate. See Kalish R. S. & Gilhar A. *J Invest Dermatol Symp Proc:* 8, 164 (2003).

Studies have shown that scalp skin infiltrating CD4+ or CD8+ lymphocytes express CLA and, in peripheral blood of individuals with AA, the percent of CLA+ CD4+ or CD8+ lymphocytes is significantly higher than that of normal controls. Furthermore, patients with severe or progressive AA show a much higher CLA-positively compared to patients recovering from the disease and a decrease in percent CLA+ cells parallels a good clinical course. See Yano S., et al., *Acta Derm Venereol:* 82, 82 (2002). These studies therefore suggest that CLA+ lymphocytes may play an important role in AA. Xenograft models have demonstrated that activated T cells are likely to play a role in the pathogenesis of AA. Lesional scalp from AA patients grafted onto nude mice regrows hair coincident with a loss of infiltrating lymphocytes from the graft and, transfer of activated lesional T cells to SCID mice can transfer hair loss to human scalp explants on SCID mice. See Kalish R. S. & Gilhar A. *J Investig Dermatol Symp Proc:* 8, 164 (2003).

A variety of immunomodulating therapies are part of the usual treatment for this disorder however none of these treatments have been consistent in their efficacy. See Tang L., et al., *J Invest Dermatol:* 120, 400 (2003); Tang L., et al., (2004); and Tang L., et al., *J Am Acad Dermatol:* 49, 1013 (2003). Nevertheless, their uses in valid animal models provide a tool to dissect out molecular mechanisms of therapeutic effects. See Shapiro J., et al., *J Investig Dermatol Symp Proc:* 4, 239 (1999); Tang L., et al., Old wine in new bottles: reviving old therapies for alopecia greata using rodent models (2003); and Verma D. D., et al., *Eur J Dermatol:* 14, 332 (2004).

Thus, neutralization of IL-31 by the IL-31 binding molecules or IL-31 antagonists described herein may be used to improve clinical outcome of alopecia greata by inhibition, reduction, prevention or blocking the inflammation and/or scratching associated with disease.

Acne Rosacea/Acne Vulgaris

Acne vulgaris, a disorder of the pilosebaceous apparatus, is the most common skin problem of adolescence. Abnormalities in follicular keratinization are thought to produce the acne lesion. Acne rosacea is differentiated from acne vulagaris by the presence of red papules, pustules, cysts and extensive telangiectasias, but the absence of comedones (white heads). Increased sebum excretion from sebaceous glands is a major factor in the pathophysiology of acne vulgarism. Other sebaceous gland functions are also associated with the development of acne, including sebaceous proinflammatory lipids; different cytokines produced locally; periglandular peptides and neuropeptides, such as corticotrophin-releasing hormone, which is produced by sebocytes; and substance P, which is expressed in the nerve endings at the vicinity of healthy-looking glands of acne patients. See Zouboulis C. C. *Clin Dermatol:* 22, 360 (2004).

Although the pathophysiology of acne vulgaris and acne rosacea remains unknown, clinical observations and histopathologic studies suggest that inflammation of the pilosebaceous follicle may be central to the pathogenesis of rosacea and acne vulgarism Early studies on analysis of T cell subsets infiltrating rosacea legions indicated that the majority of T cells expressed CD4. See Rufli T. & Buchner S. A. *Dermatologica:* 169, 1 (1984).

CD4+ T cells produce IL-31 and IHC analysis of skin for IL-31 expression suggests that IL-31 is expressed in sebaceous and sweat glands. IL-31 stimulation of epidermal keratinocytes induces expression of chemokines which likely results in cellular infiltration suggesting that IL-31 may contribute to the pro-inflammatory response in skin. See Dillon S. R., et al., *Nat Immunol:* 5, 752 (2004). IL-31 may therefore contribute to the pathophysiology of acne rosacea and acne vulgaris.

Thus, neutralization of IL-31 by the IL-31 binding molecules or IL-31 antagonists described herein may be used to improve clinical outcome of acne vulgaris by inhibition, reduction, prevention or blocking the inflammation and/or scratching associated with disease.

Prurigo Nodularis

Prurigo nodularis is an eruption of lichenified or excoriated nodules caused by intractable pruritus that is difficult to treat. While chronic rubbing results in lichenification, and scratching in linear excoriations, individuals who pick and gouge at their itchy, irritated skin tend to produce markedly thickened papules known as prurigo nodules. Although prurigo nodularis is not specific to atopic dermatitis, many patients with these nodules also have an atopic reaction, which manifests as allergic rhinitis, asthma, or food allergy. T cells represent the majority of infiltrating cells in prurigo lesions and these lesions often represents the most pruritic skin lesion in atopy patients.

Topical treatment of prurigo nodularis with capsaicin, an anti-pruritic alkaloid that interferes with the perception of pruritics and pain by depletion of neuropeptides like substance P in small sensory cutaneous nerves, has proven to be an effective and safe regimen resulting in clearing of the skin lesions. See Stander S., et al., *J Am Acad Dermatol:* 44, 471 (2001). Studies of the itch response in NC/Nga mice using capsaicin treatment showed that the spontaneous development of dermatitis lesions was almost completely prevented. Furthermore, the elevation of serum IgE levels was significantly suppressed and infiltrating eosinophils and mast cell numbers in lesional skin of capsaicin treated mice were reduced. See Mihara K., et al., *Br J Dermatol:* 151, 335 (2004). The observations from this group suggest that scratching behaviour might contribute to the development of dermatitis by enhancing various immunological responses, therefore implying that prevention of the itch sensation and/or itch-associated scratching behaviour might be an effective treatment for AD. See Mihara K., et al., *Br J Dermatol:* 151, 335 (2004). Thus, the anti-11-31 antibodies described herein will be useful in minimizing the effects of AD, prurigo nodularis, and other pruritic diseases as they are shown herein to reduce the amount of scratching in NC/Nga mice.

Chronic delivery of IL-31 induces pruritis and alopecia in mice followed by the development of skin lesions resembling dermatitis suggesting that IL-31 may induce itching. See See Dillon S. R., et al., *Nat Immunol:* 5, 752 (2004). The involvement of IL-31 in induction of the itch response by two methods (i) capsaicin treatment of IL-31-treated mice and (ii)

IL-31 treatment of Tac1 knockout mice, which have significantly reduced nociceptive pain responses because of lack of expression of neuropeptides is tested in Example 10. In addition, whether neutralization of IL-31 in IL-31 treated mice with IL-31 binding molecules or IL-31 antagonists could prevent pruritis and alopecia is tested in Example 12.

Thus, neutralization of IL-31 by the IL-31 binding molecules or IL-31 antagonists described herein may be used to improve clinical outcome of prurigo nodularis by inhibition, reduction, prevention or blocking the inflammation and/or scratching associated with disease.

Skin-Tropic Viruses and Viral Associated pruritis

Herpes Simplex Virus (HSV)-specific CD8+ T cells in the peripheral blood and HSV-specific CD8+ T cells recovered from herpes lesions express high levels of CLA where as non-skin-tropic herpes virus-specific CD8+ T cells lack CLA expression. See Koelle D. M., et al., *J Clin Invest:* 110, 537 (2002). HSV-2 reactive CD4+ T lymphocytes also express CLA, but at levels lower than those previously observed for CD8+ T lymphocytes. See Gonzalez J. C., et al., *J Infect Dis:* 191, 243 (2005). Pruritis has also been associated with herpes viral infections (See Hung K. Y., et al., *Blood Purif* 16, 147 (1998). though other viral diseases, like HIV, have also been associated with pruritic skin lesions. Severe, intractable pruritus, often associated with erythematopapular skin lesions and hypereosinophilia, is a condition observed in some non-atopic, HIV-infected patients 36. See Singh F. & Rudikoff D, *Am J Clin Dermatol;* 4, 177 (2003); and Milazzo F., Piconi S., et al., *Allergy:* 54, 266 (1999).

The association of skin-tropic viruses with pruritis and CLA+ T cells suggests that IL-31 producing T cells may be involved in the pathophysiology of viral infections.

Thus, neutralization of IL-31 by the IL-31 binding molecules or IL-31 antagonists described herein may be used to improve clinical outcome of pruritis associatd with skin-tropic viruses by inhibition, reduction, prevention or blocking the inflammation and/or scratching associated with disease.

IL-31 involvement in the induction of itch response, and its reduction, blocking, inhibition or neutralization by the IL-31 binding molecules described herein, can be measured in a number of ways.

Method I (Capsaicin Treatment of IL-31 Treated Mice):

Ten week old BALB/c animals (CRL) are anaesthetized and injected with a long-lasting analgesic agent, bupranorphine hydrochloride, subcutaneously at 0.1 mg/kg before injection of 0.25 ml of 4 mg/ml solution of capsaicin in 10% ethanol+10% Tween-80 in saline subcutaneously into scruff of neck. Animals are kept anaesthetized for at least 30 min following neurotoxin treatment. Forty-eight hours later, 14-day osmotic pumps are implanted subcutaneously for continuous delivery of 20 ug/day of IL-31 for 14 days. Mice are monitored daily for 6 days for alopecia and pruritis using the following criteria: 0=no scratching, animal appears normal, 1=thinning of coat in small areas, scratching noted, 2=minor hair loss (small patches), scratching, 3=moderate hair loss, scratching, and 4=severe hair loss, excessive scratching. When this experiment was performed the results demonstrated that while non-capsaicin-treated mice showed a mean scratch/hairloss score of 2.625 following three days of IL-31 delivery, capsaicin-treated mice showed a significantly lower score of 1. Thus mice treated with capsaicin prior to IL-31 delivery showed both a delay in incidence of scratching and hairloss and a lower score in the intensity of scratching and hairloss over the six days of the experiment. These data suggest that IL-31 does induce some neuronal component that contributes to the alopecia and pruritis induced by IL-31. Therefore, neutralization of IL-31 by IL-31 binding molecules or IL-31 antagonists may decrease the incidence and intensity of itch, and therefore dermatitis, in patients suffering from skin disorders that involve itch.

Method II:

Mice that are homozygous null for the Tac1 gene express no detectable substance P or neurokinin A. These mice have significantly reduced nociceptive pain responses to moderate to intense stimuli and are therefore a useful tool for studying the contribution of tachykinin peptides to pain/itch processing and inflammatory disease states. Twelve week old, Tac1 knockout mice were implanted with 14-day osmotic pumps delivering 1 ug/day of IL-31 protein and observed daily for alopecia and pruritis using the following criteria: 0=no scratching, animal appears normal, 1=thinning of coat in small areas, scratching noted, 2=minor hair loss (small patches), scratching, 3=moderate hair loss, scratching, and 4=severe hair loss, excessive scratching.

Results of this study show that Tac1 deficient mice were less susceptible to IL-31 induced scratching/hairloss compared to wildtype control mice. While 100% (10/10) of wildtype mice had developed evidence of scratching and hairloss by day 6 of IL-31 treatment, only 33.3% (2/6) Tac1 deficient mice were showing signs of scratching and hairloss at the same time-point. These data show that IL-31 induces a neuronal component that contributes to the scratch/hairloss phenotype in IL-31-treated mice and neutralization of IL-31 by IL-31 binding molecules or IL-31 antagonists may decrease the incidence and intensity of scratching in the context of dermatitis.

Methods III (Administration of IL-31 Neutralizing Antibody):

Normal female BALB/c mice (CRL) approximately 8 to 12 weeks old were implanted subcutaneously with 14-day osmotic pumps (Alzet, #2002) delivering 1 ug/day mIL-31. Groups of mice received intraperitoneal (i.p.) injections of rat anti-mouse IL-31 monoclonal antibody 10 mg/kg (200 ug/mouse) twice weekly starting 1 week prior to IL-31 delivery. Control groups of mice received i.p. injections of vehicle (PBS/0.1% BSA) with the identical dosing schedules. Mice were scored daily for alopecia and pruritis using the following criteria: 0=no scratching, animal appears normal, 1=thinning of coat in small areas, scratching noted, 2=minor hair loss (small patches), scratching, 3=moderate hair loss, scratching, and 4=severe hair loss, excessive scratching.

In all experiments, mice treated with rat anti-mIL-31 mAb had a delay in onset of symptoms of approximately 5 to 7 days and a lower overall score for alopecia and pruritis. All groups of mAb treated mice (regardless of dose frequency or concentration) developed alopecia and pruritis similar to control mice by 13 day of the study. These data suggest that neutralization of IL-31 by IL-31 binding molecules or IL-31 antagonists can delay the onset of the scratch/hairloss response induced by IL-31. The effects of IL-31 binding molecules or IL-31 antagonists are measured by inhibition of scratching, itching, dermatitis, a reduction in IL-31RA expression in kerotinocytes, and/or a reduction in score for alopecia and pruritis.

Inflammation is a protective response by an organism to fend off an invading agent. Inflammation is a cascading event that involves many cellular and humoral mediators. On one hand, suppression of inflammatory responses can leave a host immunocompromised; however, if left unchecked, inflammation can lead to serious complications including chronic inflammatory diseases (e.g., rheumatoid arthritis, multiple sclerosis, inflammatory bowel disease and the like), septic shock and multiple organ failure. Importantly, these diverse disease states share common inflammatory mediators. The collective diseases that are characterized by inflammation have a large impact on human morbidity and mortality. Therefore it is clear that anti-inflammatory antibodies and binding polypeptides, such as anti-IL-31 antibodies and binding polypeptides described herein, could have crucial therapeutic potential for a vast number of human and animal diseases, from asthma and allergy to autoimmunity and septic shock. As such, use of anti-inflammatory anti IL-31 antibodies and binding polypeptides described herein can be used therapeutically as IL-31 antagonists described herein, particularly in diseases such as arthritis, endotoxemia, inflammatory bowel disease, psoriasis, related disease and the like.

1. Arthritis

Arthritis, including osteoarthritis, rheumatoid arthritis, arthritic joints as a result of injury, and the like, are common inflammatory conditions which would benefit from the therapeutic use of anti-inflammatory antibodies and binding polypeptides, such as anti-IL-31 antibodies and binding polypeptides of the present invention. For Example, rheumatoid arthritis (RA) is a systemic disease that affects the entire body and is one of the most common forms of arthritis. It is characterized by the inflammation of the membrane lining the joint, which causes pain, stiffness, warmth, redness and swelling. Inflammatory cells release enzymes that may digest bone and cartilage. As a result of rheumatoid arthritis, the inflamed joint lining, the synovium, can invade and damage bone and cartilage leading to joint deterioration and severe pain amongst other physiologic effects. The involved joint can lose its shape and alignment, resulting in pain and loss of movement.

Rheumatoid arthritis (RA) is an immune-mediated disease particularly characterized by inflammation and subsequent tissue damage leading to severe disability and increased mortality. A variety of cytokines are produced locally in the rheumatoid joints. Numerous studies have demonstrated that IL-1 and TNF-alpha, two prototypic pro-inflammatory cytokines, play an important role in the mechanisms involved in synovial inflammation and in progressive joint destruction. Indeed, the administration of TNF-alpha and IL-1 inhibitors in patients with RA has led to a dramatic improvement of clinical and biological signs of inflammation and a reduction of radiological signs of bone erosion and cartilage destruction. However, despite these encouraging results, a significant percentage of patients do not respond to these agents, suggesting that other mediators are also involved in the pathophysiology of arthritis (Gabay, Expert. Opin. Biol. Ther. 2(2): 135-149, 2002). One of those mediators could be IL-31, and as such a molecule that binds or inhibits IL-31, such as anti IL-31 antibodies or binding partners, could serve as a valuable therapeutic to reduce inflammation in rheumatoid arthritis, and other arthritic diseases.

There are several animal models for rheumatoid arthritis known in the art. For example, in the collagen-induced arthritis (CIA) model, mice develop chronic inflammatory arthritis that closely resembles human rheumatoid arthritis. Since CIA shares similar immunological and pathological features with RA, this makes it an ideal model for screening potential human anti-inflammatory compounds. The CIA model is a well-known model in mice that depends on both an immune response, and an inflammatory response, in order to occur. The immune response comprises the interaction of B-cells and CD4+ T-cells in response to collagen, which is given as antigen, and leads to the production of anti-collagen antibodies. The inflammatory phase is the result of tissue responses from mediators of inflammation, as a consequence of some of these antibodies cross-reacting to the mouse's native collagen and activating the complement cascade. An advantage in using the CIA model is that the basic mechanisms of pathogenesis are known. The relevant T-cell and B-cell epitopes on type II collagen have been identified, and various immunological (e.g., delayed-type hypersensitivity and anti-collagen antibody) and inflammatory (e.g., cytokines, chemokines, and matrix-degrading enzymes) parameters relating to immune-mediated arthritis have been determined, and can thus be used to assess test compound efficacy in the CIA model (Wooley, Curr. Opin. Rheum. 3:407-20, 1999; Williams et al., Immunol. 89:9784-788, 1992; Myers et al., Life Sci. 61:1861-78, 1997; and Wang et al., Immunol. 92:8955-959, 1995).

The administration of soluble IL-31RA comprising polypeptides (including heterodimeric and multimeric receptors described herein), such as IL-31RA-Fc4 or other IL-31RA soluble and fusion proteins to these CIA model mice can be used to evaluate the use of IL-31RA to ameliorate symptoms and alter the course of disease. As a molecule that modulates immune and inflammatory response, IL-31, may induce production of SAA, which is implicated in the pathogenesis of rheumatoid arthritis, IL-31 binding molecules or IL-31 antagonists may reduce SAA activity in vitro and in vivo, the systemic or local administration of IL-31 binding molecules or IL-31 antagonists can potentially suppress the inflammatory response in RA.

2. Endotoxemia

Endotoxemia is a severe condition commonly resulting from infectious agents such as bacteria and other infectious disease agents, sepsis, toxic shock syndrome, or in immunocompromised patients subjected to opportunistic infections, and the like. Therapeutically useful of anti-inflammatory antibodies and binding polypeptides, such as anti-IL-31 antibodies and binding polypeptides of the present invention, could aid in preventing and treating endotoxemia in humans and animals. Other potential therapeutics include IL-31RA polypeptides, soluble heterodimeric and multimeric receptor polypeptides, or anti IL-31 antibodies or binding partners of the present invention, and the like, could serve as a valuable therapeutic to reduce inflammation and pathological effects in endotoxemia.

Lipopolysaccharide (LPS) induced endotoxemia engages many of the proinflammatory mediators that produce pathological effects in the infectious diseases and LPS induced endotoxemia in rodents is a widely used and acceptable model for studying the pharmacological effects of potential pro-inflammatory or immunomodulating agents. LPS, produced in gram-negative bacteria, is a major causative agent in the pathogenesis of septic shock (Glausner et al., Lancet 338:732, 1991). A shock-like state can indeed be induced experimentally by a single injection of LPS into animals. Molecules produced by cells responding to LPS can target pathogens directly or indirectly. Although these biological responses protect the host against invading pathogens, they may also cause harm. Thus, massive stimulation of innate immunity, occurring as a result of severe Gram-negative bacterial infection, leads to excess production of cytokines and other molecules, and the development of a fatal syndrome, septic shock syndrome, which is characterized by fever, hypotension, disseminated intravascular coagulation, and multiple organ failure (Dumitru et al. Cell 103:1071-1083, 2000).

These toxic effects of LPS are mostly related to macrophage activation leading to the release of multiple inflammatory mediators. Among these mediators, TNF appears to play a crucial role, as indicated by the prevention of LPS toxicity by the administration of neutralizing anti-TNF antibodies (Beutler et al., Science 229:869, 1985). It is well established that 1 ug injection of *E. Coli* LPS into a C57B1/6 mouse will result in significant increases in circulating IL-6, TNF-alpha, IL-1, and acute phase proteins (for example, SAA) approximately 2 hours post injection. The toxicity of LPS appears to be mediated by these cytokines as passive immunization against these mediators can result in decreased mortality (Beutler et al., *Science* 229:869, 1985). The potential immunointervention strategies for the prevention and/or treatment of septic shock include anti-TNF mAb, IL-1 receptor antagonist, LIF, IL-10, and G-CSF. Since LPS induces the production of pro-inflammatory factors possibly contributing to the pathology of endotoxemia, the neutralization of IL-31 activity, SAA or other pro-inflammatory factors by antagonizing IL-31 polypeptide can be used to reduce the symptoms of endotoxemia, such as seen in endotoxic shock. Other potential therapeutics include IL-31 binding molecules or IL-31 antagonists.

3 Inflammatory Bowel Disease. IBD

In the United States approximately many people suffer from Inflammatory Bowel Disease (IBD) which can affect either colon and rectum (Ulcerative colitis) or both, small and large intestine (Crohn's Disease). The pathogenesis of these diseases is unclear, but they involve chronic inflammation of the affected tissues. Potential therapeutics include IL-31RA polypeptides, soluble heterodimeric and multimeric receptor polypeptides, or anti-IL-31 antibodies or binding partners of the present invention, and the like, could serve as a valuable therapeutic to reduce inflammation and pathological effects in IBD and related diseases.

Ulcerative colitis (UC) is an inflammatory disease of the large intestine, commonly called the colon, characterized by inflammation and ulceration of the mucosa or innermost lining of the colon. This inflammation causes the colon to empty frequently, resulting in diarrhea. Symptoms include loosening of the stool and associated abdominal cramping, fever and weight loss. Although the exact cause of UC is unknown, recent research suggests that the body's natural defenses are operating against proteins in the body which the body thinks are foreign (an "autoimmune reaction"). Perhaps because they resemble bacterial proteins in the gut, these proteins may either instigate or stimulate the inflammatory process that begins to destroy the lining of the colon. As the lining of the colon is destroyed, ulcers form releasing mucus, pus and blood. The disease usually begins in the rectal area and may eventually extend through the entire large bowel. Repeated episodes of inflammation lead to thickening of the wall of the intestine and rectum with scar tissue. Death of colon tissue or sepsis may occur with severe disease. The symptoms of ulcerative colitis vary in severity and their onset may be gradual or sudden. Attacks may be provoked by many factors, including respiratory infections or stress.

Although there is currently no cure for UC available, treatments are focused on suppressing the abnormal inflammatory process in the colon lining. Treatments including corticosteroids immunosuppressives (eg. azathioprine, mercaptopurine, and methotrexate) and aminosalicytates are available to treat the disease. However, the long-term use of immunosuppressives such as corticosteroids and azathioprine can result in serious side effects including thinning of bones, cataracts, infection, and liver and bone marrow effects. In the patients in whom current therapies are not successful, surgery is an option. The surgery involves the removal of the entire colon and the rectum.

There are several animal models that can partially mimic chronic ulcerative colitis. The most widely used model is the 2,4,6-trinitrobenesulfonic acid/ethanol (TNBS) induced colitis model, which induces chronic inflammation and ulceration in the colon. When TNBS is introduced into the colon of susceptible mice via intra-rectal instillation, it induces T-cell mediated immune response in the colonic mucosa, in this case leading to a massive mucosal inflammation characterized by the dense infiltration of T-cells and macrophages throughout the entire wall of the large bowel. Moreover, this histopathologic picture is accompanies by the clinical picture of progressive weight loss (wasting), bloody diarrhea, rectal prolapse, and large bowel wall thickening (Neurath et al. *Intern. Rev. Immunol.* 19:51-62, 2000).

Another colitis model uses dextran sulfate sodium (DSS), which induces an acute colitis manifested by bloody diarrhea, weight loss, shortening of the colon and mucosal ulceration with neutrophil infiltration. DSS-induced colitis is characterized histologically by infiltration of inflammatory cells into the lamina propria, with lymphoid hyperplasia, focal crypt damage, and epithelial ulceration. These changes are thought to develop due to a toxic effect of DSS on the epithelium and by phagocytosis of lamina propria cells and production of TNF-alpha and IFN-gamma. Despite its common use, several issues regarding the mechanisms of DSS about the relevance to the human disease remain unresolved. DSS is regarded as a T cell-independent model because it is observed in T cell-deficient animals such as SCID mice.

The administration of anti-IL-31 antibodies or binding partners, soluble IL-31RA comprising polypeptides (including heterodimeric and multimeric receptors), such as IL-31RA-Fc4 or other IL-31RA soluble and fusion proteins to these TNBS or DSS models can be used to evaluate the use of IL-31 antagonists to ameliorate symptoms and alter the course of gastrointestinal disease. IL-31 may play a role in the inflammatory response in colitis, and the neutralization of IL-31 activity by administrating IL-31 binding molecules or IL-31 antagonists is a potential therapeutic approach for IBD.

4. Psoriasis

Psoriasis is a chronic skin condition that affects more than seven million Americans. Psoriasis occurs when new skin cells grow abnormally, resulting in inflamed, swollen, and scaly patches of skin where the old skin has not shed quickly enough. Plaque psoriasis, the most common form, is characterized by inflamed patches of skin ("lesions") topped with silvery white scales. Psoriasis may be limited to a few plaques or involve moderate to extensive areas of skin, appearing most commonly on the scalp, knees, elbows and trunk. Although it is highly visible, psoriasis is not a contagious disease. The pathogenesis of the diseases involves chronic inflammation of the affected tissues. IL-31RA polypeptides, soluble heterodimeric and multimeric receptor polypeptides, or anti-IL-31 antibodies or binding partners of the present invention, and the like, could serve as a valuable therapeutic to reduce inflammation and pathological effects in psoriasis, other inflammatory skin diseases, skin and mucosal allergies, and related diseases.

Psoriasis is a T-cell mediated inflammatory disorder of the skin that can cause considerable discomfort. It is a disease for which there is no cure and affects people of all ages. Psoriasis affects approximately two percent of the populations of European and North America. Although individuals with mild psoriasis can often control their disease with topical agents, more than one million patients worldwide require ultraviolet or systemic immunosuppressive therapy. Unfortunately, the inconvenience and risks of ultraviolet radiation and the toxicities of many therapies limit their long-term use. Moreover, patients usually have recurrence of psoriasis, and in some cases r IL-31 was isolated from tissue known to have important immunological function and which contain cells that play a role in the immune system. IL-31 is expressed in CD3+ selected, activated peripheral blood cells, and it has been shown that IL-31 expression increases after T cell activation. Moreover, results of experiments described in the Examples section herein suggest that polypeptides of the present invention can have an effect on the growth/expansion of monocytes/macrophages, T-cells, B-cells, NK cells and/or differentiated state of monocytes/macrophages, T-cells, B-cells, NK cells or these cells' progenitors. Factors that both stimulate proliferation of hematopoietic progenitors and activate mature cells are generally known, however, proliferation and activation can also require additional growth factors. For example, it has been shown that IL-7 and Steel Factor (c-kit ligand) were required for colony formation of NK progenitors. IL-15+IL-2 in combination with IL-7 and Steel Factor was more effective (MOzek et al., *Blood* 87:2632-2640, 1996). However, unidentified cytokines may be necessary for proliferation of specific subsets of NK cells and/or NK progenitors (Robertson et. al., *Blood* 76:2451-2438, 1990). Similarly, IL-31 may act alone or in concert or synergy with other cytokines to enhance growth, proliferation expansion and modification of differentiation of monocytes/macrophages, T-cells, B-cells or NK cells.

The present invention provides a method for inhibiting activation or differentiation of monocytes/macrophages. Monocytes are incompletely differentiated cells that migrate to various tissues where they mature and become macrophages. Macrophages play a central role in the immune response by presenting antigen to lymphocytes and play a supportive role as accessory cells to lymphocytes by secreting numerous cytokines. Macrophages can internalize extracellular molecules and upon activation have an increased ability to kill intracellular microorganisms and tumor cells. Activated macrophages are also involved in stimulating acute or local inflammation.

The tissue distribution of receptors for a given cytokine offers a strong indication of the potential sites of action of that cytokine. Expression of IL-31RA was seen in monocytes and B-cells, with a dramatic increase of expression upon activation for CD3+, CD4+, and CD8+ T-cells. In addition, two monocytic cell lines, THP-1 (Tsuchiya et al., *Int. J. Cancer* 26:171-176, 1980) and U937 (Sundstrom et al., *Int. J. Cancer* 17:565-577, 1976), were also positive for IL-31RA expression.

Expression of OSMR is reported to be very broad (Mosley et al, *JBC* 271:32635-32643, 1996). This distribution of IL-31RA and OSM receptors supports a role for IL-31 in immune responses, especially expansion of T-cells upon activation or a role in the monocyte/macrophage arm of the immune system.

Thus, particular embodiments of the present invention are directed toward use of IL-31 binding molecules or IL-31 antagonists as antagonists in inflammatory and immune diseases or conditions such as pancreatitis, type I diabetes (IDDM), pancreatic cancer, pancreatitis, Graves Disease, inflammatory bowel disease (IBD), Crohn's Disease, colon and intestinal cancer, diverticulosis, autoimmune disease, sepsis, organ or bone marrow transplant; inflammation due to trauma, surgery or infection; amyloidosis; splenomegaly; graft versus host disease; and where inhibition of inflammation, immune suppression, reduction of proliferation of hematopoietic, immune, inflammatory or lymphoid cells, macrophages, T-cells (including Th1 and Th2 cells, CD4+ and CD8+ cells), suppression of immune response to a pathogen or antigen. Moreover the presence of IL-31RA expression in activated immune cells such as activated CD4+ and CD19+ cells showed that IL-31RA receptor may be involved in the body's immune defensive reactions against foreign invaders: such as microorganisms and cell debris, and could play a role in immune responses during inflammation and cancer formation. As such, antibodies and binding partners of the present invention that are agonistic or antagonistic to IL-31RA receptor function, such as IL-31, can be used to modify immune response and inflammation.

IL-31 binding molecules or IL-31 antagonists may also be used within diagnostic systems for the detection of circulating levels of IL-31. Within a related embodiment, antibodies or other agents that specifically bind to IL-31 polypeptides can be used to detect circulating IL-31 polypeptides. Elevated or depressed levels of ligand polypeptides may be indicative of pathological conditions, including cancer. IL-31 polypeptides may contribute to pathologic processes and can be an indirect marker of an underlying disease.

In atherosclerotic lesions, one of the first abnormalities is localization of monocyte/macrophages to endothelial cells. These lesions could be prevented by use of antagonists to IL-31. IL-31 binding molecules or IL-31 antagonists can also be used as antagonists to the IL-31. Moreover, monoblastic leukemia is associated with a variety of clinical abnormalities that reflect the release of the biologic products of the macrophage, examples include high levels of lysozyme in the serum and urine and high fevers. Moreover, such leukemias exhibit an abnormal increase of monocytic cells. These effects could possibly be prevented by antagonists to IL-31, such as described herein. Moreover, anti-IL-31 can be conjugated to molecules such as toxic moieties and cytokines, as described herein to direct the killing of leukemia monocytic cells.

As IL-31 is expressed in a T-cell, macrophage and monocyte-specific manner, and these diseases involve abnormalities in monocytic cells, such as cell proliferation, function, localization, and activation, the polynucleotides, polypeptides, and antibodies of the present invention can be used to as diagnostics to detect such monocytic cell abnormalities, and indicate the presence of disease. Such methods involve taking a biological sample from a patient, such as blood, saliva, or biopsy, and comparing it to a normal control sample. Histological, cytological, flow cytometric, biochemical and other methods can be used to determine the relative levels or localization of IL-31, or cells expressing IL-31, i.e., monocytes, in the patient sample compared to the normal control. A change in the level (increase or decrease) of IL-31 expression, or a change in number or localization of monocytes (e.g., increase or infiltration of monocytic cells in tissues where they are not normally present) compared to a control would be indicative of disease. Such diagnostic methods can also include using radiometric, fluorescent, and colorimetric tags attached to polynucleotides, polypeptides or antibodies of the present invention. Such methods are well known in the art and disclosed herein.

IL-31 has been shown to be expressed in activated mononuclear cells, and may be involved in regulating inflammation. As such, polypeptides of the present invention can be assayed and used for their ability to modify inflammation, or can be used as a marker for inflammation. Methods to determine proinflammatory and antiinflammatory qualities of IL-31 are known in the art and discussed herein. Moreover, it may be involved in up-regulating the production of acute phase reactants, such as serum amyloid A (SAA), α1-antichymotrypsin, and haptoglobin, and that expression of IL-31RA receptor ligand may be increased upon injection of lipopolysaccharide (LPS) in vivo that are involved in inflammatory response (Dumoutier, L. et al., *Proc. Nat'l. Acad. Sci.* 97:10144-10149, 2000). Production of acute phase proteins, such as SAA, is considered s short-term survival mechanism where inflammation is beneficial; however, maintenance of acute phase proteins for longer periods contributes to chronic inflammation and can be harmful to human health. For review, see Uhlar, C M and Whitehead, A S, *Eur. J. Biochem.* 265:501-523, 1999, and Baumann H. and Gauldie, *J. Immunology Today* 15:74-80, 1994. Moreover, the acute phase protein SAA is implicated in the pathogenesis of several chronic inflammatory diseases, is implicated in atherosclerosis and rheumatoid arthritis, and is the precursor to the amyloid A protein deposited in amyloidosis (Uhlar, C M and Whitehead, supra.). Thus, where a ligand such as IL-31 that acts as a pro-inflammatory molecule and induces production of SAA, antagonists would be useful in treating inflammatory disease and other diseases associated with acute phase response proteins induced by the ligand. Such antagonists are provided by the present invention. For example, a method of reducing inflammation comprises administering to a mammal with inflammation an amount of a composition of IL-31, or anti-IL-31 antibody (e.g., neutralizing antibody) that is sufficient to reduce inflammation. Moreover, a method of suppressing an inflammatory response in a mammal with inflammation can comprise: (1) determining a level of serum amyloid A protein; (2) administering a composition comprising a IL-31 polypeptide or anti-IL-31 antibody as described herein in an acceptable pharmaceutical carrier; (3) determining a post administration level of serum amyloid A protein; (4) comparing the level of serum amyloid A protein in step (1) to the level of serum amyloid A protein in step (3), wherein a lack of increase or a decrease in serum amyloid A protein level is indicative of suppressing an inflammatory response.

Tissue distribution of the mRNA corresponding it's IL-31 RA receptor cDNA showed that mRNA level was highest in monocytes and prostate cells, and is elevated in activated monocytes, and activated CD4+, activated CD8+, and activated CD3+ cells. Hence, IL-31RA receptor is also implicated in inducing inflammatory and immune response. Thus, particular embodiments of the present invention are directed toward use of IL-31 binding molecules or IL-31 antagonists in inflammatory and immune diseases or conditions such as, pancreatitis, type I diabetes (IDDM), pancreatic cancer, pancreatitis, Graves Disease, inflammatory bowel disease (IBD), Crohn's Disease, colon and intestinal cancer, diverticulosis, autoimmune disease, sepsis, organ or bone marrow transplant; inflammation due to trauma, surgery or infection; amyloidosis; splenomegaly; graft versus host disease; and where inhibition of inflammation, immune suppression, reduction of proliferation of hematopoietic, immune, inflammatory or lymphoid cells, macrophages, T-cells (including Th1 and Th2 cells, CD4+ and CD8+ cells), suppression of immune response to a pathogen or antigen. Moreover the presence of IL-31RA receptor and IL-31 expression in activated immune cells such as activated CD3+, monocytes, CD4+ and CD19+ cells showed that IL-31RA receptor may be involved in the body's immune defensive reactions against foreign invaders: such as microorganisms and cell debris, and could play a role in immune responses during inflammation and cancer formation. As such, IL-31 and IL-31-antibodies of the present invention that are agonistic or antagonistic to IL-3 IRA receptor function, can be used to modify immune response and inflammation.

IL-31 binding molecules or IL-31 antagonists are useful to:

Antagonize or block signaling via IL-31RA-comprising receptors in the treatment of acute inflammation, inflammation as a result of trauma, tissue injury, surgery, sepsis or infection, and chronic inflammatory diseases such as asthma, inflammatory bowel disease (IBD), chronic colitis, splenomegaly, rheumatoid arthritis, recurrent acute inflammatory episodes (e.g., tuberculosis), and treatment of amyloidosis, and atherosclerosis, Castleman's Disease, asthma, and other diseases associated with the induction of acute-phase response.

Antagonize or block signaling via the IL-31 RA receptor receptors in the treatment of autoimmune diseases such as IDDM, multiple sclerosis (MS), systemic Lupus erythematosus (SLE), myasthenia gravis, rheumatoid arthritis, and IBD to prevent or inhibit signaling in immune cells (e.g. lymphocytes, monocytes, leukocytes) via IL-31RA receptor (Hughes C et al., *J. Immunol.* 153: 3319-3325, 1994). Alternatively antibodies, such as monoclonal antibodies (MAb) to IL-31, can also be used as an antagonist to deplete unwanted immune cells to treat autoimmune disease. Asthma, allergy and other atopic disease may be treated with an MAb against, for example, anti-IL-31 antibodies, soluble IL-31RA receptor soluble receptors or IL-31RA/CRF2-4 heterodimers, to inhibit the immune response or to deplete offending cells. Blocking or inhibiting signaling via IL-31RA, using the polypeptides and antibodies of the present invention, may also benefit diseases of the pancreas, kidney, pituitary and neuronal cells. IDDM, NIDDM, pancreatitis, and pancreatic carcinoma may benefit. IL-31RA may serve as a target for MAb therapy of cancer where an antagonizing MAb inhibits cancer growth and targets immune-mediated killing. (Holliger P, and Hoogenboom, H: *Nature Biotech.* 16: 1015-1016, 1998). Mabs to soluble IL-31RA receptor monomers, homodimers, heterodimers and multimers may also be useful to treat nephropathies such as glomerulosclerosis, membranous neuropathy, amyloidosis (which also affects the kidney among other tissues), renal arteriosclerosis, glomerulonephritis of various origins, fibroproliferative diseases of the kidney, as well as kidney dysfunction associated with SLE, IDDM, type II diabetes (IDDM), renal tumors and other diseases.

Agonize or initiate signaling via the IL-31RA receptors in the treatment of autoimmune diseases such as IDDM, MS, SLE, myasthenia gravis, rheumatoid arthritis, and IBD. IL-31 may signal lymphocytes or other immune cells to differentiate, alter proliferation, or change production of cytokines or cell surface proteins that ameliorate autoimmunity. Specifically, modulation of a T-helper cell response to an alternate pattern of cytokine secretion may deviate an autoimmune response to ameliorate disease (Smith J A et al., *J. Immunol.* 160:4841-4849, 1998). Similarly, IL-31 may be used to signal, deplete and deviate immune cells involved in asthma, allergy and atopoic disease. Signaling via IL-31RA receptor may also benefit diseases of the pancreas, kidney, pituitary and neuronal cells. IDDM, NIDDM, pancreatitis, and pancreatic carcinoma may benefit. IL-31 RA may serve as a target for MAb therapy of pancreatic cancer where a signaling MAb inhibits cancer growth and targets immune-mediated killing (Tutt, A L et al., *J. Immunol.* 161: 3175-3185, 1998). Similarly T-cell specific leukemias, lymphomas, plasma cell dyscrasia (e.g., multiple myeloma), and carcinoma may be treated with monoclonal antibodies (e.g., neutralizing antibody) to IL-31RA-comprising soluble receptors of the present invention.

Generally, the dosage of administered IL-31 binding molecules or IL-31 antagonists will vary depending upon such factors as the patient's age, weight, height, sex, general medical condition and previous medical history. Typically, it is desirable to provide the recipient with a dosage of IL-31 polypeptide which is in the range of from about 1 pg/kg to 10 mg/kg (amount of agent/body weight of patient), although a lower or higher dosage also may be administered as circumstances dictate. One skilled in the art can readily determine such dosages, and adjustments thereto, using methods known in the art.

Administration of a IL-31 binding molecules or IL-31 antagonists to a subject can be topical, inhalant, intravenous, intraarterial, intraperitoneal, intramuscular, subcutaneous, intrapleural, intrathecal, by perfusion through a regional catheter, or by direct intralesional injection. When administering therapeutic proteins by injection, the administration may be by continuous infusion or by single or multiple boluses.

Additional routes of administration include oral, mucosal-membrane, pulmonary, and transcutaneous. Oral delivery is suitable for polyester microspheres, zein microspheres, proteinoid microspheres, polycyanoacrylate microspheres, and lipid-based systems (see, for example, DiBase and Morrel, "Oral Delivery of Microencapsulated Proteins," in *Protein Delivery: Physical Systems*, Sanders and Hendren (eds.), pages 255-288 (Plenum Press 1997)). The feasibility of an intranasal delivery is exemplified by such a mode of insulin administration (see, for example, Hinchcliffe and Illum, *Adv. Drug Deliv. Rev.* 35:199 (1999)). Dry or liquid particles comprising IL-31 can be prepared and inhaled with the aid of dry-powder dispersers, liquid aerosol generators, or nebulizers (e.g., Peffit and Gombotz, *TIBTECH* 16:343 (1998); Patton et al, *Adv. Drug Deliv. Rev.* 35:235 (1999)). This approach is illustrated by the AERX diabetes management system, which is a hand-held electronic inhaler that delivers aerosolized insulin into the lungs. Studies have shown that proteins as large as 48,000 kDa have been delivered across skin at therapeutic concentrations with the aid of low-frequency ultrasound, which illustrates the feasibility of trascutaneous administration (Mitragotri et al, *Science* 269:850 (1995)). Transdermal delivery using electroporation provides another means to administer a molecule having IL-31 binding activity (Potts et al, *Pharm. Biotechnol.* 10:213 (1997)).

A pharmaceutical composition comprising IL-31 binding molecules or IL-31 antagonists having IL-31 binding activity can be formulated according to known methods to prepare pharmaceutically useful compositions, whereby the therapeutic proteins are combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. See, for example, Gennaro (ed.), *Remington's Pharmaceutical Sciences,* 19th Edition (Mack Publishing Company 1995).

For purposes of therapy, molecules having IL-31 binding activity and a pharmaceutically acceptable carrier are administered to a patient in a therapeutically effective amount. A combination of a protein, polypeptide, or peptide having IL-31 binding activity and a pharmaceutically acceptable carrier is said to be administered in a "therapeutically effective amount" if the amount administered is physiologically significant. An agent is physiologically significant if its presence results in a detectable change in the physiology of a recipient patient. For example, an agent used to treat inflammation is physiologically significant if its presence alleviates at least a portion of the inflammatory response.

A pharmaceutical composition comprising IL-31 binding molecules or IL-31 antagonists can be furnished in liquid form, in an aerosol, or in solid form. Liquid forms, are illustrated by injectable solutions, aerosols, droplets, topological solutions and oral suspensions. Exemplary solid forms include capsules, tablets, and controlled-release forms. The latter form is illustrated by miniosmotic pumps and implants (Bremer et al., *Pharm. Biotechnol.* 10:239 (1997); Ranade, "Implants in Drug Delivery," in *Drug Delivery Systems*, Ranade and Hollinger (eds.), pages 95-123 (CRC Press 1995); Bremer et al., "Protein Delivery with Infusion Pumps," in *Protein Delivery: Physical Systems*, Sanders and Hendren (eds.), pages 239-254 (Plenum Press 1997); Yewey et al, "Delivery of Proteins from a Controlled Release Injectable Implant," in *Protein Delivery: Physical Systems*, Sanders and Hendren (eds.), pages 93-117 (Plenum Press 1997)). Other solid forms include creams, pastes, other topological applications, and the like.

The IL-31 binding molecules or IL-31 antagonists disclosed herein may also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl. Acad. Sci. USA, 77: 4030 (1980); and U.S. Pat. Nos. 4,485,045 and 4,544,545. Liposomes with enhanced circulation time are disclosed in U.S. Pat. No. 5,013,556.

Therapeutic formulations of the IL-31 binding molecules or IL-31 antagonists are prepared for storage by mixing the antibody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as Tween™, Pluronics™ or polyethylene glycol (PEG).

The formulation herein may also contain more than one active compound as necessary for the particular indication being treated, preferably those with complementary activities that do not adversely affect each other. For example, it may be desirable to further provide antibodies which bind to IL-31 in the one formulation. Alternatively, or in addition, the composition may comprise a chemotherapeutic agent or a cytokine. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and .gamma. ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Polypeptides having IL-31 binding activity can be encapsulated within liposomes using standard techniques of protein microencapsulation (see, for example, Anderson et al., *Infect. Immun.* 31:1099 (1981), Anderson et al., *Cancer Res.* 50:1853 (1990), and Cohen et al, *Biochim. Biophys. Acta* 1063:95 (1991), Alving et al "Preparation and Use of Liposomes in Immunological Studies," in *Liposome Technology*, 2nd Edition, Vol. III, Gregoriadis (ed.), page 317 (CRC Press 1993), Wassef et al, *Meth. Enzymol* 149:124 (1987)). As noted above, therapeutically useful liposomes may contain a variety of components. For example, liposomes may comprise lipid derivatives of poly(ethylene glycol) (Allen et al, *Biochim. Biophys. Acta* 1150:9 (1993)).

Degradable polymer microspheres have been designed to maintain high systemic levels of therapeutic proteins. Microspheres are prepared from degradable polymers such as poly (lactide-co-glycolide) (PLG), polyanhydrides, poly (ortho esters), nonbiodegradable ethylvinyl acetate polymers, in which proteins are entrapped in the polymer (Gombotz and Pettit, *Bioconjugate Chem.* 6:332 (1995); Ranade, "Role of Polymers in Drug Delivery," in Drug Delivery Systems, Ranade and Hollinger (eds.), pages 51-93 (CRC Press 1995); Roskos and Maskiewicz, "Degradable Controlled Release Systems Useful for Protein Delivery," in *Protein Delivery: Physical Systems*, Sanders and Hendren (eds.), pages 45-92 (Plenum Press 1997); Bartus et al., *Science* 281:1161 (1998); Putney and Burke, *Nature Biotechnology* 16:153 (1998); Putney, Curr. Opin. Chem. Biol. 2:548 (1998)). Polyethylene glycol (PEG)-coated nanospheres can also provide carriers for intravenous administration of therapeutic proteins (see, for example, Gref et al., *Pharm. Biotechnol.* 10:167 (1997)).

Other dosage forms can be devised by those skilled in the art, as shown, for example, by Ansel and Popovich, *Pharmaceutical Dosage Forms and Drug Delivery Systems*, 5th Edition (Lea & Febiger 1990), Gennaro (ed.), *Remington's Pharmaceutical Sciences*, 19th Edition (Mack Publishing Company 1995), and by Ranade and Hollinger, *Drug Delivery Systems* (CRC Press 1996).

As an illustration, pharmaceutical compositions may be supplied as a kit comprising a container that comprises a IL-31 polypeptide or a IL-31 antagonist (e.g., an antibody or antibody fragment that binds a IL-31 polypeptide). Therapeutic polypeptides can be provided in the form of an injectable solution for single or multiple doses, or as a sterile powder that will be reconstituted before injection. Alternatively, such a kit can include a dry-powder disperser, liquid aerosol generator, or nebulizer for administration of a therapeutic polypeptide.

Within an aspect the present invention pertains to an isolated antibody that binds to human IL31, wherein said antibody is a humanized antibody derived from the monoclonal antibody produced by the hybridoma deposited with the American Type Culture Collection having the ATCC Patent Deposit Designation selected from: a) ATCC Patent Deposit Designation PTA-6815; b) ATCC Patent Deposit Designation PTA-6816; c) ATCC Patent Deposit Designation PTA-6829; d) ATCC Patent Deposit Designation PTA-6830; e) ATCC Patent Deposit Designation PTA-6831; f) ATCC Patent Deposit Designation PTA-6871; g) ATCC Patent Deposit Designation PTA-6872; h) ATCC Patent Deposit Designation PTA-6875; and i) ATCC Patent Deposit Designation PTA-6873; and wherein said antibody comprises a heavy chain immunoglobulin constant domain which is a human IgG4. In an embodiment, the human IgG4 constant domain is a mutated form stable in solution and with little or no complement activating activity. In a particular embodiment, the heavy chain immunoglobulin constant region domain is a human IgG4 constant domain with a Ser to Pro mutation at position 241 (Kabat numbering).

Within another aspect these antibodies are used to treat diseases including atopic dermatitis, contact dermatitis, drug-induced allergic reactions, skin-tropic viruses and viral associated pruritis, vitiligo, cutaneous T cell lymphoma, alopecia aerata, acne rosacea, acne vulgaris, prurigo nodularis, and bullous pemphigoid, as discussed herein.

In an embodiment, the present invention pertains to an isolated antibody as disclosed herein wherein the immunoglobulin light chain constant region domain is selected from the group consisting of the constant region of a kappa or lambda human immunoglobulin light chain. Preferably, the immunoglobulin light chain constant region domain is the constant region of a kappa human immunoglobulin light chain.

In an aspect, the present invention pertains to an isolated antibody as disclosed herein wherein the heavy chain variable domain and the light chain variable domain comprises the CDR sequences of clones 292.12.3.1, 292.84.1.6, 292.63.5.3, 294.144.3.5, 292.39.5.3, 292.51.5.2, 292.64.6.5.5, 292.105.4.1, 292.109.4.4, 292.118.6.4, and 292.72.3.1. The CDR sequences are shown in the Figures and in Table 3, below.

In an aspect, the present invention pertains to an isolated antibody as disclosed herein wherein a) the heavy chain variable domain comprises first CDR sequence consisting of amino acid sequence SEQ ID NO: 51, a second CDR sequence consisting of SEQ ID NO: 52 or SEQ ID NO: 57, and a third CDR sequence consisting of SEQ ID NO:53; and b) the light chain variable domain comprises first CDR sequence consisting of amino acid sequence SEQ ID NO: 54, a second CDR sequence consisting of SEQ ID NO: 55, and a third CDR sequence consisting of SEQ ID NO:56. In an embodiment, the antibody is used to treat diseases including atopic dermatitis, contact dermatitis, drug-induced allergic reactions, skin-tropic viruses and viral associated pruritis, vitiligo, cutaneous T cell lymphoma, alopecia aerata, acne rosacea, acne vulgaris, prurigo nodularis, and bullous pemphigoid, as discussed herein. In another embodiment, chemokines such are TARC or MDC are measured.

In an embodiment, the present invention pertains to an isolated antibody as disclosed herein wherein a) the heavy chain variable domain comprises first CDR sequence consisting of amino acid sequence SEQ ID NO: 51, a second CDR sequence consisting of SEQ ID NO: 58, and a third CDR sequence consisting of SEQ ID NO:59; and b) the light chain variable domain comprises first CDR sequence consisting of amino acid sequence SEQ ID NO: 60, a second CDR sequence consisting of SEQ ID NO: 61, and a third CDR sequence consisting of SEQ ID NO:62. In an embodiment, the antibody is used to treat diseases including atopic dermatitis, contact dermatitis, drug-induced allergic reactions, skin-tropic viruses and viral associated pruritis, vitiligo, cutaneous T cell lymphoma, alopecia aerata, acne rosacea, acne vulgaris, prurigo nodularis, and bullous pemphigoid, as discussed herein. In another embodiment, chemokines such are TARC or MDC are measured.

In an embodiment, the present invention pertains to an isolated antibody as disclosed herein wherein a) the heavy chain variable domain comprises first CDR sequence consisting of amino acid sequence SEQ ID NO: 63, a second CDR sequence consisting of SEQ ID NO: 64, and a third CDR sequence consisting of SEQ ID NO:65; and b) the light chain variable domain comprises first CDR sequence consisting of amino acid sequence SEQ ID NO: 66, a second CDR sequence consisting of SEQ ID NO: 67, and a third CDR sequence consisting of SEQ ID NO:68. In an embodiment, the antibody is used to treat diseases including atopic dermatitis, contact dermatitis, drug-induced allergic reactions, skin-tropic viruses and viral associated pruritis, vitiligo, cutaneous T cell lymphoma, alopecia aerata, acne rosacea, acne vulgaris, prurigo nodularis, and bullous pemphigoid, as discussed herein. In another embodiment, chemokines such are TARC or MDC are measured.

In an embodiment, the present invention pertains to an isolated antibody as disclosed herein wherein a) the heavy chain variable domain comprises first CDR sequence consisting of amino acid sequence SEQ ID NO: 69, a second CDR sequence consisting of SEQ ID NO: 70 or SEQ ID NO: 79, and a third CDR sequence consisting of SEQ ID NO:71; and b) the light chain variable domain comprises first CDR sequence consisting of amino acid sequence SEQ ID NO: 72, a second CDR sequence consisting of SEQ ID NO: 73, and a third CDR sequence consisting of SEQ ID NO:74. In an embodiment, the antibody is used to treat diseases including atopic dermatitis, contact dermatitis, drug-induced allergic reactions, skin-tropic viruses and viral associated pruritis, vitiligo, cutaneous T cell lymphoma, alopecia aerata, acne rosacea, acne vulgaris, prurigo nodularis, and bullous pemphigoid, as discussed herein. In another embodiment, chemokines such are TARC or MDC are measured.

In an embodiment, the present invention pertains to an isolated antibody as disclosed herein wherein a) the heavy chain variable domain comprises first CDR sequence consisting of amino acid sequence SEQ ID NO: 75, a second CDR sequence consisting of SEQ ID NO: 76, and a third CDR sequence consisting of SEQ ID NO:65; and b) the light chain variable domain comprises first CDR sequence consisting of amino acid sequence SEQ ID NO: 77, a second CDR sequence consisting of SEQ ID NO: 78, and a third CDR sequence consisting of SEQ ID NO:68. In an embodiment, the antibody is used to treat diseases including atopic dermatitis, contact dermatitis, drug-induced allergic reactions, skin-tropic viruses and viral associated pruritis, vitiligo, cutaneous T cell lymphoma, alopecia aerata, acne rosacea, acne vulgaris, prurigo nodularis, and bullous pemphigoid, as discussed herein. In another embodiment, chemokines such are TARC or MDC are measured.

In an embodiment, the present invention pertains to an isolated antibody as disclosed herein wherein a) the heavy chain variable domain comprises first CDR sequence consisting of amino acid sequence SEQ ID NO: 80, a second CDR sequence consisting of SEQ ID NO: 817, and a third CDR sequence consisting of SEQ ID NO:82; and b) the light chain variable domain comprises first CDR sequence consisting of amino acid sequence SEQ ID NO: 83, a second CDR sequence consisting of SEQ ID NO: 84, and a third CDR sequence consisting of SEQ ID NO:85. In an embodiment, the antibody is used to treat diseases including atopic dermatitis, contact dermatitis, drug-induced allergic reactions, skin-tropic viruses and viral associated pruritis, vitiligo, cutaneous T cell lymphoma, alopecia aerata, acne rosacea, acne vulgaris, prurigo nodularis, and bullous pemphigoid, as discussed herein. In another embodiment, chemokines such are TARC or MDC are measured.

Within one aspect, the invention provides a monoclonal antibody or antibody fragment that competes for specifically binding to a polypeptide comprising the amino acid sequence of SEQ ID NO: 2 wherein the monoclonal antibody comprises a light chain variable region and a heavy chain variable region selected from the group consisting of: a) a light chain variable region comprising the amino acid sequence of SEQ ID NO: 8 and a heavy chain variable region comprising the amino acid sequence of SEQ ID NO: 9; b) a light chain variable region comprising the amino acid sequence of SEQ ID NO: 10 and a heavy chain variable region comprising the amino acid sequence of SEQ ID NO: 11; c) a light chain variable region comprising the amino acid sequence of SEQ ID NO: 12 and a heavy chain variable region comprising the amino acid sequence of SEQ ID NO: 13; d) a light chain variable region comprising the amino acid sequence of SEQ ID NO: 14 and a heavy chain variable region comprising the amino acid sequence of SEQ ID NO: 15; e) a light chain variable region comprising the amino acid sequence of SEQ ID NO: 16 and a heavy chain variable region comprising the amino acid sequence of SEQ ID NO: 17; f) a light chain variable region comprising the amino acid sequence of SEQ ID NO: 18 and a heavy chain variable region comprising the amino acid sequence of SEQ ID NO: 19; g) a light chain variable region comprising the amino acid sequence of SEQ ID NO: 20 and a heavy chain variable region comprising the amino acid sequence of SEQ ID NO: 21; h) a light chain variable region comprising the amino acid sequence of SEQ ID NO: 22 and a heavy chain variable region comprising the amino acid sequence of SEQ ID NO: 23; i) a light chain variable region comprising the amino acid sequence of SEQ ID NO: 24 and a heavy chain variable region comprising the amino acid sequence of SEQ ID NO: 25; and i) a light chain variable region comprising the amino acid sequence of SEQ ID NO: 26 and a heavy chain variable region comprising the amino acid sequence of SEQ ID NO: 27 and wherein the monoclonal antibody or antibody fragment is used in conjunction with an human IgG4 Fc molecule. Within an embodiment, the monoclonal antibody or antibody fragment inhibits, blocks, or neutralizes the interaction of IL-31 (SEQ ID NO:2) with IL-31RA (SEQ ID NO:5). Within another embodiment, the monoclonal antibody or antibody fragment is selected from the group consisting of: (a) a murine monoclonal antibody or antibody fragment; (b) a humanized antibody or antibody fragment or antibody fragment; and (c) a human monoclonal antibody. Within another embodiment, the antibody further comprises PEGylation.

Within another aspect, the invention provides, a monoclonal antibody or antibody fragment comprising a light chain variable region and a heavy chain variable region where the monoclonal antibody or antibody fragment is selected from the group consisting of: a) a monoclonal antibody or antibody fragment that competes for specifically binding to a polypeptide comprising the amino acid sequence of SEQ ID NO: 2 wherein the monoclonal antibody or antibody fragment comprises a light chain variable region and a heavy chain variable region selected from the group consisting of: i) a light chain variable region comprising the amino acid sequence of SEQ ID NO: 8 and a heavy chain variable region comprising the amino acid sequence of SEQ ID NO: 9; and ii) a light chain variable region comprising the amino acid sequence of SEQ ID NO: 26 and a heavy chain variable region comprising the amino acid sequence of SEQ ID NO: 27; and b) a monoclonal antibody or antibody fragment that competes for specifically binding to a polypeptide comprising the amino acid sequence of SEQ ID NO: 2 wherein the monoclonal antibody or antibody fragment comprises a light chain variable region and a heavy chain variable region selected from the group consisting of: i) a light chain variable region comprising the amino acid sequence of SEQ ID NO: 10 and a heavy chain variable region comprising the amino acid sequence of SEQ ID NO: 11; ii) a light chain variable region comprising the amino acid sequence of SEQ ID NO: 12 and a heavy chain variable region comprising the amino acid sequence of SEQ ID NO: 13; iii) a light chain variable region comprising the amino acid sequence of SEQ ID NO: 14 and a heavy chain variable region comprising the amino acid sequence of SEQ ID NO: 15; iv) a light chain variable region comprising the amino acid sequence of SEQ ID NO: 16 and a heavy chain variable region comprising the amino acid sequence of SEQ ID NO: 17; v) a light chain variable region comprising the amino acid sequence of SEQ ID NO: 18 and a heavy chain variable region comprising the amino acid sequence of SEQ ID NO: 19; vi) a light chain variable region comprising the amino acid sequence of SEQ ID NO: 20 and a heavy chain variable region comprising the amino acid sequence of SEQ ID NO: 21; vii) a light chain variable region comprising the amino acid sequence of SEQ ID NO: 22 and a heavy chain variable region comprising the amino acid sequence of SEQ ID NO: 23; and vii) a light chain variable region comprising the amino acid sequence of SEQ ID NO: 24 and a heavy chain variable region comprising the amino acid sequence of SEQ ID NO: 25 and wherein the monoclonal antibody or antibody fragment is used in conjunction with an human IgG4 Fc molecule. Within an embodiment, the monoclonal antibody or antibody fragment inhibits, blocks, or neutralizes the interaction of IL-31 (SEQ ID NO:2) with IL-31RA (SEQ ID NO:5). Within another embodiment the monoclonal antibody or antibody fragment competes for specifically binding to a polypeptide comprising the amino acid sequence of SEQ ID NO: 2 wherein the monoclonal antibody or antibody fragment comprises a light chain variable region and a heavy chain variable region selected from the group consisting of: a) a light chain variable region comprising the amino acid sequence of SEQ ID NO: 8 and a heavy chain variable region comprising the amino acid sequence of SEQ ID NO: 9; and b) a light chain variable region comprising the amino acid sequence of SEQ ID NO: 26 and a heavy chain variable region comprising the amino acid sequence of SEQ ID NO: 27 and wherein the monoclonal antibody or antibody fragment is used in conjunction with an human IgG4 Fc molecule. Within another embodiment, the monoclonal antibody is selected from the group consisting of: (a) a murine monoclonal antibody or antibody fragment; (b) a humanized antibody or antibody fragment or antibody fragment; and (c) a human monoclonal antibody. Within another embodiment, the antibody further comprises PEGylation. Within another embodiment, the monoclonal antibody or antibody fragment competes for specifically binding to a polypeptide comprising the amino acid sequence of SEQ ID NO: 2 wherein the monoclonal antibody or antibody fragment comprises a light chain variable region and a heavy chain variable region selected from the group consisting of: a) a light chain variable region comprising the amino acid sequence of SEQ ID NO: 10 and a heavy chain variable region comprising the amino acid sequence of SEQ ID NO: 11; b) a light chain variable region comprising the amino acid sequence of SEQ ID NO: 12 and a heavy chain variable region comprising the amino acid sequence of SEQ ID NO: 13; c) a light chain variable region comprising the amino acid sequence of SEQ ID NO: 14 and a heavy chain variable region comprising the amino acid sequence of SEQ ID NO: 15; d) a light chain variable region comprising the amino acid sequence of SEQ ID NO: 16 and a heavy chain variable region comprising the amino acid sequence of SEQ ID NO: 17; e) a light chain variable region comprising the amino acid sequence of SEQ ID NO: 18 and a heavy chain variable region comprising the amino acid sequence of SEQ ID NO: 19; f) a light chain variable region comprising the amino acid sequence of SEQ ID NO: 20 and a heavy chain variable region comprising the amino acid sequence of SEQ ID NO: 21; g) a light chain variable region comprising the amino acid sequence of SEQ ID NO: 22 and a heavy chain variable region comprising the amino acid sequence of SEQ ID NO: 23; and h) a light chain variable region comprising the amino acid sequence of SEQ ID NO: 24 and a heavy chain variable region comprising the amino acid sequence of SEQ ID NO: 25. Within another embodiment, the monoclonal antibody is selected from the group consisting of: (a) a murine monoclonal antibody or antibody fragment; (b) a humanized antibody or antibody fragment or antibody fragment; and (c) a human monoclonal antibody. Within another embodiment, the antibody further comprises PEGylation.

Within another aspect, the invention provides, a method of reducing, blocking, inhibiting, or neutralizing inflammation in a mammal comprising administering to the mammal an monoclonal antibody or antibody fragment that competes for specifically binding to a polypeptide comprising the amino acid sequence of SEQ ID NO: 2 wherein the monoclonal antibody comprises a light chain variable region and a heavy chain variable region selected from the group consisting of: a) a light chain variable region comprising the amino acid sequence of SEQ ID NO: 8 and a heavy chain variable region comprising the amino acid sequence of SEQ ID NO: 9; b) a light chain variable region comprising the amino acid sequence of SEQ ID NO: 10 and a heavy chain variable region comprising the amino acid sequence of SEQ ID NO: 11; c) a light chain variable region comprising the amino acid sequence of SEQ ID NO: 12 and a heavy chain variable region comprising the amino acid sequence of SEQ ID NO: 13; d) a light chain variable region comprising the amino acid sequence of SEQ ID NO: 14 and a heavy chain variable region comprising the amino acid sequence of SEQ ID NO: 15; e) a light chain variable region comprising the amino acid sequence of SEQ ID NO: 16 and a heavy chain variable region comprising the amino acid sequence of SEQ ID NO: 17; f) a light chain variable region comprising the amino acid sequence of SEQ ID NO: 18 and a heavy chain variable region comprising the amino acid sequence of SEQ ID NO: 19; g) a light chain variable region comprising the amino acid sequence of SEQ ID NO: 20 and a heavy chain variable region comprising the amino acid sequence of SEQ ID NO: 21; h) a light chain variable region comprising the amino acid sequence of SEQ ID NO: 22 and a heavy chain variable region comprising the amino acid sequence of SEQ ID NO: 23; i) a light chain variable region comprising the amino acid sequence of SEQ ID NO: 24 and a heavy chain variable region comprising the amino acid sequence of SEQ ID NO: 25; and i) a light chain variable region comprising the amino acid sequence of SEQ ID NO: 26 and a heavy chain variable region comprising the amino acid sequence of SEQ ID NO: 27 and wherein the monoclonal antibody or antibody fragment is used in conjunction with an human IgG4 Fc molecule. Within an embodiment, administration of the antibody to the mammal reduces, blocks, inhibits, or neutralizes production of pro-inflammatory chemokines. Within a further embodiment, the pro-inflammatory chemokines are TARC or MDC. Within another embodiment, the monoclonal antibody or antibody fragment competes for specifically binding to a polypeptide comprising the amino acid sequence of SEQ ID NO: 2 wherein the monoclonal antibody or antibody fragment comprises a light chain variable region and a heavy chain variable region selected from the group consisting of: a) a light chain variable region comprising the amino acid sequence of SEQ ID NO: 8 and a heavy chain variable region comprising the amino acid sequence of SEQ ID NO: 9; and b) a light chain variable region comprising the amino acid sequence of SEQ ID NO: 26 and a heavy chain variable region comprising the amino acid sequence of SEQ ID NO: 27 and wherein the monoclonal antibody or antibody fragment is used in conjunction with an human IgG4 Fc molecule. Within another embodiment, the monoclonal antibody or antibody fragment competes for specifically binding to a polypeptide comprising the amino acid sequence of SEQ ID NO: 2 wherein the monoclonal antibody or antibody fragment comprises a light chain variable region and a heavy chain variable region selected from the group consisting of: a) a light chain variable region comprising the amino acid sequence of SEQ ID NO: 10 and a heavy chain variable region comprising the amino acid sequence of SEQ ID NO: 1; b) a light chain variable region comprising the amino acid sequence of SEQ ID NO: 12 and a heavy chain variable region comprising the amino acid sequence of SEQ ID NO: 13; c) a light chain variable region comprising the amino acid sequence of SEQ ID NO: 14 and a heavy chain variable region comprising the amino acid sequence of SEQ ID NO: 15; d) a light chain variable region comprising the amino acid sequence of SEQ ID NO: 16 and a heavy chain variable region comprising the amino acid sequence of SEQ ID NO: 17; e) a light chain variable region comprising the amino acid sequence of SEQ ID NO: 18 and a heavy chain variable region comprising the amino acid sequence of SEQ ID NO: 19; f) a light chain variable region comprising the amino acid sequence of SEQ ID NO: 20 and a heavy chain variable region comprising the amino acid sequence of SEQ ID NO: 21; g) a light chain variable region comprising the amino acid sequence of SEQ ID NO: 22 and a heavy chain variable region comprising the amino acid sequence of SEQ ID NO: 23; and h) a light chain variable region comprising the amino acid sequence of SEQ ID NO: 24 and a heavy chain variable region comprising the amino acid sequence of SEQ ID NO: 25.

Within another aspect, the invention provides, a method of reducing, blocking, inhibiting, or neutralizing pruritis in a mammal comprising administering to the mammal an monoclonal antibody or antibody fragment that competes for specifically binding to a polypeptide comprising the amino acid sequence of SEQ ID NO: 2 wherein the monoclonal antibody comprises a light chain variable region and a heavy chain variable region selected from the group consisting of: a) a light chain variable region comprising the amino acid sequence of SEQ ID NO: 8 and a heavy chain variable region comprising the amino acid sequence of SEQ ID NO: 9; b) a light chain variable region comprising the amino acid sequence of SEQ ID NO: 10 and a heavy chain variable region comprising the amino acid sequence of SEQ ID NO: 11; c) a light chain variable region comprising the amino acid sequence of SEQ ID NO: 12 and a heavy chain variable region comprising the amino acid sequence of SEQ ID NO: 13; d) a light chain variable region comprising the amino acid sequence of SEQ ID NO: 14 and a heavy chain variable region comprising the amino acid sequence of SEQ ID NO: 15; e) a light chain variable region comprising the amino acid sequence of SEQ ID NO: 16 and a heavy chain variable region comprising the amino acid sequence of SEQ ID NO: 17; f) a light chain variable region comprising the amino acid sequence of SEQ ID NO: 18 and a heavy chain variable region comprising the amino acid sequence of SEQ ID NO: 19; g) a light chain variable region comprising the amino acid sequence of SEQ ID NO: 20 and a heavy chain variable region comprising the amino acid sequence of SEQ ID NO: 21; h) a light chain variable region comprising the amino acid sequence of SEQ ID NO: 22 and a heavy chain variable region comprising the amino acid sequence of SEQ ID NO: 23; i) a light chain variable region comprising the amino acid sequence of SEQ ID NO: 24 and a heavy chain variable region comprising the amino acid sequence of SEQ ID NO: 25; and i) a light chain variable region comprising the amino acid sequence of SEQ ID NO: 26 and a heavy chain variable region comprising the amino acid sequence of SEQ ID NO: 27 and wherein the monoclonal antibody or antibody fragment is used in conjunction with an human IgG4 Fc molecule. Within an embodiment, the monoclonal antibody or antibody fragment competes for specifically binding to a polypeptide comprising the amino acid sequence of SEQ ID NO: 2 wherein the monoclonal antibody or antibody fragment comprises a light chain variable region and a heavy chain variable region selected from the group consisting of: a) a light chain variable region comprising the amino acid sequence of SEQ ID NO: 8 and a heavy chain variable region comprising the amino acid sequence of SEQ ID NO: 9; and b) a light chain variable region comprising the amino acid sequence of SEQ ID NO: 26 and a heavy chain variable region comprising the amino acid sequence of SEQ ID NO: 27 and wherein the monoclonal antibody or antibody fragment is used in conjunction with an human IgG4 Fc molecule. Within another embodiment the monoclonal antibody or antibody fragment competes for specifically binding to a polypeptide comprising the amino acid sequence of SEQ ID NO: 2 wherein the monoclonal antibody or antibody fragment comprises a light chain variable region and a heavy chain variable region selected from the group consisting of: a) a light chain variable region comprising the amino acid sequence of SEQ ID NO: 10 and a heavy chain variable region comprising the amino acid sequence of SEQ ID NO: 1; b) a light chain variable region comprising the amino acid sequence of SEQ ID NO: 12 and a heavy chain variable region comprising the amino acid sequence of SEQ ID NO: 13; c) a light chain variable region comprising the amino acid sequence of SEQ ID NO: 14 and a heavy chain variable region comprising the amino acid sequence of SEQ ID NO: 15; d) a light chain variable region comprising the amino acid sequence of SEQ ID NO: 16 and a heavy chain variable region comprising the amino acid sequence of SEQ ID NO: 17; e) a light chain variable region comprising the amino acid sequence of SEQ ID NO: 18 and a heavy chain variable region comprising the amino acid sequence of SEQ ID NO: 19; f) a light chain variable region comprising the amino acid sequence of SEQ ID NO: 20 and a heavy chain variable region comprising the amino acid sequence of SEQ ID NO: 21; g) a light chain variable region comprising the amino acid sequence of SEQ ID NO: 22 and a heavy chain variable region comprising the amino acid sequence of SEQ ID NO: 23; and h) a light chain variable region comprising the amino acid sequence of SEQ ID NO: 24 and a heavy chain variable region comprising the amino acid sequence of SEQ ID NO: 25. Within another embodiment, administration of the monoclonal antibody or antibody fragment reduces, blocks, inhibits, or neutralizes dermatitis. Within a further embodiment, the dermatitis is atopic dermatitis or prurigo nodularis.

Within another aspect, the invention provides a method of reducing, blocking, inhibiting, or neutralizing scratching in a mammal comprising administering to the mammal an monoclonal antibody or antibody fragment that competes for specifically binding to a polypeptide comprising the amino acid sequence of SEQ ID NO: 2 wherein the monoclonal antibody comprises a light chain variable region and a heavy chain variable region selected from the group consisting of: a) a light chain variable region comprising the amino acid sequence of SEQ ID NO: 8 and a heavy chain variable region comprising the amino acid sequence of SEQ ID NO: 9; b) a light chain variable region comprising the amino acid sequence of SEQ ID NO: 10 and a heavy chain variable region comprising the amino acid sequence of SEQ ID NO: 11; c) a light chain variable region comprising the amino acid sequence of SEQ ID NO: 12 and a heavy chain variable region comprising the amino acid sequence of SEQ ID NO: 13; d) a light chain variable region comprising the amino acid sequence of SEQ ID NO: 14 and a heavy chain variable region comprising the amino acid sequence of SEQ ID NO: 15; e) a light chain variable region comprising the amino acid sequence of SEQ ID NO: 16 and a heavy chain variable region comprising the amino acid sequence of SEQ ID NO: 17; f) a light chain variable region comprising the amino acid sequence of SEQ ID NO: 18 and a heavy chain variable region comprising the amino acid sequence of SEQ ID NO: 19; g) a light chain variable region comprising the amino acid sequence of SEQ ID NO: 20 and a heavy chain variable region comprising the amino acid sequence of SEQ ID NO: 21; h) a light chain variable region comprising the amino acid sequence of SEQ ID NO: 22 and a heavy chain variable region comprising the amino acid sequence of SEQ ID NO: 23; i) a light chain variable region comprising the amino acid sequence of SEQ ID NO: 24 and a heavy chain variable region comprising the amino acid sequence of SEQ ID NO: 25; and j) a light chain variable region comprising the amino acid sequence of SEQ ID NO: 26 and a heavy chain variable region comprising the amino acid sequence of SEQ ID NO: 27 and wherein the monoclonal antibody or antibody fragment is used in conjunction with an human IgG4 Fc molecule. Within another embodiment the monoclonal antibody or antibody fragment competes for specifically binding to a polypeptide comprising the amino acid sequence of SEQ ID NO: 2 wherein the monoclonal antibody or antibody fragment comprises a light chain variable region and a heavy chain variable region selected from the group consisting of: a) a light chain variable region comprising the amino acid sequence of SEQ ID NO: 8 and a heavy chain variable region comprising the amino acid sequence of SEQ ID NO: 9; and b) a light chain variable region comprising the amino acid sequence of SEQ ID NO: 26 and a heavy chain variable region comprising the amino acid sequence of SEQ ID NO: 27 and wherein the monoclonal antibody or antibody fragment is used in conjunction with an human IgG4 Fc molecule. Within another embodiment, the monoclonal antibody or antibody fragment competes for specifically binding to a polypeptide comprising the amino acid sequence of SEQ ID NO: 2 wherein the monoclonal antibody or antibody fragment comprises a light chain variable region and a heavy chain variable region selected from the group consisting of: a) a light chain variable region comprising the amino acid sequence of SEQ ID NO: 10 and a heavy chain variable region comprising the amino acid sequence of SEQ ID NO: 1; b) a light chain variable region comprising the amino acid sequence of SEQ ID NO: 12 and a heavy chain variable region comprising the amino acid sequence of SEQ ID NO: 13; c) a light chain variable region comprising the amino acid sequence of SEQ ID NO: 14 and a heavy chain variable region comprising the amino acid sequence of SEQ ID NO: 15; d) a light chain variable region comprising the amino acid sequence of SEQ ID NO: 16 and a heavy chain variable region comprising the amino acid sequence of SEQ ID NO: 17; e) a light chain variable region comprising the amino acid sequence of SEQ ID NO: 18 and a heavy chain variable region comprising the amino acid sequence of SEQ ID NO: 19; f) a light chain variable region comprising the amino acid sequence of SEQ ID NO: 20 and a heavy chain variable region comprising the amino acid sequence of SEQ ID NO: 21; g) a light chain variable region comprising the amino acid sequence of SEQ ID NO: 22 and a heavy chain variable region comprising the amino acid sequence of SEQ ID NO: 23; and h) a light chain variable region comprising the amino acid sequence of SEQ ID NO: 24 and a heavy chain variable region comprising the amino acid sequence of SEQ ID NO: 25.

Within another aspect, the present invention provides a method for inhibiting IL-31-induced proliferation or differentiation of hematopoietic cells and hematopoietic cell progenitors comprising culturing bone marrow or peripheral blood cells with a composition comprising an amount of an IL-31 binding molecules or IL-31 antagonists as disclosed herein sufficient to reduce proliferation or differentiation of the hematopoietic cells in the bone marrow or peripheral blood cells as compared to bone marrow or peripheral blood cells cultured in the absence of soluble cytokine receptor. In one embodiment the method for inhibiting IL-31-induced proliferation or differentiation of hematopoietic cells and hematopoietic cell progenitors is as disclosed above, wherein the hematopoietic cells and hematopoietic progenitor cells are lymphoid cells. In another embodiment the method for inhibiting IL-31-induced proliferation or differentiation of hematopoietic cells and hematopoietic cell progenitors is as disclosed above, wherein the lymphoid cells are macrophages or T cells.

Within another aspect, the present invention provides a method of reducing IL-31-induced induced inflammation comprising administering to a mammal with inflammation an amount of a composition of a an IL-31 binding molecules or IL-31 antagonists as disclosed herein sufficient to reduce inflammation.

Within another aspect, the present invention provides a method of suppressing an inflammatory response in a mammal with inflammation comprising: (1) determining a level of an inflammatory molecule; (2) administering a composition comprising an IL-31 binding molecules or IL-31 antagonists as disclosed herein in an acceptable pharmaceutical vehicle; (3) determining a post administration level of the inflammatory molecule; (4) comparing the level of the inflammatory molecule in step (1) to the level of the inflammatory molecule in step (3), wherein a lack of increase or a decrease the inflammatory molecule level is indicative of suppressing an inflammatory response. In one embodiment, the antibody is as disclosed above, wherein the antibody further comprises a radionuclide, enzyme, substrate, cofactor, fluorescent marker, chemiluminescent marker, peptide tag, magnetic particle, drug, or toxin.

Within another aspect, the present invention provides a method for inhibiting IL-31-induced proliferation or differentiation of hematopoietic cells and hematopoietic cell progenitors comprising culturing bone marrow or peripheral blood cells with a composition comprising an amount of an IL-31 binding molecules or IL-31 antagonists as disclosed herein sufficient to reduce proliferation or differentiation of the hematopoietic cells in the bone marrow or peripheral blood cells as compared to bone marrow or peripheral blood cells cultured in the absence of soluble cytokine receptor. In one embodiment the method for inhibiting IL-31-induced proliferation or differentiation of hematopoietic cells and hematopoietic cell progenitors is as disclosed above, wherein the hematopoietic cells and hematopoietic progenitor cells are lymphoid cells. In another embodiment the method for inhibiting IL-31-induced proliferation or differentiation of hematopoietic cells and hematopoietic cell progenitors is as disclosed above, wherein the lymphoid cells are macrophages or T cells.

Within another aspect, the present invention provides a method of reducing IL-31-induced induced inflammation comprising administering to a mammal with inflammation an amount of a composition of a an IL-31 binding molecules or IL-31 antagonists as disclosed herein sufficient to reduce inflammation.

Within another aspect, the present invention provides a method of suppressing an inflammatory response in a mammal with inflammation comprising: (1) determining a level of an inflammatory molecule; (2) administering a composition comprising an antibody IL-31 binding molecules or IL-31 antagonists as disclosed herein in an acceptable pharmaceutical vehicle; (3) determining a post administration level of the inflammatory molecule; (4) comparing the level of the inflammatory molecule in step (1) to the level of the inflammatory molecule in step (3), wherein a lack of increase or a decrease in the inflammatory molecule level is indicative of suppressing an inflammatory response.

Within another aspect, the present invention provides a method of treating a mammal afflicted with an inflammatory disease in which IL-31 plays a role, comprising: administering an antagonist of IL-31 to the mammal such that the inflammation is reduced, wherein the antagonist is selected from the group consisting of an IL-31 binding molecules or IL-31 antagonists that specifically binds a polypeptide or polypeptide fragment of IL-31 (SEQ ID NO:2). In one embodiment, the method of treating a mammal afflicted with an inflammatory disease is as disclosed above, wherein the disease is a chronic inflammatory disease. In another embodiment, the method of treating a mammal afflicted with an inflammatory disease is as disclosed above, wherein the disease is a chronic inflammatory disease selected from the group consisting of: inflammatory bowel disease; ulcerative colitis; Crohn's disease; atopic dermatitis; eczema; and psoriasis. In another embodiment, the method of treating a mammal afflicted with an inflammatory disease is as disclosed above, wherein the disease is an acute inflammatory disease. In another embodiment, the method of treating a mammal afflicted with an inflammatory disease is as disclosed above, wherein the disease is an acute inflammatory disease selected from the group consisting of: endotoxemia; septicemia; toxic shock syndrome; and infectious disease. In another embodiment, the method of treating a mammal afflicted with an inflammatory disease is as disclosed above, wherein the antibody further comprises a radionuclide, enzyme, substrate, cofactor, fluorescent marker, chemiluminescent marker, peptide tag, magnetic particle, drug, or toxin.

Within another aspect, the present invention provides a method for detecting inflammation in a patient, comprising: obtaining a tissue or biological sample from a patient; incubating the tissue or biological sample with an IL-31 binding molecules or IL-31 antagonists as disclosed herein under conditions wherein the IL-31 binding molecules or IL-31 antagonists binds to its complementary polypeptide in the tissue or biological sample; visualizing the IL-31 binding molecules or IL-31 antagonists bound in the tissue or biological sample; and comparing levels of IL-31 binding molecules or IL-31 antagonists bound in the tissue or biological sample from the patient to a normal control tissue or biological sample, wherein an increase in the level of IL-31 binding molecules or IL-31 antagonists bound to the patient tissue or biological sample relative to the normal control tissue or biological sample is indicative of inflammation in the patient.

The invention is further illustrated by the following non-limiting examples.

EXAMPLES

Example 1

Determination of Variable Regions

Sequences of the light and heavy chain variable regions were determined in the following manner:

RNA Extraction/5' RACE Ready cDNA Production:

Hybridoma cell lines (approximately 4.5×106 cells) were collected by centrifugation after washing in 1×PBS. RNA was purified using Qiagen's RNeasy mini purification kit according to the manufacture's instructions. Resulting RNA was displayed on a 1.2% E-Gel for validation. First strand cDNA synthesis was performed using BD Biosciences BD SMART RACE cDNA Amplification Kit, which provided 5' RACE Ready cDNA.

Amplification of Light and Heavy Chain Variable Region Sequences:

5' RACE ready cDNA was used as template for PCR as described in BD Biosciences BD SMART RACE cDNA Amplification Kit. Both the heavy and light chain PCR amplifications used the 10×UPM (Universal Primer Mix) provided by the kit as the 5' PCR oligonucleotide. The 3' PCR oligonucleotides were as follows;

```
Mouse kappa
(zc54289: 5'-CGACTGAGCCACCTCCAGATGTTAACTGCTCAC-3'
SEQ ID NO: 28)

Mouse IgG1
(zc54983: 5'-CAGGGGCCAGTGGATAGACAGATGGGGG-3'
SEQ ID NO: 29)

Moue IgG2a
(zc55640: 5'-CAGGGGCCAGTGGATAGACCGATGGGG-3'
SEQ ID NO: 30)
```

The light and heavy chain variable region sequence PCR products were gel purified using GE Healthcare illustrate GFX tm PCR DNA and Gel Band Purification Kit and cloned via Invitrogen TOPO TA Cloning Kit. Eight individual colonies per hybridoma per variable region were screened by colony PCR with M13R and M13F kit primers and submitted for sequencing. Sequencing was performed using ABI PRISM BigDye Terminator v3.0 Cycle Sequencing Kit (Applied Biosystems, Foster City, Calif.). Sequencing reactions were purified using EdgeBioSystems Centriflex Gel Filtration Cartridges (Gaithersburg, Md.) and run on an ABI PRISM 377 DNA Sequencer (Applied Biosystems, Foster City, Calif.). Resultant sequence data was assembled and edited using Sequencher v4.1 software (GeneCodes Corporation, Ann Arbor, Mich.)

Table 1 shows the SEQ ID NO:s for the sequences of the variable regions, which are further described in FIGS. 1-4.

TABLE 1

Sequence Listing Numbers for Variable Light and Variable Heavy Regions

| Clone Number | Light Chain Variable Region SEQ ID NO: | Light Chain Variable Region with signal sequence SEQ ID NO: | Heavy Chain Variable Region SEQ ID NO: | Heavy Chain Variable Region with signal sequence SEQ ID NO: |
|---|---|---|---|---|
| 292.12.3.1 | 8 | 31 | 9 | 32 |
| 292.84.1.6 | 8 with Arg substituted at position 42 | 31 with Arg substituted at position 62 | 9 with substitutions: Thr at position 50; Ser at position 69; Asn at position 77; and Phe at position 95 | 32 with substitutions: Thr at position 50; Ser at position 88; Asn at position 95; and Phe at position 114 |
| 292.63.5.3 | 10 | 33 | 11 | 34 |
| 294.144.3.5 | 12 | 35 | 13 | 36 |
| 292.39.5.3 | 14 | 37 | 15 | 38 |
| 292.51.5.2 | 16 | 39 | 17 | 40 |
| 292.64.6.5.5 | 18 | 41 | 19 | 42 |
| 292.105.4.1 | 20 | 43 | 21 | 44 |
| 292.109.4.4 | 22 | 45 | 23 | 46 |
| 292.118.6.4 | 24 | 47 | 25 | 48 |
| 292.72.3.1 | 26 | 49 | 27 | 50 |

Table 2 shows the SEQ ID NO:s for the sequences of the variable regions, which are further described in FIGS. 1-4.

TABLE 2

Sequence Listing Numbers for CDRs of Variable Light and Variable Heavy Regions

| Clone Number | Variable Heavy CDR1 | Variable Heavy CDR2 | Variable Heavy CDR3 | Variable Light CDR1 | Variable Light CDR2 | Variable Light CDR3 |
|---|---|---|---|---|---|---|
| 292.12.3.1 | SEQ ID NO: 51 (CDR1 VH of 292.12.3.1): RYWMQ | SEQ ID NO: 52: (CDR2 VH of 292.12.3.1): AIYPGDGDT RYSQKFKG | SEQ ID NO: 53: (CDR3 VH of 292.12.3.1): PDGYYAAPY GMDY | SEQ ID NO: 54: (CDR1 VL of 292.12.3.1): RASGNIHNYL A | SEQ ID NO: 55: (CDR2 VL of 292.12.3.1): NAKTLAD | SEQ ID NO: 56: (CDR3 VL of 292.12.3.1): QHFWSTPWT |
| 292.84.1.6 | SEQ ID NO: 51 (CDR1 VH of 292.12.3.1): RYWMQ | SEQ ID NO: 57 (CDR2 VH of 292.84.1.6): TIYPGDGDT RYSQKFKG | SEQ ID NO: 53: (CDR3 VH of 292.12.3.1): PDGYYAAPY GMDY | SEQ ID NO: 54: (CDR1 VL of 292.12.3.1): RASGNIHNYL A | SEQ ID NO: 55: (CDR2 VL of 292.12.3.1): NAKTLAD | SEQ ID NO: 56: (CDR3 VL of 292.12.3.1): QHFWSTPWT |
| 292.72.3.1 | SEQ ID NO: 51 (CDR1 VH of 292.12.3.1): RYWMQ | SEQ ID NO: 58 (CDR2 VH of 292.72.3.1): AIYPRDGDT RYSQKFKG | SEQ ID NO: 59: (CDR3 VH of 292.72.3.1): PDGSYAAPN GMEY | SEQ ID NO: 60: (CDR1 VL of 292.72.3.1): RASGSIHNYL A | SEQ ID NO: 61: (CDR2 VL of 292.72.3.1): NAETLAD | SEQ ID NO: 62: (CDR3 VL of 292.72.3.1): QHFWITPWT |
| 292.63.5.3 | SEQ ID NO: 63 (CDR1 VH of 292.63.5.3): TFIMS | SEQ ID NO: 64 (CDR2 VH of 292.63.5.3): TINSGGYYT FHPDSVKG | SEQ ID NO: 65 (CDR3 VH of 292.63.5.3): QEGWSSAYF SY | SEQ ID NO: 66: (CDR1 VL of 292.63.5.3): KSSQSLLNGS NQKNYLA | SEQ ID NO: 67: (CDR2 VL of 292.63.5.3): FASTRDS | SEQ ID NO: 68: (CDR3 VL of 292.63.5.3): QQHYDTPYT |
| 292.39.5.3 | SEQ ID NO: 69 (CDR1 VH of 292.39.5.3): TYIMS | SEQ ID NO: 70 (CDR2 VH of 292.39.5.3): TINSGGYYT LYPDSVKG | SEQ ID NO: 71 (CDR3 VH of 292.39.5.3): QEGWSSAW FAY | SEQ ID NO: 72: (CDR1 VL of 292.39.5.3): NSSQSLLNSSN QKNYLA | SEQ ID NO: 73: (CDR2 VL of 292.39.5.3): FASTGES | SEQ ID NO: 74: (CDR3 VL of 292.39.5.3): QQHFSTPYT |
| 292.51.5.2 | SEQ ID NO: 75 (CDR1 VH of 292.51.5.2) SFVMS | SEQ ID NO: 76 (CDR2 VH of 292.51.5.2): TINSGGYYS FHPDSVKG | SEQ ID NO: 65 (CDR3 VH of 292.63.5.3): QEGWSSAYF SY | SEQ ID NO: 77 (CDR1 VL of 292.51.5.2): KSSQSLLNSSN QKNYLA | SEQ ID NO: 78 (CDR2 VL of 292.51.5.2): FTSTRES | SEQ ID NO: 68: (CDR3 VL of 292.63.5.3): QQHYDTPYT |

TABLE 2-continued

Sequence Listing Numbers for CDRs of Variable Light and Variable Heavy Regions

| Clone Number | Variable Heavy CDR1 | Variable Heavy CDR2 | Variable Heavy CDR3 | Variable Light CDR1 | Variable Light CDR2 | Variable Light CDR3 |
|---|---|---|---|---|---|---|
| 292.64.6.5.5 | SEQ ID NO: 69 (CDR1 VH of 292.39.5.3): TYIMS | SEQ ID NO: 70 (CDR2 VH of 292.39.5.3): TINSGGYYT LYPDSVKG | SEQ ID NO: 71 (CDR3 VH of 292.39.5.3): QEGWSSAW FAY | SEQ ID NO: 72: (CDR1 VL of 292.39.5.3): NSSQSLLNSSN QKNYLA | SEQ ID NO: 73: (CDR2 VL of 292.39.5.3): FASTGES | SEQ ID NO: 74: (CDR3 VL of 292.39.5.3): QQHFSTPYT |
| 292.105.4.1 | SEQ ID NO: 69 (CDR1 VH of 292.39.5.3): TYIMS | SEQ ID NO: 70 (CDR2 VH of 292.39.5.3): TINSGGYYT LYPDSVKG | SEQ ID NO: 71 (CDR3 VH of 292.39.5.3): QEGWSSAW FAY | SEQ ID NO: 72: (CDR1 VL of 292.39.5.3): NSSQSLLNSSN QKNYLA | SEQ ID NO: 73: (CDR2 VL of 292.39.5.3): FASTGES | SEQ ID NO: 74: (CDR3 VL of 292.39.5.3): QQHFSTPYT |
| 292.109.4.4 | SEQ ID NO: 69 (CDR1 VH of 292.39.5.3): TYIMS | SEQ ID NO: 70 (CDR2 VH of 292.39.5.3): TINSGGYYT LYPDSVKG | SEQ ID NO: 71 (CDR3 VH of 292.39.5.3): QEGWSSAW FAY | SEQ ID NO: 72: (CDR1 VL of 292.39.5.3): NSSQSLLNSSN QKNYLA | SEQ ID NO: 73: (CDR2 VL of 292.39.5.3): FASTGES | SEQ ID NO: 74: (CDR3 VL of 292.39.5.3): QQHFSTPYT |
| 292.118.6.4 | SEQ ID NO: 69 (CDR1 VH of 292.39.5.3): TYIMS | SEQ ID NO: 79 (CDR2 VH of 292.118.6.4): TINSGGYYT IYPDSVKG | SEQ ID NO: 71 (CDR3 VH of 292.39.5.3): QEGWSSAW FAY | SEQ ID NO: 72: (CDR1 VL of 292.39.5.3): NSSQSLLNSSN QKNYLA | SEQ ID NO: 73: (CDR2 VL of 292.39.5.3): FASTGES | SEQ ID NO: 74: (CDR3 VL of 292.39.5.3): QQHFSTPYT |
| 294.144.3.5 | SEQ ID NO: 80 (CDR1 VH of 292.144.3.5): TYWIE | SEQ ID NO: 81 (CDR2 VH of 292.144.3.5): EILPGRGTT NYNAKFQG | SEQ ID NO: 82 (CDR3 VH of 292.144.3.5): ESKLGDDDY | SEQ ID NO: 83: (CDR1 VL of 292.144.3.5): SASSSVSYMH | SEQ ID NO: 84: (CDR2 VL of 292.144.3.5): DTTKLAS | SEQ ID NO: 85: (CDR3 VL of 292.144.3.5): FQGSEHPLT |

Hybridomas, 292.12.3.1 and 292.84.1.6, express light and heavy chains that share extensive sequence identity with each other. The amino acid sequence alignments of the 292.12.3.1 and 292.84.1.6 light chain and heavy chain variable regions are shown in FIG. 2. The high degree of shared sequence identity suggests that the light chain variable regions are derived from the same light chain variable region germline gene, while the heavy chain variable regions are also derived from the same heavy chain variable region germline gene. Additionally, the identity throughout both the light and heavy chain CDR3 and FR4 indicate utilization of the same JL in the light chain, and the same JH and D regions as well as the N and P nucleotide additions in the heavy chain CDR3. Both hybridomas 292.12.3.1 and 292.84.1.6 express kappa light chains, but 292.12.3.1 expresses an IgG1 heavy chain while 292.84.1.6 expresses an IgG2a heavy chain. It appears that both of these hybridomas are derivatives of the same initial B cell immunoglobulin loci rearrangement events and that 292.84.1.6 is a result of a subsequent class switch to an IgG2a heavy chain. Either prior to, or after, the class switch, 292.12.3.1 and 292.84.1.6 diverged by the incorporation of further somatic mutations which led to the single amino acid difference in the light chain and the 4 amino acid differences in the heavy chain.

Example 2

Amino Terminal Protein Sequence Determination

N-terminal protein sequencing was used to determine heavy and light chain antibody sequences. The antibodies were processed with and without pyroglutumate amino peptidase (PGAP) treatment. Untreated samples were processed by addition of 100 picomoles (pmol) protein and water. PGAP treated samples were processed by addition of 100 pmol protein, water, 0.03% SDS, 5×PGAP buffer (Takara Bio Inc., Japan) and PGAP enzyme (1 mU) in 1×PGAP buffer. The PGAP reaction was run for 10 minutes at 95° C. This enzymatic treatment removed the N-terminally blocking pyroglutamic acid groups. Reducing SDS PAGE buffer was added to both the untreated and PGAP treated samples and then the samples were heated for 5 minutes in a boiling water bath. The samples were run on a SDS PAGE gradient gel. The gel was transferred to a PVDF membrane and stained with coomassie blue. Two visible bands were observed for each sample with apparent SDS PAGE molecular weights of 50 kDa and 25 kDa. Each band was excised and subjected to N-terminal protein sequencing. Twenty sequence cycles were run to determine the sequence.

Example 3

Luciferase Assay on Human Transformed Epithelial Cell Lines via Transient Infection with an Adenoviral STAT/SRE Reporter Gene Inhibition, reduction, and/or neutralization of IL-31 activity can be measured by the luciferase assay. For example, human transformed cell lines can be seeded in 96-well flat-bottom plates at 10,000 cell/well in regular growth media as specified for each cell type. The following day, the cells are infected with an adenovirus reporter construct, KZ136, at a multiplicity of infection of 5000. The KZ136 reporter contains the STAT elements in addition to a serum response element. The total volume is 100 ul/well using DMEM supplemented with 2 mM L-glutamine (GibcoBRL), 1 mM Sodium Pyruvate (GibcoBRL) and 1× Insulin-Transferrin-Selenium supplement (GibcoBRL) (hereinafter referred to as serum-free media). Cells are cultured overnight.

The following day, the media is removed and replaced with 100 μl of induction media. The induction media is human IL-31 diluted in serum-free media at 100 ng/ml, 50 ng/ml, 25 ng/ml, 12.5 ng/ml, 6.25 ng/ml, 3.125 ng/ml and 1.56 ng/ml. A positive control of 20% FBS is used to validate the assay and to ensure the infection by adenovirus is successful. The cells are induced for 5 hours at which time the media is aspirated. The cells are then washed in 50 μl/well of PBS, and subsequently lysed in 30 μl/well of 1× cell lysis buffer (Promega). After a 10-minute incubation at room temperature, 25 μl/well of lysate is transferred to opaque white 96-well plates. The plates are then read on the Luminometer using 5-second integration with 40 μl/well injection of luciferase substrate (Promega).

Example 4

IL-31 Bioassay

BAF3 cells transfected with hzCYTOR17 (IL-31RA), hOSMRB, and KZ134 are grown to $5 \times 10^5$ and $1 \times 10^6$ cells/mL. Cells are washed with assay media (RPMI 1640, 10% FBS, L-Glutamine, Sodium Pyruvate, and Pen/Strep (all Gibco)) and resuspended at $3 \times 10^5$ cell/mL in assay medium. In a 96-well opaque plate, mL-31 standards are titered in duplicate from 600 μg/mL to 9.38 pg/mL in assay medium via a 100 μL/well, 1:2 serial dilution. Quality control standards are added in duplicate to the plate at 350 pg/mL and 35 pg/mL in 100 μL. Test samples are often diluted 1:2 or 1:4 and added in duplicate to the sample wells. 100 μL of the washed BAF3 cells are added to each well for a final concentration of $3 \times 10^4$ cells/well. The plate is incubated for 16-24 hours at +37° C. in a 5% $CO_2$ incubator. The plate is centrifuged at 1200 RPM for 5 minutes, media flicked off and 25 μL/well of lysis buffer (Promega) added to each well. After 10 minutes the plate is read on a luminometer (Berthold). The luminometer adds 40 μL/well of luciferase substrate mix (Promega) and integrated the luminescence for a period of 4 seconds. Luminescence values are exported to a spreadsheet where they are analyzed and converted into picograms of IL-31 per $10^6$ cells per mL of volume.

Example 5

IL-31 Involvement in Initiation and Perpetuation of Contact Hyper-Sensitivity In Vivo Method I BALB/c mice are painted on shaved mid-back with 25 ul of 0.5% DNFB dissolved (2,4, dinitro-fluoro-benzene, Sigma, St. Louis Mo.) in acetone:olive oil (4:1) solution using a pipettor. A vehicle control group receives 25 ul of acetone:olive oil only. After 5 days, mice are anaesthetized with isofluorane in an inhalation chamber and both ear pinnae of experimental and control animals are measured with an engineer's micrometer (Mitutoyo) to obtain a baseline measurement. Mice are then challenged by applying 10 ul of 0.25% DNFB in acetone:olive oil (4:1) to both sides of each ear of all mice. Contact hyper-sensitivity is measured at 24 h and 48 h later as the difference between the right ear (challenged) and the left ear (unchallenged). All measurements are done with an engineer's micrometer. Background values are determined by the difference in ear swelling between the challenged and unchallenged ears of naive mice.

Whole blood and serum for FACS and/or ELISA analysis are collected prior to sacrifice and ears are collected for histology.

Method II (Induces Th2 Responses)

BALB/c mice are painted on shaved mid-back with 100 ul of 0.5% FITC (fluorescein isothiocyanate) in a 1:1 solution of acetone/dibutyl phthalate (MSDS available using pipettor on days 1, 2 and 8. On day 13, mice are anaesthetized with isofluorane in an inhalation chamber and both ear pinnae of experimental and control animals are measured with an engineer's micrometer (Mitutoyo) to obtain a baseline measurement. Mice are challenged by applying 25 ul of 0.5% FITC (in 1:1 acetone/dibutyl phthalate) to the dorsal surface of each ear. Contact hyper-sensitivity is measured at 24 h and 48 h later as the difference between the right ear (challenged) and the left ear (unchallenged). All measurements are done with an engineer's micrometer. Background values are determined by the difference in ear swelling between the challenged and unchallenged ears of naive mice. Whole blood and serum for FACS and/or ELISA analysis are collected prior to sacrifice and ears are collected for histology.

Method III (Induces Th1 Responses)

BALB/c mice are painted on shaved mid-back with 25 ul of 2% oxazalone (in 4:1 acetone/olive oil) using pipettor. On day 7, mice are anaesthetized with isofluorane in an inhalation chamber and both ear pinnae of experimental and control animals are measured with an engineer's micrometer (Mitutoyo) to obtain a baseline measurement. Mice are challenged by applying 8 ul of oxazalone to the dorsal surface of each ear. Contact hyper-sensitivity is measured at 24 h and 48 h later as the difference between the right ear (challenged) and the left ear (unchallenged). All measurements are done with an engineer's micrometer. Background values are determined by the difference in ear swelling between the challenged and unchallenged ears of naive mice. Whole blood and serum for FACS and/or ELISA analysis are collected prior to sacrifice and ears are collected for histology.

Involvement of IL-31 in the initiation and perpetuation of contact hyper-sensitivity is tested using the IL-31 binding molecules or IL-31 antagonists described herein against IL-31 both at the sensitization and challenge phases of the experiment.

Example 6

IL-31 Involvement in Atopic Dermatitis In Vivo

Methods I (Sensitization of NC/Nga mice)

weeks old male NC/Nga mice (CRL, Japan) are housed in SPF quarantine conditions for 4 weeks to acclimate. The mice are approximately 10-11 weeks old at the start of the antigen sensitization. Mice are anaesthetized with isofluorane and backs rae shaved with electric clippers. Approximately 10 ug of *Dermatophagoides pteronyssinus* (Dp) (Indoor Biotechnologies, special order) extract is injected intradermally at the nape of the neck 3 times per week for 5 to 6 weeks until mice developed skin lesions. Control animals receive 1oul PBS intradermal injections 3 times per week. The Dp extract is prepared according to method by Matsuoka and colleagues. Matsuoka H., et al., *Allergy:* 58, 139 (2003). Briefly, 595 mg Dp lyophilized spent culture extract is dissolved in 12 mL sterile PBS (Gibco). Dp is mixed in a 50 mL Falcon tube on a shaking rocker for 30 minutes. The extract is spun for 10 minutes at 2000 rpm and the supernatant is collected and aliquoted into 1 mL cryovial tubes and stored at −20° C.

The effects of IL-31 binding molecules or IL-31 antagonists are measured by inhibition of scratching, itching, and or dermatitis.

Methods II (Sensitization of DO11.10 Mice)

DO1.10 transgenic mice are bred from an in-house colony and are between 9.5 and 14 weeks old at start of antigen sensitization. 24 hours prior to epicutaneous sensitization mice are anaesthetized with isofluorane and the entire trunk (back and abdomen) of mice are shaved with electric clippers. The mice are then tape stripped with Elastin surgical tape (Johnson and Johnson) on the back. 1 cm2 sterile gauze patches are wetted with either 500 ug ovalbumin (Calbiochem 32467) or sterile PBS (Gibco) and adhered to left backside of mice with DuoDerm Extra Thin Dressing (ConvaTec 187932). The patch and dressing are then covered in a body wrap of the Elastin surgical tape so mice could not remove or destroy the patches. Patches are worn for 7 days and removed. The mice are rested for two weeks before having another round of epicutaneous sensitization. Mice receive a total of three one-week sensitizations.

The effects of IL-31 binding molecules or IL-31 antagonists are measured by inhibition of scratching, itching, and or dermatitis and/or a reduction in IL-31RA expression in keratinocytes.

Example 7

Reduction of TARC and MDC in Response to anti-Il-31 Antibody in AD Mouse Models

Method I

Six-week old male NC/Nga mice (CRL Japan) are sensitized intradermally with 50 μg dust mite extract (*D. pteronyssinus*, Indoor Biotechnologies) three times a week on the back and scored for AD-like lesions. After 5 weeks of sensitization the mice are euthanized and the right ears were excised and placed into a single well of a 48-well culture dish (Corning) supplemented with RPMI+2% FBS (GIBCO Invitrogen). Plates are placed in 5% CO2 humidity controlled incubators. Supernatants are collected after 24 hours and frozen at −20° C. until further analysis.

Method II

Twelve-week old female NC/Nga mice (CRL Japan) are sensitized intradermally with 10 μg SEB (Toxin Technology) in the ear and on the back three times per week. The mice are scored for AD-like lesions. After 5 weeks of sensitization the mice are euthanized and 6 mm biopsy punches were taken from the injected ear of each mouse and placed into a single well of a 48-well culture dish supplemented with RPMI+2% FBS. Plates were placed in 5% CO2 humidity controlled incubators. Supernatants are collected after 24 hours and frozen at −20° C. until further analysis.

Groups of mice in both studies are treated with IL-31 binding molecules or IL-31 antagonists intraperitoneally two times each week starting after 1 to 2 weeks of sensitization. TARC and MDC concentrations in the 24-hour supernatant samples are measured by conventional ELISA (R&D Systems).

Example 8

Administration of IL-31 Neutralizing Antibody

Normal female BALB/c mice (CRL) approximately 8 to 12 weeks old are implanted subcutaneously with 14-day osmotic pumps (Alzet, #2002) delivering 1 ug/day mIL-31. Groups of mice receive intraperitoneal (i.p.) injections of rat anti-mouse IL-31 monoclonal antibody 10 mg/kg (200 ug/mouse) twice weekly starting 1 week prior to IL-31 delivery. Control groups of mice receive i.p. injections of vehicle (PBS/0.1% BSA) with the identical dosing schedules. Mice are scored daily for alopecia and pruritis using the following criteria: 0=no scratching, animal appears normal, 1=thinning of coat in small areas, scratching noted, 2=minor hair loss (small patches), scratching, 3=moderate hair loss, scratching, and 4=severe hair loss, excessive scratching.

The effects of IL-31 binding molecules or IL-31 antagonists are measured by a delay in onset of symptoms of approximately 5 to 7 days and a lower overall score for alopecia and pruritis.

Example 9

Expression of Recombinant Chimeric Anti-Human IL-31 Monoclonal Antibodies

The heavy and light chain variable region sequences from two separate mouse anti-human IL31 monoclonal antibodies, 292.12.3.1 and 292.63.5.3, were obtained by PCR. The DNA sequences were determined and expression constructs were generated utilizing human constant region DNA sequences.

The light chain expression constructs consisted of a hybrid MPSV/CMV promoter/enhancer directing expression of the chimeric mouse anti-human IL31 variable region fused to a human immunoglobulin kappa constant region.

The heavy chain expression constructs consisted of a hybrid MPSV/CMV promoter/enhancer directing expression of the chimeric mouse anti-human IL31 variable region fused to a human immunoglobulin IgG4 constant region with an amino acid substitution in the hinge region, Serine 228 changed to Proline.

The light and heavy chain expression constructs encoding the chimeric light and heavy chains from each hybridoma were co-transfected into HEK 293F cells. Conditioned media was harvested after 4 days. Western blot analysis demonstrated intact chimeric antibody of expected size on non-reducing SDS-PAGE.

The antigen binding ability of the chimeric antibodies were determined by an ELISA based protocol to measure apparent EC50 (effective concentration to bind 50% of antigen at a fixed concentration). The assay format utilized a goat anti-human Fc immobilization for capture of human monoclonal antibodies from unprocessed cell culture conditioned media. A dilution series of biotinylated IL31 tested the "C" parameter of a 4-parameter fit which results in the apparent Kd (or EC50) in either ng/mL or nM of IL31. The assay sensitivity is high enough that dilute monoclonal antibody or chimeric antibody cell culture conditioned media can be evaluated. The Kd determined by this method generally approaches the Kd measured for purified, homogeneous monoclonal antibodies measured using Biacore. Both chimeric anti-IL31 antibodies showed similar EC50 values compared to the control "parental" mouse hybridoma monoclonal antibody 292.63.5.3 as shown in Table 3.

TABLE 3

EC50 Determination of Conditioned Media from HEK 293F Transient Transfections

| Sample | EC50 (ng/mL)[a] | EC50 (nM)[a] |
| --- | --- | --- |
| Chimeric 292.63.5.3 | 1.3 | 0.08 |
| Chimeric 292.12.3.1 | 2.0 | 0.12 |
| Non-transfected HEK 293F control medium | No binding | No binding |

TABLE 3-continued

EC50 Determination of Conditioned Media from HEK 293F Transient Transfections

| Sample | EC50 (ng/mL)[a] | EC50 (nM)[a] |
| --- | --- | --- |
| 292.63.5.3 (Lot E9289) Control monoclonal antibody | 4.3 | 0.26 |

[a]Average from duplicate measure

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated monoclonal antibody or antigen-binding fragment thereof that is capable of specifically binding to a polypeptide consisting of amino acid residues 27-164 of SEQ ID NO: 2, wherein the monoclonal antibody or antigen-binding fragment comprises a light chain variable region having the amino acid sequence of SEQ ID NO:8 and a heavy chain variable region having the amino acid sequence of SEQ ID NO:9; and
   wherein the monoclonal antibody or antigen-binding fragment further comprises a human IgG4 Fc molecule.

2. The monoclonal antibody or antigen-binding fragment according to claim 1, wherein the monoclonal antibody or antigen-binding fragment inhibits signaling by the polypeptide through IL-31RA (SEQ ID NO:5).

3. The monoclonal antibody or antigen-binding fragment according to claim 1, wherein the monoclonal antibody or antigen-binding fragment is selected from the group consisting of:
   (a) a murine monoclonal antibody or antibody-binding fragment; and
   (b) a humanized antibody or antibody-binding fragment.

4. A method of reducing IL-31-induced pruritis in a mammal comprising administering to the mammal a therapeutically effective amount of the monoclonal antibody or antigen-binding fragment thereof according to claim 3, wherein after administration the pruritis is reduced.

5. A method of reducing IL-31-induced pruritis in a mammal comprising administering to the mammal a therapeutically effective amount of a composition comprising the monoclonal antibody or antigen-binding fragment thereof according to claim 3, and a pharmaceutically acceptable carrier, wherein after administration the pruritis is reduced.

6. A method of reducing IL-31-induced inflammation in a mammal comprising administering to the mammal a therapeutically effective amount of the monoclonal antibody or antigen-binding fragment thereof according to claim 3, wherein after administration the inflammation is reduced.

7. A method of reducing IL-31-induced inflammation in a mammal comprising administering to the mammal a therapeutically effective amount of a composition comprising the monoclonal antibody or antigen-binding fragment thereof according to claim 3, and a pharmaceutically acceptable carrier, wherein after administration the inflammation is reduced.

8. A method of reducing IL-31-induced scratching in a mammal comprising administering to the mammal a therapeutically effective amount of the monoclonal antibody or antigen-binding fragment thereof according to claim 3, wherein after administration the scratching is reduced.

9. A method of reducing IL-31-induced scratching in a mammal comprising administering to the mammal a therapeutically effective amount of a composition comprising the monoclonal antibody or antigen-binding fragment thereof according to claim 3, and a pharmaceutically acceptable carrier, wherein after administration the scratching is reduced.

* * * * *

SEQUENCE LISTING

```
<160> NUMBER OF SEQ ID NOS: 90

<210> SEQ ID NO 1
<211> LENGTH: 904
<212> TYPE: DNA
<213> ORGANISM: Homo sapiens
<220> FEATURE:
<221> NAME/KEY: CDS
<222> LOCATION: (28)..(519)

<400> SEQUENCE: 1
ctgaagctgg ccttgctctc tctcgcc atg gcc tct cac tca ggc ccc tcg acg        54
                                Met Ala Ser His Ser Gly Pro Ser Thr
                                 1               5 tct gtg ctc ttt ctg ttc tgc tgc ctg gga ggc tgg ctg gcc tcc cac        102
Ser Val Leu Phe Leu Phe Cys Cys Leu Gly Gly Trp Leu Ala Ser His
 10              15                  20                  25 acg ttg ccc gtc cgt tta cta cga cca agt gat gat gta cag aaa ata        150
Thr Leu Pro Val Arg Leu Leu Arg Pro Ser Asp Asp Val Gln Lys Ile
                 30                  35                  40 gtc gag gaa tta cag tcc ctc tcg aag atg ctt ttg aaa gat gtg gag        198
Val Glu Glu Leu Gln Ser Leu Ser Lys Met Leu Leu Lys Asp Val Glu
             45                  50                  55 gaa gag aag ggc gtg ctc gtg tcc cag aat tac acg ctg ccg tgt ctc        246
Glu Glu Lys Gly Val Leu Val Ser Gln Asn Tyr Thr Leu Pro Cys Leu
         60                  65                  70 agc cct gac gcc cag ccg cca aac aac atc cac agc cca gcc atc cgg        294
Ser Pro Asp Ala Gln Pro Pro Asn Asn Ile His Ser Pro Ala Ile Arg
 75                  80                  85 gca tat ctc aag aca atc aga cag cta gac aac aaa tct gtt att gat        342
Ala Tyr Leu Lys Thr Ile Arg Gln Leu Asp Asn Lys Ser Val Ile Asp
 90                  95                 100                 105 gag atc ata gag cac ctc gac aaa ctc ata ttt caa gat gca cca gaa        390
Glu Ile Ile Glu His Leu Asp Lys Leu Ile Phe Gln Asp Ala Pro Glu
                110                 115                 120 aca aac att tct gtg cca aca gac acc cat gaa tgt aaa cgc ttc atc        438
Thr Asn Ile Ser Val Pro Thr Asp Thr His Glu Cys Lys Arg Phe Ile
                125                 130                 135 ctg act att tct caa cag ttt tca gag tgc atg gac ctc gca cta aaa        486
Leu Thr Ile Ser Gln Gln Phe Ser Glu Cys Met Asp Leu Ala Leu Lys
                140                 145                 150 tca ttg acc tct gga gcc caa cag gcc acc act taaggccatc tcttcctttc      539
Ser Leu Thr Ser Gly Ala Gln Gln Ala Thr Thr
                155                 160
```

-continued

```
ggattggcag gaacttaagg agccttaaaa agatgaccga cagctaagtg tgggaactct    599
gccgtgattc cttaagtaca ttttccaat gaataatctc agggacccct catatgggct    659
agtcccggga gggctgagat gtgaatttgt gaattacctt gaaaaacatt aggttattgt    719
tattagtctt ggtattttatg gaatgctttt cttctgcagg cttaagtctt acttattata    779
ccctcgtgag ggtgggaggt ggcagctatg ttaatttatt gatatttatt gtactaagag    839
ttgtcaatgc tccctggggg agccctcgga atctatttaa taaattatat tgaattttc    899
tcata    904
```

<210> SEQ ID NO 2
<211> LENGTH: 164
<212> TYPE: PRT
<213> ORGANISM: Homo sapiens

<400> SEQUENCE: 2

```
Met Ala Ser His Ser Gly Pro Ser Thr Ser Val Leu Phe Leu Phe Cys
1               5                   10                  15

Cys Leu Gly Gly Trp Leu Ala Ser His Thr Leu Pro Val Arg Leu Leu
            20                  25                  30

Arg Pro Ser Asp Asp Val Gln Lys Ile Val Glu Glu Leu Gln Ser Leu
        35                  40                  45

Ser Lys Met Leu Leu Lys Asp Val Glu Glu Lys Gly Val Leu Val
    50                  55                  60

Ser Gln Asn Tyr Thr Leu Pro Cys Leu Ser Pro Asp Ala Gln Pro Pro
65                  70                  75                  80

Asn Asn Ile His Ser Pro Ala Ile Arg Ala Tyr Leu Lys Thr Ile Arg
                85                  90                  95

Gln Leu Asp Asn Lys Ser Val Ile Asp Glu Ile Glu His Leu Asp
            100                 105                 110

Lys Leu Ile Phe Gln Asp Ala Pro Glu Thr Asn Ile Ser Val Pro Thr
        115                 120                 125

Asp Thr His Glu Cys Lys Arg Phe Ile Leu Thr Ile Ser Gln Gln Phe
    130                 135                 140

Ser Glu Cys Met Asp Leu Ala Leu Lys Ser Leu Thr Ser Gly Ala Gln
145                 150                 155                 160

Gln Ala Thr Thr
```

<210> SEQ ID NO 3
<211> LENGTH: 755
<212> TYPE: DNA
<213> ORGANISM: Mus musculus
<220> FEATURE:
<221> NAME/KEY: CDS
<222> LOCATION: (1)..(489)

<400> SEQUENCE: 3

```
atg atc ttc cac aca gga aca acg aag cct acc ctg gtg ctg ctt tgc    48
Met Ile Phe His Thr Gly Thr Thr Lys Pro Thr Leu Val Leu Leu Cys
1               5                   10                  15 tgt ata gga acc tgg ctg gcc acc tgc agc ttg tcc ttc ggt gcc cca    96
Cys Ile Gly Thr Trp Leu Ala Thr Cys Ser Leu Ser Phe Gly Ala Pro
            20                  25                  30 ata tcg aag gaa gac tta aga act aca att gac ctc ttg aaa caa gag   144
Ile Ser Lys Glu Asp Leu Arg Thr Thr Ile Asp Leu Leu Lys Gln Glu
        35                  40                  45 tct cag gat ctt tat aac aac tat agc ata aag cag gca tct ggg atg   192
Ser Gln Asp Leu Tyr Asn Asn Tyr Ser Ile Lys Gln Ala Ser Gly Met
    50                  55                  60
```

```
tca gca gac gaa tca ata cag ctg ccg tgt ttc agc ctg gac cgg gaa       240
Ser Ala Asp Glu Ser Ile Gln Leu Pro Cys Phe Ser Leu Asp Arg Glu
 65                  70                  75                  80 gca tta acc aac atc tcg gtc atc ata gca cat ctg gag aaa gtc aaa       288
Ala Leu Thr Asn Ile Ser Val Ile Ile Ala His Leu Glu Lys Val Lys
                 85                  90                  95 gtg ttg agc gag aac aca gta gat act tct tgg gta ata aga tgg cta       336
Val Leu Ser Glu Asn Thr Val Asp Thr Ser Trp Val Ile Arg Trp Leu
            100                 105                 110 aca aac atc agc tgt ttc aac cca ctg aat tta aac att tct gtg cct       384
Thr Asn Ile Ser Cys Phe Asn Pro Leu Asn Leu Asn Ile Ser Val Pro
        115                 120                 125 gga aat act gat gaa tcc tat gat tgt aaa gtg ttc gtg ctt acg gtt       432
Gly Asn Thr Asp Glu Ser Tyr Asp Cys Lys Val Phe Val Leu Thr Val
    130                 135                 140 tta aag cag ttc tca aac tgc atg gca gaa ctg cag gct aag gac aat       480
Leu Lys Gln Phe Ser Asn Cys Met Ala Glu Leu Gln Ala Lys Asp Asn
145                 150                 155                 160 act aca tgc tgagtgatgg ggggggggg ggtgcagtgt cctcagcagt                529
Thr Thr Cys gcctgtcctt cgagggctga gcttgcaacc caggacttaa ctccaaaggg actgtgcggt     589
cattactagt catgttattt atgttttat tttgtccact gaaatcttgt tctgctaccc      649
tgtagggact ggaagtggca gctatattta tttatttatg tactgagttt gttaacgctc     709
catggaggag ccttcagagt ctatttaata aattatattg acatga                    755

<210> SEQ ID NO 4
<211> LENGTH: 163
<212> TYPE: PRT
<213> ORGANISM: Mus musculus

<400> SEQUENCE: 4

Met Ile Phe His Thr Gly Thr Thr Lys Pro Thr Leu Val Leu Leu Cys
 1               5                  10                  15

Cys Ile Gly Thr Trp Leu Ala Thr Cys Ser Leu Ser Phe Gly Ala Pro
                20                  25                  30

Ile Ser Lys Glu Asp Leu Arg Thr Thr Ile Asp Leu Leu Lys Gln Glu
            35                  40                  45

Ser Gln Asp Leu Tyr Asn Asn Tyr Ser Ile Lys Gln Ala Ser Gly Met
        50                  55                  60

Ser Ala Asp Glu Ser Ile Gln Leu Pro Cys Phe Ser Leu Asp Arg Glu
 65                  70                  75                  80

Ala Leu Thr Asn Ile Ser Val Ile Ile Ala His Leu Glu Lys Val Lys
                 85                  90                  95

Val Leu Ser Glu Asn Thr Val Asp Thr Ser Trp Val Ile Arg Trp Leu
            100                 105                 110

Thr Asn Ile Ser Cys Phe Asn Pro Leu Asn Leu Asn Ile Ser Val Pro
        115                 120                 125

Gly Asn Thr Asp Glu Ser Tyr Asp Cys Lys Val Phe Val Leu Thr Val
    130                 135                 140

Leu Lys Gln Phe Ser Asn Cys Met Ala Glu Leu Gln Ala Lys Asp Asn
145                 150                 155                 160

Thr Thr Cys

<210> SEQ ID NO 5
<211> LENGTH: 662
<212> TYPE: PRT
```

<213> ORGANISM: Homo sapiens

<400> SEQUENCE: 5

Met Lys Leu Ser Pro Gln Pro Ser Cys Val Asn Leu Gly Met Met Trp
1               5                   10                  15

Thr Trp Ala Leu Trp Met Leu Pro Ser Leu Cys Lys Phe Ser Leu Ala
            20                  25                  30

Ala Leu Pro Ala Lys Pro Glu Asn Ile Ser Cys Val Tyr Tyr Tyr Arg
        35                  40                  45

Lys Asn Leu Thr Cys Thr Trp Ser Pro Gly Lys Glu Thr Ser Tyr Thr
50                  55                  60

Gln Tyr Thr Val Lys Arg Thr Tyr Ala Phe Gly Glu Lys His Asp Asn
65                  70                  75                  80

Cys Thr Thr Asn Ser Ser Thr Ser Glu Asn Arg Ala Ser Cys Ser Phe
                85                  90                  95

Phe Leu Pro Arg Ile Thr Ile Pro Asp Asn Tyr Thr Ile Glu Val Glu
            100                 105                 110

Ala Glu Asn Gly Asp Gly Val Ile Lys Ser His Met Thr Tyr Trp Arg
        115                 120                 125

Leu Glu Asn Ile Ala Lys Thr Glu Pro Pro Lys Ile Phe Arg Val Lys
130                 135                 140

Pro Val Leu Gly Ile Lys Arg Met Ile Gln Ile Glu Trp Ile Lys Pro
145                 150                 155                 160

Glu Leu Ala Pro Val Ser Ser Asp Leu Lys Tyr Thr Leu Arg Phe Arg
                165                 170                 175

Thr Val Asn Ser Thr Ser Trp Met Glu Val Asn Phe Ala Lys Asn Arg
            180                 185                 190

Lys Asp Lys Asn Gln Thr Tyr Asn Leu Thr Gly Leu Gln Pro Phe Thr
        195                 200                 205

Glu Tyr Val Ile Ala Leu Arg Cys Ala Val Lys Glu Ser Lys Phe Trp
210                 215                 220

Ser Asp Trp Ser Gln Glu Lys Met Gly Met Thr Glu Glu Ala Pro
225                 230                 235                 240

Cys Gly Leu Glu Leu Trp Arg Val Leu Lys Pro Ala Glu Ala Asp Gly
                245                 250                 255

Arg Arg Pro Val Arg Leu Leu Trp Lys Lys Ala Arg Gly Ala Pro Val
            260                 265                 270

Leu Glu Lys Thr Leu Gly Tyr Asn Ile Trp Tyr Tyr Pro Glu Ser Asn
        275                 280                 285

Thr Asn Leu Thr Glu Thr Met Asn Thr Thr Asn Gln Gln Leu Glu Leu
290                 295                 300

His Leu Gly Gly Glu Ser Phe Trp Val Ser Met Ile Ser Tyr Asn Ser
305                 310                 315                 320

Leu Gly Lys Ser Pro Val Ala Thr Leu Arg Ile Pro Ala Ile Gln Glu
                325                 330                 335

Lys Ser Phe Gln Cys Ile Glu Val Met Gln Ala Cys Val Ala Glu Asp
            340                 345                 350

Gln Leu Val Val Lys Trp Gln Ser Ser Ala Leu Asp Val Asn Thr Trp
        355                 360                 365

Met Ile Glu Trp Phe Pro Asp Val Asp Ser Glu Pro Thr Thr Leu Ser
370                 375                 380

Trp Glu Ser Val Ser Gln Ala Thr Asn Trp Thr Ile Gln Gln Asp Lys
385                 390                 395                 400

Leu Lys Pro Phe Trp Cys Tyr Asn Ile Ser Val Tyr Pro Met Leu His

```
                    405                 410                 415
Asp Lys Val Gly Glu Pro Tyr Ser Ile Gln Ala Tyr Ala Lys Glu Gly
            420                 425                 430

Val Pro Ser Glu Gly Pro Glu Thr Lys Val Glu Asn Ile Gly Val Lys
        435                 440                 445

Thr Val Thr Ile Thr Trp Lys Glu Ile Pro Lys Ser Glu Arg Lys Gly
450                 455                 460

Ile Ile Cys Asn Tyr Thr Ile Phe Tyr Gln Ala Glu Gly Gly Lys Gly
465                 470                 475                 480

Phe Ser Lys Thr Val Asn Ser Ser Ile Leu Gln Tyr Gly Leu Glu Ser
            485                 490                 495

Leu Lys Arg Lys Thr Ser Tyr Ile Val Gln Val Met Ala Ser Thr Ser
        500                 505                 510

Ala Gly Gly Thr Asn Gly Thr Ser Ile Asn Phe Lys Thr Leu Ser Phe
    515                 520                 525

Ser Val Phe Glu Ile Ile Leu Ile Thr Ser Leu Ile Gly Gly Gly Leu
        530                 535                 540

Leu Ile Leu Ile Ile Leu Thr Val Ala Tyr Gly Leu Lys Lys Pro Asn
545                 550                 555                 560

Lys Leu Thr His Leu Cys Trp Pro Thr Val Pro Asn Pro Ala Glu Ser
            565                 570                 575

Ser Ile Ala Thr Trp His Gly Asp Asp Phe Lys Asp Lys Leu Asn Leu
        580                 585                 590

Lys Glu Ser Asp Asp Ser Val Asn Thr Glu Asp Arg Ile Leu Lys Pro
    595                 600                 605

Cys Ser Thr Pro Ser Asp Lys Leu Val Ile Asp Lys Leu Val Val Asn
        610                 615                 620

Phe Gly Asn Val Leu Gln Glu Ile Phe Thr Asp Glu Ala Arg Thr Gly
625                 630                 635                 640

Gln Glu Asn Asn Leu Gly Gly Glu Lys Asn Gly Thr Arg Ile Leu Ser
            645                 650                 655

Ser Cys Pro Thr Ser Ile
            660

<210> SEQ ID NO 6
<211> LENGTH: 979
<212> TYPE: PRT
<213> ORGANISM: Homo sapiens

<400> SEQUENCE: 6

Met Ala Leu Phe Ala Val Phe Gln Thr Thr Phe Phe Leu Thr Leu Leu
1               5                   10                  15

Ser Leu Arg Thr Tyr Gln Ser Glu Val Leu Ala Glu Arg Leu Pro Leu
            20                  25                  30

Thr Pro Val Ser Leu Lys Val Ser Thr Asn Ser Thr Arg Gln Ser Leu
        35                  40                  45

His Leu Gln Trp Thr Val His Asn Leu Pro Tyr His Gln Glu Leu Lys
    50                  55                  60

Met Val Phe Gln Ile Gln Ile Ser Arg Ile Glu Thr Ser Asn Val Ile
65                  70                  75                  80

Trp Val Gly Asn Tyr Ser Thr Thr Val Lys Trp Asn Gln Val Leu His
            85                  90                  95

Trp Ser Trp Glu Ser Glu Leu Pro Leu Glu Cys Ala Thr His Phe Val
        100                 105                 110

Arg Ile Lys Ser Leu Val Asp Asp Ala Lys Phe Pro Glu Pro Asn Phe
```

```
                115               120               125
Trp Ser Asn Trp Ser Ser Trp Glu Glu Val Ser Val Gln Asp Ser Thr
130               135               140
Gly Gln Asp Ile Leu Phe Val Phe Pro Lys Asp Lys Leu Val Glu Glu
145               150               155               160
Gly Thr Asn Val Thr Ile Cys Tyr Val Ser Arg Asn Ile Gln Asn Asn
                165               170               175
Val Ser Cys Tyr Leu Glu Gly Lys Gln Ile His Gly Glu Gln Leu Asp
            180               185               190
Pro His Val Thr Ala Phe Asn Leu Asn Ser Val Pro Phe Ile Arg Asn
        195               200               205
Lys Gly Thr Asn Ile Tyr Cys Glu Ala Ser Gln Gly Asn Val Ser Glu
210               215               220
Gly Met Lys Gly Ile Val Leu Phe Val Ser Lys Val Leu Glu Glu Pro
225               230               235               240
Lys Asp Phe Ser Cys Glu Thr Glu Asp Phe Lys Thr Leu His Cys Thr
                245               250               255
Trp Asp Pro Gly Thr Asp Thr Ala Leu Gly Trp Ser Lys Gln Pro Ser
            260               265               270
Gln Ser Tyr Thr Leu Phe Glu Ser Phe Ser Gly Glu Lys Lys Leu Cys
        275               280               285
Thr His Lys Asn Trp Cys Asn Trp Gln Ile Thr Gln Asp Ser Gln Glu
290               295               300
Thr Tyr Asn Phe Thr Leu Ile Ala Glu Asn Tyr Leu Arg Lys Arg Ser
305               310               315               320
Val Asn Ile Leu Phe Asn Leu Thr His Arg Val Tyr Leu Met Asn Pro
                325               330               335
Phe Ser Val Asn Phe Glu Asn Val Asn Ala Thr Asn Ala Ile Met Thr
            340               345               350
Trp Lys Val His Ser Ile Arg Asn Asn Phe Thr Tyr Leu Cys Gln Ile
        355               360               365
Glu Leu His Gly Glu Gly Lys Met Met Gln Tyr Asn Val Ser Ile Lys
370               375               380
Val Asn Gly Glu Tyr Phe Leu Ser Glu Leu Glu Pro Ala Thr Glu Tyr
385               390               395               400
Met Ala Arg Val Arg Cys Ala Asp Ala Ser His Phe Trp Lys Trp Ser
                405               410               415
Glu Trp Ser Gly Gln Asn Phe Thr Thr Leu Glu Ala Ala Pro Ser Glu
            420               425               430
Ala Pro Asp Val Trp Arg Ile Val Ser Leu Glu Pro Gly Asn His Thr
        435               440               445
Val Thr Leu Phe Trp Lys Pro Leu Ser Lys Leu His Ala Asn Gly Lys
450               455               460
Ile Leu Phe Tyr Asn Val Val Glu Asn Leu Asp Lys Pro Ser Ser Ser
465               470               475               480
Ser Glu Leu His Ser Ile Pro Ala Pro Ala Asn Ser Thr Lys Leu Ile
                485               490               495
Leu Asp Arg Cys Ser Tyr Gln Ile Cys Val Ile Ala Asn Asn Ser Val
            500               505               510
Gly Ala Ser Pro Ala Ser Val Ile Val Ile Ser Ala Asp Pro Glu Asn
        515               520               525
Lys Glu Val Glu Glu Arg Ile Ala Gly Thr Glu Gly Gly Phe Ser
530               535               540
```

-continued

```
Leu Ser Trp Lys Pro Gln Pro Gly Asp Val Ile Gly Tyr Val Val Asp
545                 550                 555                 560

Trp Cys Asp His Thr Gln Asp Val Leu Gly Asp Phe Gln Trp Lys Asn
                565                 570                 575

Val Gly Pro Asn Thr Thr Ser Thr Val Ile Ser Thr Asp Ala Phe Arg
            580                 585                 590

Pro Gly Val Arg Tyr Asp Phe Arg Ile Tyr Gly Leu Ser Thr Lys Arg
        595                 600                 605

Ile Ala Cys Leu Leu Glu Lys Lys Thr Gly Tyr Ser Gln Glu Leu Ala
610                 615                 620

Pro Ser Asp Asn Pro His Val Leu Val Asp Thr Leu Thr Ser His Ser
625                 630                 635                 640

Phe Thr Leu Ser Trp Lys Asp Tyr Ser Thr Glu Ser Gln Pro Gly Phe
                645                 650                 655

Ile Gln Gly Tyr His Val Tyr Leu Lys Ser Lys Ala Arg Gln Cys His
            660                 665                 670

Pro Arg Phe Glu Lys Ala Val Leu Ser Asp Gly Ser Glu Cys Cys Lys
        675                 680                 685

Tyr Lys Ile Asp Asn Pro Glu Glu Lys Ala Leu Ile Val Asp Asn Leu
690                 695                 700

Lys Pro Glu Ser Phe Tyr Glu Phe Phe Ile Thr Pro Phe Thr Ser Ala
705                 710                 715                 720

Gly Glu Gly Pro Ser Ala Thr Phe Thr Lys Val Thr Thr Pro Asp Glu
                725                 730                 735

His Ser Ser Met Leu Ile His Ile Leu Leu Pro Met Val Phe Cys Val
            740                 745                 750

Leu Leu Ile Met Val Met Cys Tyr Leu Lys Ser Gln Trp Ile Lys Glu
        755                 760                 765

Thr Cys Tyr Pro Asp Ile Pro Asp Pro Tyr Lys Ser Ser Ile Leu Ser
770                 775                 780

Leu Ile Lys Phe Lys Glu Asn Pro His Leu Ile Ile Met Asn Val Ser
785                 790                 795                 800

Asp Cys Ile Pro Asp Ala Ile Glu Val Val Ser Lys Pro Glu Gly Thr
                805                 810                 815

Lys Ile Gln Phe Leu Gly Thr Arg Lys Ser Leu Thr Glu Thr Glu Leu
            820                 825                 830

Thr Lys Pro Asn Tyr Leu Tyr Leu Leu Pro Thr Glu Lys Asn His Ser
        835                 840                 845

Gly Pro Gly Pro Cys Ile Cys Phe Glu Asn Leu Thr Tyr Asn Gln Ala
850                 855                 860

Ala Ser Asp Ser Gly Ser Cys Gly His Val Pro Val Ser Pro Lys Ala
865                 870                 875                 880

Pro Ser Met Leu Gly Leu Met Thr Ser Pro Glu Asn Val Leu Lys Ala
                885                 890                 895

Leu Glu Lys Asn Tyr Met Asn Ser Leu Gly Glu Ile Pro Ala Gly Glu
            900                 905                 910

Thr Ser Leu Asn Tyr Val Ser Gln Leu Ala Ser Pro Met Phe Gly Asp
        915                 920                 925

Lys Asp Ser Leu Pro Thr Asn Pro Val Glu Ala Pro His Cys Ser Glu
930                 935                 940

Tyr Lys Met Gln Met Ala Val Ser Leu Arg Leu Ala Leu Pro Pro Pro
945                 950                 955                 960

Thr Glu Asn Ser Ser Leu Ser Ser Ile Thr Leu Leu Asp Pro Gly Glu
                965                 970                 975
```

His Tyr Cys

<210> SEQ ID NO 7
<211> LENGTH: 6
<212> TYPE: PRT
<213> ORGANISM: Artificial Sequence
<220> FEATURE:
<223> OTHER INFORMATION: Glu-Glu tag peptide

<400> SEQUENCE: 7

Glu Tyr Met Pro Met Glu
1               5

<210> SEQ ID NO 8
<211> LENGTH: 107
<212> TYPE: PRT
<213> ORGANISM: Mus musculus
<220> FEATURE:
<221> NAME/KEY: VARIANT
<222> LOCATION: (42)..(42)
<223> OTHER INFORMATION: Xaa is Lys or Arg

<400> SEQUENCE: 8

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Xaa Ser Pro Gln Leu Leu Val
        35                  40                  45

Tyr Asn Ala Lys Thr Leu Ala Asp Gly Val Pro Ser Arg Phe Ser Gly
    50                  55                  60

Ser Arg Ser Glu Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro Trp
                85                  90                  95

Thr Phe Gly Gly Gly Thr Lys Leu Glu Ile Lys
            100                 105

<210> SEQ ID NO 9
<211> LENGTH: 122
<212> TYPE: PRT
<213> ORGANISM: Mus musculus
<220> FEATURE:
<221> NAME/KEY: VARIANT
<222> LOCATION: (50)..(50)
<223> OTHER INFORMATION: Xaa is Ala or Thr
<220> FEATURE:
<221> NAME/KEY: VARIANT
<222> LOCATION: (69)..(69)
<223> OTHER INFORMATION: Xaa is Thr or Ser
<220> FEATURE:
<221> NAME/KEY: VARIANT
<222> LOCATION: (77)..(77)
<223> OTHER INFORMATION: Xaa is Ser or Asn
<220> FEATURE:
<221> NAME/KEY: VARIANT
<222> LOCATION: (95)..(95)
<223> OTHER INFORMATION: Xaa is Tyr or Phe

<400> SEQUENCE: 9

Gln Val Gln Leu Gln Gln Ser Gly Ala Glu Leu Ala Arg Pro Gly Ala
1               5                   10                  15

Ser Val Asn Leu Ser Cys Lys Ala Ser Gly Tyr Thr Leu Thr Arg Tyr
            20                  25                  30

Trp Met Gln Trp Val Lys Gln Arg Pro Gly Gln Gly Leu Glu Trp Ile

-continued

```
                35                  40                  45
Gly Xaa Ile Tyr Pro Gly Asp Gly Asp Thr Arg Tyr Ser Gln Lys Phe
 50                  55                  60
Lys Gly Lys Ala Xaa Leu Thr Ala Asp Lys Ser Ser Xaa Thr Ala Tyr
 65                  70                  75                  80
Met Gln Leu Asn Asn Leu Ala Ser Glu Asp Ser Ala Val Tyr Xaa Cys
                 85                  90                  95
Ala Phe Pro Asp Gly Tyr Tyr Ala Pro Tyr Gly Met Asp Tyr Trp
                100                 105                 110
Gly Gln Gly Thr Ser Val Thr Val Ser Ser
            115                 120

<210> SEQ ID NO 10
<211> LENGTH: 112
<212> TYPE: PRT
<213> ORGANISM: Mus musculus

<400> SEQUENCE: 10

Asp Ile Val Met Thr Gln Ser Pro Ser Ser Leu Asp Met Ser Glu Gly
 1               5                  10                  15
Gln Lys Val Thr Met Ile Cys Lys Ser Ser Gln Ser Leu Leu Asn Gly
                20                  25                  30
Ser Asn Gln Lys Asn Tyr Leu Ala Trp Tyr Gln Gln Lys Pro Gly Gln
             35                  40                  45
Ser Pro Lys Leu Leu Val Ser Phe Ala Ser Thr Arg Asp Ser Gly Val
 50                  55                  60
Pro Asp Arg Phe Ile Gly Ser Gly Ser Gly Thr Asp Phe Thr Leu Thr
 65                  70                  75                  80
Ile Thr Asn Val Gln Ala Glu Asp Leu Ala Asp Tyr Phe Cys Gln Gln
                 85                  90                  95
His Tyr Asp Thr Pro Tyr Thr Phe Gly Gly Gly Lys Leu Glu Ile Arg
                100                 105                 110

<210> SEQ ID NO 11
<211> LENGTH: 119
<212> TYPE: PRT
<213> ORGANISM: Mus musculus

<400> SEQUENCE: 11

Glu Val Gln Leu Val Glu Ser Gly Gly Asp Leu Val Lys Pro Gly Gly
 1               5                  10                  15
Ser Leu Lys Leu Ser Cys Ala Ala Ser Gly Phe Thr Phe Ser Thr Phe
                20                  25                  30
Ile Met Ser Trp Val Arg Gln Ser Pro Glu Lys Arg Leu Glu Trp Val
             35                  40                  45
Ala Thr Ile Asn Ser Gly Gly Tyr Tyr Thr Phe His Pro Asp Ser Val
 50                  55                  60
Lys Gly Arg Phe Thr Ile Ser Arg Asp Asn Ala Lys Asn Thr Leu Tyr
 65                  70                  75                  80
Leu Gln Met Ser Ser Leu Arg Ser Glu Asp Thr Ala Ile Tyr Tyr Cys
                 85                  90                  95
Ala Arg Gln Glu Gly Trp Ser Ser Ala Tyr Phe Ser Trp Gly Gln Gly
                100                 105                 110
Thr Leu Val Thr Val Ser Ala
            115

<210> SEQ ID NO 12
```

<211> LENGTH: 105
<212> TYPE: PRT
<213> ORGANISM: Mus musculus

<400> SEQUENCE: 12

Glu Asn Val Leu Thr Gln Ser Pro Ala Ile Met Ser Ala Ser Pro Gly
1               5                   10                  15

Glu Arg Val Thr Met Thr Cys Ser Ala Ser Ser Ser Val Ser Tyr Met
            20                  25                  30

His Trp Tyr Gln Gln Lys Ser Ser Asn Ser Pro Lys Leu Trp Ile Tyr
        35                  40                  45

Asp Thr Thr Lys Leu Ala Ser Gly Val Pro Gly Arg Phe Ser Gly Ser
    50                  55                  60

Gly Ser Gly Asn Ser Tyr Ser Leu Thr Ile Ser Ser Met Glu Ala Glu
65                  70                  75                  80

Asp Val Ala Thr Tyr Phe Cys Phe Gln Gly Ser Glu His Pro Leu Thr
                85                  90                  95

Phe Gly Gly Gly Thr Thr Leu Glu Ile
            100                 105

<210> SEQ ID NO 13
<211> LENGTH: 117
<212> TYPE: PRT
<213> ORGANISM: Mus musculus

<400> SEQUENCE: 13

Gln Val Gln Leu Gln Gln Ser Gly Pro Glu Leu Met Lys Pro Gly Ala
1               5                   10                  15

Ser Val Lys Ile Ser Cys Lys Ala Thr Gly Tyr Thr Phe Ser Thr Tyr
            20                  25                  30

Trp Ile Glu Trp Ile Lys Gln Arg Pro Gly His Gly Leu Glu Trp Ile
        35                  40                  45

Gly Glu Ile Leu Pro Gly Arg Gly Thr Thr Asn Tyr Asn Ala Lys Phe
    50                  55                  60

Gln Gly Lys Ala Thr Phe Thr Ala Glu Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Thr Thr Glu Ser Lys Leu Gly Asp Asp Asp Tyr Trp Gln Gly Thr Thr
            100                 105                 110

Leu Thr Val Ser Ser
        115

<210> SEQ ID NO 14
<211> LENGTH: 113
<212> TYPE: PRT
<213> ORGANISM: Mus musculus

<400> SEQUENCE: 14

Asp Ile Val Met Thr Gln Ser Pro Ser Ser Leu Ala Met Ser Val Gly
1               5                   10                  15

Gln Lys Val Thr Met Ile Cys Asn Ser Ser Gln Ser Leu Leu Asn Ser
            20                  25                  30

Ser Asn Gln Lys Asn Tyr Leu Ala Trp Tyr Gln Gln Lys Pro Gly Gln
        35                  40                  45

Ser Pro Arg Leu Leu Val Tyr Phe Ala Ser Thr Gly Glu Ser Gly Val
    50                  55                  60

Pro Asp Arg Phe Ile Gly Ser Gly Ser Gly Thr Asp Phe Thr Leu Thr

```
                65                  70                  75                  80
Ile Ser Asn Val Gln Ala Glu Asp Leu Ala Asp Tyr Phe Cys Gln Gln
                    85                  90                  95
His Phe Ser Thr Pro Tyr Thr Phe Gly Gly Gly Thr Lys Leu Glu Ile
                100                 105                 110
Arg

<210> SEQ ID NO 15
<211> LENGTH: 120
<212> TYPE: PRT
<213> ORGANISM: Mus musculus

<400> SEQUENCE: 15

Glu Val Gln Leu Val Glu Ser Gly Gly Asp Leu Val Lys Pro Gly Gly
1               5                   10                  15
Ser Leu Lys Leu Ser Cys Ala Ala Ser Gly Phe Thr Phe Ser Thr Tyr
                20                  25                  30
Ile Met Ser Trp Val Arg Gln Ser Pro Glu Lys Arg Leu Glu Trp Val
                35                  40                  45
Ala Thr Ile Asn Ser Gly Gly Tyr Tyr Thr Leu Tyr Pro Asp Ser Val
            50                  55                  60
Lys Gly Arg Phe Thr Ile Ser Arg Asp Asn Val Lys Asn Thr Leu Ser
65                  70                  75                  80
Leu Gln Leu Ser Ser Leu Arg Ser Glu Asp Thr Ala Met Tyr Phe Cys
                85                  90                  95
Ala Arg Gln Glu Gly Trp Ser Ser Ala Trp Phe Ala Tyr Trp Gly Gln
                100                 105                 110
Gly Thr Leu Val Thr Val Ser Ala
            115                 120

<210> SEQ ID NO 16
<211> LENGTH: 113
<212> TYPE: PRT
<213> ORGANISM: Mus musculus

<400> SEQUENCE: 16

Asp Ile Val Met Thr Gln Ser Pro Ser Ser Leu Ala Met Ser Val Gly
1               5                   10                  15
Gln Lys Val Thr Met Ile Cys Lys Ser Ser Gln Ser Leu Leu Asn Ser
                20                  25                  30
Ser Asn Gln Lys Asn Tyr Leu Ala Trp Tyr Gln Gln Lys Pro Gly His
            35                  40                  45
Ser Pro Lys Leu Leu Val Ser Phe Thr Ser Thr Arg Glu Ser Gly Val
        50                  55                  60
Pro Asp Arg Phe Ile Gly Ser Gly Ser Gly Thr Asp Phe Thr Leu Thr
65                  70                  75                  80
Ile Thr Asn Met Gln Ala Glu Asp Leu Ala Asp Tyr Phe Cys Gln Gln
                85                  90                  95
His Tyr Asp Thr Pro Tyr Thr Phe Gly Gly Gly Thr Lys Leu Glu Ile
                100                 105                 110
Arg

<210> SEQ ID NO 17
<211> LENGTH: 120
<212> TYPE: PRT
<213> ORGANISM: Mus musculus

<400> SEQUENCE: 17
```

```
Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Phe
            20                  25                  30

Val Met Ser Trp Val Arg Gln Ser Pro Glu Lys Arg Leu Glu Trp Val
        35                  40                  45

Ala Thr Ile Asn Ser Gly Gly Tyr Tyr Ser Phe His Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Ile Tyr Tyr Cys
                85                  90                  95

Ala Arg Gln Glu Gly Trp Ser Ser Ala Tyr Phe Ser Tyr Trp Gly Gln
                100                 105                 110

Gly Thr Leu Val Thr Val Ser Ala
            115                 120

<210> SEQ ID NO 18
<211> LENGTH: 113
<212> TYPE: PRT
<213> ORGANISM: Mus musculus

<400> SEQUENCE: 18

Asp Ile Val Met Thr Gln Ser Pro Ser Ser Leu Ala Met Ser Val Gly
1               5                   10                  15

Gln Lys Val Thr Met Ile Cys Asn Ser Ser Gln Ser Leu Leu Asn Ser
            20                  25                  30

Ser Asn Gln Lys Asn Tyr Leu Ala Trp Tyr Gln Gln Lys Pro Gly Gln
        35                  40                  45

Ser Pro Arg Leu Leu Ile Tyr Phe Ala Ser Thr Gly Glu Ser Gly Val
    50                  55                  60

Pro Asp Arg Phe Ile Gly Ser Gly Ser Gly Thr Asp Phe Thr Leu Thr
65                  70                  75                  80

Ile Ser Asn Val Gln Ala Glu Asp Leu Ala Asp Tyr Phe Cys Gln Gln
                85                  90                  95

His Phe Ser Thr Pro Tyr Thr Phe Gly Gly Gly Thr Lys Leu Glu Ile
                100                 105                 110

Arg

<210> SEQ ID NO 19
<211> LENGTH: 120
<212> TYPE: PRT
<213> ORGANISM: Mus musculus

<400> SEQUENCE: 19

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Thr Tyr
            20                  25                  30

Ile Met Ser Trp Val Arg Gln Ser Pro Glu Lys Arg Leu Glu Trp Val
        35                  40                  45

Ala Thr Ile Asn Ser Gly Gly Tyr Tyr Thr Leu Tyr Pro Asp Ser Val
    50                  55                  60

Lys Gly Arg Phe Thr Ile Ser Arg Asp Asn Ala Lys Asn Thr Leu Ser
65                  70                  75                  80

Leu Gln Leu Ser Ser Leu Arg Ser Glu Asp Thr Ala Met Tyr Phe Cys
```

```
                    85                  90                  95
Ala Arg Gln Glu Gly Trp Ser Ser Ala Trp Phe Ala Tyr Trp Gly Gln
                100                 105                 110
Gly Thr Leu Val Thr Val Ser Ala
        115                 120

<210> SEQ ID NO 20
<211> LENGTH: 113
<212> TYPE: PRT
<213> ORGANISM: Mus musculus

<400> SEQUENCE: 20

Asp Ile Val Met Thr Gln Ser Pro Ser Ser Leu Ala Met Ser Val Gly
1               5                   10                  15

Gln Lys Val Thr Met Ile Cys Asn Ser Ser Gln Ser Leu Leu Asn Ser
            20                  25                  30

Ser Asn Gln Lys Asn Tyr Leu Ala Trp Tyr Gln Gln Lys Pro Gly Gln
        35                  40                  45

Ser Pro Arg Leu Leu Val Tyr Phe Ala Ser Thr Gly Glu Ser Gly Val
    50                  55                  60

Pro Asp Arg Phe Ile Gly Ser Gly Ser Gly Thr Asp Phe Thr Leu Thr
65                  70                  75                  80

Ile Ser Asn Val Gln Ala Glu Asp Leu Ala Asp Tyr Phe Cys Gln Gln
                85                  90                  95

His Phe Ser Thr Pro Tyr Thr Phe Gly Gly Gly Thr Lys Leu Glu Ile
                100                 105                 110

Arg

<210> SEQ ID NO 21
<211> LENGTH: 120
<212> TYPE: PRT
<213> ORGANISM: Mus musculus

<400> SEQUENCE: 21

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Thr Tyr
            20                  25                  30

Ile Met Ser Trp Val Arg Gln Ser Pro Glu Lys Arg Leu Glu Trp Val
        35                  40                  45

Ala Thr Ile Asn Ser Gly Gly Tyr Tyr Thr Leu Tyr Pro Asp Ser Val
    50                  55                  60

Lys Gly Arg Phe Thr Ile Ser Arg Asp Asn Ala Lys Asn Thr Leu Ser
65                  70                  75                  80

Leu Gln Leu Ser Ser Leu Arg Ser Glu Asp Thr Ala Met Tyr Phe Cys
                85                  90                  95

Ala Arg Gln Glu Gly Trp Ser Ser Ala Trp Phe Ala Tyr Trp Gly Gln
                100                 105                 110

Gly Thr Leu Val Thr Val Ser Ala
        115                 120

<210> SEQ ID NO 22
<211> LENGTH: 113
<212> TYPE: PRT
<213> ORGANISM: Mus musculus

<400> SEQUENCE: 22

Asp Ile Val Met Thr Gln Ser Pro Ser Ser Leu Ala Met Ser Val Gly
```

```
                  1               5                  10                 15
         Gln Lys Val Thr Met Ile Cys Asn Ser Ser Gln Ser Leu Leu Asn Ser
                          20                  25                  30

Ser Asn Gln Lys Asn Tyr Leu Ala Trp Tyr Gln Gln Lys Pro Gly Gln
                          35                  40                  45

Ser Pro Arg Leu Leu Val Tyr Phe Ala Ser Thr Gly Glu Ser Gly Val
                  50                  55                  60

Pro Asp Arg Phe Ile Gly Ser Gly Ser Gly Thr Asp Phe Thr Leu Thr
         65                  70                  75                  80

Ile Ser Asn Val Gln Ala Glu Asp Leu Ala Asp Tyr Phe Cys Gln Gln
                              85                  90                  95

His Phe Ser Thr Pro Tyr Thr Phe Gly Gly Gly Thr Lys Leu Glu Ile
                         100                 105                 110

Arg

<210> SEQ ID NO 23
<211> LENGTH: 120
<212> TYPE: PRT
<213> ORGANISM: Mus musculus

<400> SEQUENCE: 23

Glu Val Gln Leu Val Glu Ser Gly Gly Asp Leu Val Lys Pro Gly Gly
         1               5                  10                  15

Ser Leu Lys Leu Ser Cys Ala Ala Ser Gly Phe Thr Phe Ser Thr Tyr
                          20                  25                  30

Ile Met Ser Trp Val Arg Gln Ser Pro Glu Lys Arg Leu Glu Trp Val
                          35                  40                  45

Ala Thr Ile Asn Ser Gly Gly Tyr Tyr Thr Leu Tyr Pro Asp Ser Val
                      50                  55                  60

Lys Gly Arg Phe Thr Ile Ser Arg Asp Asn Ala Lys Asn Thr Leu Ser
         65                  70                  75                  80

Leu Gln Leu Ser Ser Leu Arg Ser Glu Asp Thr Ala Met Tyr Phe Cys
                          85                  90                  95

Ala Arg Gln Glu Gly Trp Ser Ser Ala Trp Phe Ala Tyr Trp Gly Gln
                         100                 105                 110

Gly Thr Leu Val Thr Val Ser Ala
                         115                 120

<210> SEQ ID NO 24
<211> LENGTH: 113
<212> TYPE: PRT
<213> ORGANISM: Mus musculus

<400> SEQUENCE: 24

Asp Ile Val Met Thr Gln Ser Pro Ser Ser Leu Ala Met Ser Val Gly
         1               5                  10                  15

Gln Lys Val Thr Met Ile Cys Asn Ser Ser Gln Ser Leu Leu Asn Ser
                          20                  25                  30

Ser Asn Gln Lys Asn Tyr Leu Ala Trp Tyr Gln Gln Arg Pro Gly Gln
                          35                  40                  45

Ser Pro Arg Leu Leu Val Tyr Phe Ala Ser Thr Gly Glu Ser Gly Val
                      50                  55                  60

Pro Asp Arg Phe Met Gly Ser Gly Ser Gly Thr Asp Phe Thr Leu Thr
         65                  70                  75                  80

Ile Ser Asn Val Gln Ala Glu Asp Leu Ala Asp Tyr Phe Cys Gln Gln
                          85                  90                  95
```

```
His Phe Ser Thr Pro Tyr Thr Phe Gly Gly Gly Thr Lys Leu Glu Ile
            100                 105                 110
Arg
```

<210> SEQ ID NO 25
<211> LENGTH: 120
<212> TYPE: PRT
<213> ORGANISM: Mus musculus

<400> SEQUENCE: 25

```
Glu Val Gln Leu Val Glu Ser Gly Gly Leu Val Lys Pro Gly Gly
1               5                   10                  15

Ser Leu Lys Leu Ser Cys Ala Val Ser Gly Phe Thr Phe Lys Thr Tyr
                20                  25                  30

Ile Met Ser Trp Val Arg Gln Ser Pro Glu Lys Arg Leu Glu Trp Val
            35                  40                  45

Ala Thr Ile Asn Ser Gly Gly Tyr Tyr Thr Ile Tyr Pro Asp Ser Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Gln Glu Gly Trp Ser Ser Ala Trp Phe Ala Tyr Trp Gly Gln
            100                 105                 110

Gly Thr Leu Val Thr Val Ser Ala
        115                 120
```

<210> SEQ ID NO 26
<211> LENGTH: 107
<212> TYPE: PRT
<213> ORGANISM: Mus musculus

<400> SEQUENCE: 26

```
Asp Ile Gln Met Ser Gln Ser Pro Ala Ser Leu Ser Ala Ser Val Gly
1               5                   10                  15

Glu Thr Val Thr Ile Thr Cys Arg Ala Ser Gly Ser Ile His Asn Tyr
                20                  25                  30

Leu Ala Trp Tyr Gln Gln Lys Gln Gly Lys Ser Pro Gln Leu Leu Val
            35                  40                  45

Tyr Asn Ala Glu Thr Leu Ala Asp Gly Val Pro Ser Arg Phe Ser Gly
        50                  55                  60

Ser Gly Ser Gly Thr Gln Tyr Ser Leu Lys Ile Ser Ser Leu Gln Pro
65                  70                  75                  80

Glu Asp Phe Gly Thr Tyr Tyr Cys Gln His Phe Trp Ile Thr Pro Trp
                85                  90                  95

Thr Phe Gly Gly Gly Thr Lys Leu Glu Ile Lys
            100                 105
```

<210> SEQ ID NO 27
<211> LENGTH: 122
<212> TYPE: PRT
<213> ORGANISM: Mus musculus

<400> SEQUENCE: 27

```
Gln Val Gln Val Gln Gln Ser Gly Ala Glu Leu Ala Arg Pro Gly Ala
1               5                   10                  15

Ser Val Lys Leu Ser Cys Lys Ala Ser Gly Tyr Thr Leu Thr Arg Tyr
                20                  25                  30
```

Trp Met Gln Trp Val Lys Gln Arg Pro Gly Gln Gly Leu Glu Trp Ile
            35                  40                  45

Gly Ala Ile Tyr Pro Arg Asp Gly Asp Thr Arg Tyr Ser Gln Lys Phe
        50                  55                  60

Lys Gly Lys Ala Thr Leu Thr Ala Asp Lys Ser Ser Thr Thr Ala Tyr
65                  70                  75                  80

Met Gln Leu Ser Ser Leu Ala Ser Glu Asp Ser Ala Val Tyr Tyr Cys
                85                  90                  95

Ala Tyr Pro Asp Gly Ser Tyr Ala Ala Pro Asn Gly Met Glu Tyr Trp
            100                 105                 110

Gly Gln Gly Ser Ser Val Thr Val Ser Ser
            115                 120

<210> SEQ ID NO 28
<211> LENGTH: 33
<212> TYPE: DNA
<213> ORGANISM: Mus musculus

<400> SEQUENCE: 28
cgactgagcc acctccagat gttaactgct cac                                    33

<210> SEQ ID NO 29
<211> LENGTH: 28
<212> TYPE: DNA
<213> ORGANISM: Mus musculus

<400> SEQUENCE: 29 cagggccag tggatagaca gatggggg                                           28

<210> SEQ ID NO 30
<211> LENGTH: 27
<212> TYPE: DNA
<213> ORGANISM: Mus musculus

<400> SEQUENCE: 30 cagggccag tggatagacc gatgggg                                            27

<210> SEQ ID NO 31
<211> LENGTH: 127
<212> TYPE: PRT
<213> ORGANISM: Mus musculus
<220> FEATURE:
<221> NAME/KEY: SIGNAL
<222> LOCATION: (1)..(20)
<220> FEATURE:
<221> NAME/KEY: VARIANT
<222> LOCATION: (62)..(62)
<223> OTHER INFORMATION: Xaa is Lys or Arg

<400> SEQUENCE: 31

Met Ser Val Leu Thr Gln Val Leu Ala Leu Leu Leu Leu Trp Leu Thr
1               5                   10                  15

Gly Ala Arg Cys Asp Ile Gln Met Thr Gln Ser Pro Ala Ser Leu Ser
            20                  25                  30

Ala Ser Val Gly Glu Thr Val Thr Ile Thr Cys Arg Ala Ser Gly Asn
        35                  40                  45

Ile His Asn Tyr Leu Ala Trp Tyr Gln Gln Lys Gln Gly Xaa Ser Pro
    50                  55                  60

Gln Leu Leu Val Tyr Asn Ala Lys Thr Leu Ala Asp Gly Val Pro Ser
65                  70                  75                  80

Arg Phe Ser Gly Ser Arg Ser Glu Thr Gln Tyr Ser Leu Lys Ile Asn
                85                  90                  95

```
Ser Leu Gln Pro Glu Asp Phe Gly Ser Tyr Tyr Cys Gln His Phe Trp
                100                 105                 110

Ser Thr Pro Trp Thr Phe Gly Gly Gly Thr Lys Leu Glu Ile Lys
                115                 120                 125

<210> SEQ ID NO 32
<211> LENGTH: 141
<212> TYPE: PRT
<213> ORGANISM: Mus musculus
<220> FEATURE:
<221> NAME/KEY: SIGNAL
<222> LOCATION: (1)..(19)
<220> FEATURE:
<221> NAME/KEY: VARIANT
<222> LOCATION: (69)..(69)
<223> OTHER INFORMATION: Xaa is Ala or Thr
<220> FEATURE:
<221> NAME/KEY: VARIANT
<222> LOCATION: (88)..(88)
<223> OTHER INFORMATION: Xaa is Thr or Ser
<220> FEATURE:
<221> NAME/KEY: VARIANT
<222> LOCATION: (96)..(96)
<223> OTHER INFORMATION: Xaa is Ser or Asn
<220> FEATURE:
<221> NAME/KEY: VARIANT
<222> LOCATION: (114)..(114)
<223> OTHER INFORMATION: Xaa is Tyr or Phe

<400> SEQUENCE: 32

Met Glu Cys Asn Trp Ile Leu Pro Phe Ile Leu Ser Val Thr Ser Gly
1               5                   10                  15

Val Tyr Ser Gln Val Gln Leu Gln Gln Ser Gly Ala Glu Leu Ala Arg
                20                  25                  30

Pro Gly Ala Ser Val Asn Leu Ser Cys Lys Ala Ser Gly Tyr Thr Leu
            35                  40                  45

Thr Arg Tyr Trp Met Gln Trp Val Lys Gln Arg Pro Gly Gln Gly Leu
        50                  55                  60

Glu Trp Ile Gly Xaa Ile Tyr Pro Gly Asp Gly Asp Thr Arg Tyr Ser
65                  70                  75                  80

Gln Lys Phe Lys Gly Lys Ala Xaa Leu Thr Ala Asp Lys Ser Ser Xaa
                85                  90                  95

Thr Ala Tyr Met Gln Leu Asn Asn Leu Ala Ser Glu Asp Ser Ala Val
                100                 105                 110

Tyr Xaa Cys Ala Phe Pro Asp Gly Tyr Tyr Ala Ala Pro Tyr Gly Met
            115                 120                 125

Asp Tyr Trp Gly Gln Gly Thr Ser Val Thr Val Ser Ser
        130                 135                 140

<210> SEQ ID NO 33
<211> LENGTH: 132
<212> TYPE: PRT
<213> ORGANISM: Mus musculus
<220> FEATURE:
<221> NAME/KEY: SIGNAL
<222> LOCATION: (1)..(20)

<400> SEQUENCE: 33

Met Glu Ser Gln Thr Gln Val Leu Met Phe Leu Leu Leu Trp Val Ser
1               5                   10                  15

Gly Ala Cys Ala Asp Ile Val Met Thr Gln Ser Pro Ser Ser Leu Asp
                20                  25                  30

Met Ser Glu Gly Gln Lys Val Thr Met Ile Cys Lys Ser Ser Gln Ser
            35                  40                  45
```

```
Leu Leu Asn Gly Ser Asn Gln Lys Asn Tyr Leu Ala Trp Tyr Gln Gln
         50                  55                  60

Lys Pro Gly Gln Ser Pro Lys Leu Leu Val Ser Phe Ala Ser Thr Arg
 65                  70                  75                  80

Asp Ser Gly Val Pro Asp Arg Phe Ile Gly Ser Gly Ser Gly Thr Asp
                 85                  90                  95

Phe Thr Leu Thr Ile Thr Asn Val Gln Ala Glu Asp Leu Ala Asp Tyr
            100                 105                 110

Phe Cys Gln Gln His Tyr Asp Thr Pro Tyr Thr Phe Gly Gly Gly Lys
            115                 120                 125

Leu Glu Ile Arg
    130
```

```
<210> SEQ ID NO 34
<211> LENGTH: 138
<212> TYPE: PRT
<213> ORGANISM: Mus musculus
<220> FEATURE:
<221> NAME/KEY: SIGNAL
<222> LOCATION: (1)..(19)

<400> SEQUENCE: 34

Met Asn Phe Val Arg Ser Leu Ile Phe Leu Ala Leu Ile Leu Lys Gly
 1               5                  10                  15

Val Gln Cys Glu Val Gln Leu Val Glu Ser Gly Gly Asp Leu Val Lys
            20                  25                  30

Pro Gly Gly Ser Leu Lys Leu Ser Cys Ala Ala Ser Gly Phe Thr Phe
        35                  40                  45

Ser Thr Phe Ile Met Ser Trp Val Arg Gln Ser Pro Glu Lys Arg Leu
 50                  55                  60

Glu Trp Val Ala Thr Ile Asn Ser Gly Gly Tyr Tyr Thr Phe His Pro
 65                  70                  75                  80

Asp Ser Val Lys Gly Arg Phe Thr Ile Ser Arg Asp Asn Ala Lys Asn
                 85                  90                  95

Thr Leu Tyr Leu Gln Met Ser Ser Leu Arg Ser Glu Asp Thr Ala Ile
            100                 105                 110

Tyr Tyr Cys Ala Arg Gln Glu Gly Trp Ser Ser Ala Tyr Phe Ser Trp
            115                 120                 125

Gly Gln Gly Thr Leu Val Thr Val Ser Ala
        130                 135
```

```
<210> SEQ ID NO 35
<211> LENGTH: 127
<212> TYPE: PRT
<213> ORGANISM: Mus musculus
<220> FEATURE:
<221> NAME/KEY: SIGNAL
<222> LOCATION: (1)..(21)

<400> SEQUENCE: 35

Met Asp Phe Gln Val Gln Ile Phe Ser Phe Leu Leu Ile Ser Ala Ser
 1               5                  10                  15

Val Ile Met Ser Arg Gly Glu Asn Val Leu Thr Gln Ser Pro Ala Ile
            20                  25                  30

Met Ser Ala Ser Pro Gly Glu Arg Val Thr Met Thr Cys Ser Ala Ser
        35                  40                  45

Ser Ser Val Ser Tyr Met His Trp Tyr Gln Gln Lys Ser Ser Asn Ser
 50                  55                  60
```

```
Pro Lys Leu Trp Ile Tyr Asp Thr Thr Lys Leu Ala Ser Gly Val Pro
 65                  70                  75                  80

Gly Arg Phe Ser Gly Ser Gly Ser Gly Asn Ser Tyr Ser Leu Thr Ile
             85                  90                  95

Ser Ser Met Glu Ala Glu Asp Val Ala Thr Tyr Phe Cys Phe Gln Gly
            100                 105                 110

Ser Glu His Pro Leu Thr Phe Gly Gly Gly Thr Leu Glu Ile
        115                 120                 125
```

<210> SEQ ID NO 36
<211> LENGTH: 136
<212> TYPE: PRT
<213> ORGANISM: Mus musculus
<220> FEATURE:
<221> NAME/KEY: SIGNAL
<222> LOCATION: (1)..(19)

<400> SEQUENCE: 36

```
Met Glu Trp Thr Trp Val Phe Leu Phe Leu Leu Ser Val Thr Ala Gly
 1               5                  10                  15

Val His Ser Gln Val Gln Leu Gln Gln Ser Gly Pro Glu Leu Met Lys
             20                  25                  30

Pro Gly Ala Ser Val Lys Ile Ser Cys Lys Ala Thr Gly Tyr Thr Phe
             35                  40                  45

Ser Thr Tyr Trp Ile Glu Trp Ile Lys Gln Arg Pro Gly His Gly Leu
         50                  55                  60

Glu Trp Ile Gly Glu Ile Leu Pro Gly Arg Gly Thr Thr Asn Tyr Asn
 65                  70                  75                  80

Ala Lys Phe Gln Gly Lys Ala Thr Phe Thr Ala Glu Thr Ser Ser Asn
             85                  90                  95

Thr Ala Tyr Met Gln Leu Ser Ser Leu Thr Ser Glu Asp Ser Ala Val
            100                 105                 110

Tyr Tyr Cys Thr Thr Gly Ser Lys Leu Gly Asp Asp Ala Tyr Trp Gln
        115                 120                 125

Gly Thr Thr Leu Thr Val Ser Ser
        130                 135
```

<210> SEQ ID NO 37
<211> LENGTH: 133
<212> TYPE: PRT
<213> ORGANISM: Mus musculus
<220> FEATURE:
<221> NAME/KEY: SIGNAL
<222> LOCATION: (1)..(20)

<400> SEQUENCE: 37

```
Met Glu Ser Gln Thr Gln Val Leu Met Phe Leu Leu Leu Trp Val Ser
 1               5                  10                  15

Gly Ala Cys Ala Asp Ile Val Met Thr Gln Ser Pro Ser Ser Leu Ala
             20                  25                  30

Met Ser Val Gly Gln Lys Val Thr Met Ile Cys Asn Ser Ser Gln Ser
             35                  40                  45

Leu Leu Asn Ser Ser Asn Gln Lys Asn Tyr Leu Ala Trp Tyr Gln Gln
         50                  55                  60

Lys Pro Gly Gln Ser Pro Arg Leu Leu Val Tyr Phe Ala Ser Thr Gly
 65                  70                  75                  80

Glu Ser Gly Val Pro Asp Arg Phe Ile Gly Ser Gly Ser Gly Thr Asp
             85                  90                  95

Phe Thr Leu Thr Ile Ser Asn Val Gln Ala Glu Asp Leu Ala Asp Tyr
```

100                 105                 110
Phe Cys Gln Gln His Phe Ser Thr Pro Tyr Thr Phe Gly Gly Gly Thr
            115                 120                 125

Lys Leu Glu Ile Arg
        130

<210> SEQ ID NO 38
<211> LENGTH: 139
<212> TYPE: PRT
<213> ORGANISM: Mus musculus
<220> FEATURE:
<221> NAME/KEY: SIGNAL
<222> LOCATION: (1)..(19)

<400> SEQUENCE: 38

Met Asn Phe Val Leu Ser Leu Ile Phe Leu Ala Leu Ile Leu Lys Gly
1               5                   10                  15

Val Gln Cys Glu Val Gln Leu Val Glu Ser Gly Gly Asp Leu Val Lys
            20                  25                  30

Pro Gly Gly Ser Leu Lys Leu Ser Cys Ala Ala Ser Gly Phe Thr Phe
        35                  40                  45

Ser Thr Tyr Ile Met Ser Trp Val Arg Gln Ser Pro Glu Lys Arg Leu
    50                  55                  60

Glu Trp Val Ala Thr Ile Asn Ser Gly Gly Tyr Tyr Thr Leu Tyr Pro
65                  70                  75                  80

Asp Ser Val Lys Gly Arg Phe Thr Ile Ser Arg Asp Asn Val Lys Asn
                85                  90                  95

Thr Leu Ser Leu Gln Leu Ser Ser Leu Arg Ser Glu Asp Thr Ala Met
            100                 105                 110

Tyr Phe Cys Ala Arg Gln Glu Gly Trp Ser Ser Ala Trp Phe Ala Tyr
        115                 120                 125

Trp Gly Gln Gly Thr Leu Val Thr Val Ser Ala
    130                 135

<210> SEQ ID NO 39
<211> LENGTH: 133
<212> TYPE: PRT
<213> ORGANISM: Mus musculus
<220> FEATURE:
<221> NAME/KEY: SIGNAL
<222> LOCATION: (1)..(20)

<400> SEQUENCE: 39

Met Glu Ser Gln Thr Gln Val Leu Met Phe Leu Leu Leu Trp Val Ser
1               5                   10                  15

Gly Ala Cys Ala Asp Ile Val Met Thr Gln Ser Pro Ser Ser Leu Ala
            20                  25                  30

Met Ser Val Gly Gln Lys Val Thr Met Ile Cys Lys Ser Ser Gln Ser
        35                  40                  45

Leu Leu Asn Ser Ser Asn Gln Lys Asn Tyr Leu Ala Trp Tyr Gln Gln
    50                  55                  60

Lys Pro Gly His Ser Pro Lys Leu Leu Val Ser Phe Thr Ser Thr Arg
65                  70                  75                  80

Glu Ser Gly Val Pro Asp Arg Phe Ile Gly Ser Gly Ser Gly Thr Asp
                85                  90                  95

Phe Thr Leu Thr Ile Thr Asn Met Gln Ala Glu Asp Leu Ala Asp Tyr
            100                 105                 110

Phe Cys Gln Gln His Tyr Asp Thr Pro Tyr Thr Phe Gly Gly Gly Thr
        115                 120                 125

```
Lys Leu Glu Ile Arg
    130

<210> SEQ ID NO 40
<211> LENGTH: 139
<212> TYPE: PRT
<213> ORGANISM: Mus musculus
<220> FEATURE:
<221> NAME/KEY: SIGNAL
<222> LOCATION: (1)..(19)

<400> SEQUENCE: 40

Met Asn Phe Val Leu Ser Leu Ile Phe Leu Ala Leu Ile Leu Lys Gly
1               5                   10                  15

Val Gln Cys Glu Val Gln Leu Val Glu Ser Gly Gly Asp Leu Val Lys
            20                  25                  30

Pro Gly Gly Ser Leu Lys Leu Ser Cys Ala Ala Ser Gly Phe Thr Phe
        35                  40                  45

Ser Ser Phe Val Met Ser Trp Val Arg Gln Ser Pro Glu Lys Arg Leu
    50                  55                  60

Glu Trp Val Ala Thr Ile Asn Ser Gly Gly Tyr Tyr Ser Phe His Pro
65                  70                  75                  80

Asp Ser Val Lys Gly Arg Phe Thr Ile Ser Arg Asp Asn Ala Lys Asn
                85                  90                  95

Thr Leu Tyr Leu Gln Met Ser Ser Leu Arg Ser Glu Asp Thr Ala Ile
            100                 105                 110

Tyr Tyr Cys Ala Arg Gln Glu Gly Trp Ser Ser Ala Tyr Phe Ser Tyr
        115                 120                 125

Trp Gly Gln Gly Thr Leu Val Thr Val Ser Ala
    130                 135

<210> SEQ ID NO 41
<211> LENGTH: 133
<212> TYPE: PRT
<213> ORGANISM: Mus musculus
<220> FEATURE:
<221> NAME/KEY: SIGNAL
<222> LOCATION: (1)..(20)

<400> SEQUENCE: 41

Met Glu Ser Gln Thr Gln Val Leu Met Phe Leu Leu Leu Trp Val Ser
1               5                   10                  15

Gly Ala Cys Ala Asp Ile Val Met Thr Gln Ser Pro Ser Ser Leu Ala
            20                  25                  30

Met Ser Val Gly Gln Lys Val Thr Met Ile Cys Asn Ser Ser Gln Ser
        35                  40                  45

Leu Leu Asn Ser Ser Asn Gln Lys Asn Tyr Leu Ala Trp Tyr Gln Gln
    50                  55                  60

Lys Pro Gly Gln Ser Pro Arg Leu Leu Ile Tyr Phe Ala Ser Thr Gly
65                  70                  75                  80

Glu Ser Gly Val Pro Asp Arg Phe Ile Gly Ser Gly Ser Gly Thr Asp
                85                  90                  95

Phe Thr Leu Thr Ile Ser Asn Val Gln Ala Glu Asp Leu Ala Asp Tyr
            100                 105                 110

Phe Cys Gln Gln His Phe Ser Thr Pro Tyr Thr Phe Gly Gly Gly Thr
        115                 120                 125

Lys Leu Glu Ile Arg
    130
```

```
<210> SEQ ID NO 42
<211> LENGTH: 139
<212> TYPE: PRT
<213> ORGANISM: Mus musculus
<220> FEATURE:
<221> NAME/KEY: SIGNAL
<222> LOCATION: (1)..(19)

<400> SEQUENCE: 42

Met Asn Phe Val Leu Ser Leu Ile Phe Leu Ala Leu Ile Leu Lys Gly
1               5                   10                  15

Val Gln Cys Glu Val Gln Leu Val Glu Ser Gly Gly Asp Leu Val Lys
            20                  25                  30

Pro Gly Gly Ser Leu Lys Leu Ser Cys Ala Ala Ser Gly Phe Thr Phe
        35                  40                  45

Ser Thr Tyr Ile Met Ser Trp Val Arg Gln Ser Pro Glu Lys Arg Leu
    50                  55                  60

Glu Trp Val Ala Thr Ile Asn Ser Gly Gly Tyr Tyr Thr Leu Tyr Pro
65                  70                  75                  80

Asp Ser Val Lys Gly Arg Phe Thr Ile Ser Arg Asp Asn Ala Lys Asn
                85                  90                  95

Thr Leu Ser Leu Gln Leu Ser Ser Leu Arg Ser Glu Asp Thr Ala Met
            100                 105                 110

Tyr Phe Cys Ala Arg Gln Glu Gly Trp Ser Ser Ala Trp Phe Ala Tyr
        115                 120                 125

Trp Gly Gln Gly Thr Leu Val Thr Val Ser Ala
    130                 135

<210> SEQ ID NO 43
<211> LENGTH: 133
<212> TYPE: PRT
<213> ORGANISM: Mus musculus
<220> FEATURE:
<221> NAME/KEY: SIGNAL
<222> LOCATION: (1)..(20)

<400> SEQUENCE: 43

Met Glu Ser Gln Thr Gln Val Leu Met Phe Leu Leu Leu Trp Val Ser
1               5                   10                  15

Gly Ala Cys Ala Asp Ile Val Met Thr Gln Ser Pro Ser Ser Leu Ala
            20                  25                  30

Met Ser Val Gly Gln Lys Val Thr Met Ile Cys Asn Ser Ser Gln Ser
        35                  40                  45

Leu Leu Asn Ser Ser Asn Gln Lys Asn Tyr Leu Ala Trp Tyr Gln Gln
    50                  55                  60

Lys Pro Gly Gln Ser Pro Arg Leu Leu Val Tyr Phe Ala Ser Thr Gly
65                  70                  75                  80

Glu Ser Gly Val Pro Asp Arg Phe Ile Gly Ser Gly Ser Gly Thr Asp
                85                  90                  95

Phe Thr Leu Thr Ile Ser Asn Val Gln Ala Glu Asp Leu Ala Asp Tyr
            100                 105                 110

Phe Cys Gln Gln His Phe Ser Thr Pro Tyr Thr Phe Gly Gly Gly Thr
        115                 120                 125

Lys Leu Glu Ile Arg
    130

<210> SEQ ID NO 44
<211> LENGTH: 139
<212> TYPE: PRT
```

<213> ORGANISM: Mus musculus
<220> FEATURE:
<221> NAME/KEY: SIGNAL
<222> LOCATION: (1)..(19)

<400> SEQUENCE: 44

Met Asn Phe Val Leu Ser Leu Ile Phe Leu Ala Leu Ile Leu Lys Gly
1               5                   10                  15

Val Gln Cys Glu Val Gln Leu Val Glu Ser Gly Gly Asp Leu Val Lys
            20                  25                  30

Pro Gly Gly Ser Leu Lys Leu Ser Cys Ala Ala Ser Gly Phe Thr Phe
        35                  40                  45

Ser Thr Tyr Ile Met Ser Trp Val Arg Gln Ser Pro Glu Lys Arg Leu
    50                  55                  60

Glu Trp Val Ala Thr Ile Asn Ser Gly Gly Tyr Tyr Thr Leu Tyr Pro
65                  70                  75                  80

Asp Ser Val Lys Gly Arg Phe Thr Ile Ser Arg Asp Asn Ala Lys Asn
                85                  90                  95

Thr Leu Ser Leu Gln Leu Ser Ser Leu Arg Ser Glu Asp Thr Ala Met
            100                 105                 110

Tyr Phe Cys Ala Arg Gln Glu Gly Trp Ser Ser Ala Trp Phe Ala Tyr
        115                 120                 125

Trp Gly Gln Gly Thr Leu Val Thr Val Ser Ala
    130                 135

<210> SEQ ID NO 45
<211> LENGTH: 133
<212> TYPE: PRT
<213> ORGANISM: Mus musculus
<220> FEATURE:
<221> NAME/KEY: SIGNAL
<222> LOCATION: (1)..(20)

<400> SEQUENCE: 45

Met Glu Ser Gln Thr Gln Val Leu Met Phe Leu Leu Leu Trp Val Ser
1               5                   10                  15

Gly Ala Cys Ala Asp Ile Val Met Thr Gln Ser Pro Ser Ser Leu Ala
            20                  25                  30

Met Ser Val Gly Gln Lys Val Thr Met Ile Cys Asn Ser Ser Gln Ser
        35                  40                  45

Leu Leu Asn Ser Ser Asn Gln Lys Asn Tyr Leu Ala Trp Tyr Gln Gln
    50                  55                  60

Lys Pro Gly Gln Ser Pro Arg Leu Leu Val Tyr Phe Ala Ser Thr Gly
65                  70                  75                  80

Glu Ser Gly Val Pro Asp Arg Phe Ile Gly Ser Gly Ser Gly Thr Asp
                85                  90                  95

Phe Thr Leu Thr Ile Ser Asn Val Gln Ala Glu Asp Leu Ala Asp Tyr
            100                 105                 110

Phe Cys Gln Gln His Phe Ser Thr Pro Tyr Thr Phe Gly Gly Gly Thr
        115                 120                 125

Lys Leu Glu Ile Arg
    130

<210> SEQ ID NO 46
<211> LENGTH: 139
<212> TYPE: PRT
<213> ORGANISM: Mus musculus
<220> FEATURE:
<221> NAME/KEY: SIGNAL
<222> LOCATION: (1)..(19)

<400> SEQUENCE: 46

Met Asn Phe Val Leu Ser Leu Ile Phe Leu Ala Leu Ile Leu Lys Gly
1               5                   10                  15

Val Gln Cys Glu Val Gln Leu Val Glu Ser Gly Gly Asp Leu Val Lys
            20                  25                  30

Pro Gly Gly Ser Leu Lys Leu Ser Cys Ala Ala Ser Gly Phe Thr Phe
        35                  40                  45

Ser Thr Tyr Ile Met Ser Trp Val Arg Gln Ser Pro Glu Lys Arg Leu
    50                  55                  60

Glu Trp Val Ala Thr Ile Asn Ser Gly Gly Tyr Tyr Thr Leu Tyr Pro
65                  70                  75                  80

Asp Ser Val Lys Gly Arg Phe Thr Ile Ser Arg Asp Asn Ala Lys Asn
                85                  90                  95

Thr Leu Ser Leu Gln Leu Ser Ser Leu Arg Ser Glu Asp Thr Ala Met
            100                 105                 110

Tyr Phe Cys Ala Arg Gln Glu Gly Trp Ser Ser Ala Trp Phe Ala Tyr
        115                 120                 125

Trp Gly Gln Gly Thr Leu Val Thr Val Ser Ala
    130                 135

<210> SEQ ID NO 47
<211> LENGTH: 133
<212> TYPE: PRT
<213> ORGANISM: Mus musculus
<220> FEATURE:
<221> NAME/KEY: SIGNAL
<222> LOCATION: (1)..(20)

<400> SEQUENCE: 47

Met Glu Ser Gln Thr Gln Val Leu Met Phe Leu Leu Leu Trp Val Ser
1               5                   10                  15

Gly Ala Cys Ala Asp Ile Val Met Thr Gln Ser Pro Ser Ser Leu Ala
            20                  25                  30

Met Ser Val Gly Gln Lys Val Thr Met Ile Cys Asn Ser Ser Gln Ser
        35                  40                  45

Leu Leu Asn Ser Ser Asn Gln Lys Asn Tyr Leu Ala Trp Tyr Gln Gln
    50                  55                  60

Arg Pro Gly Gln Ser Pro Arg Leu Leu Val Tyr Phe Ala Ser Thr Gly
65                  70                  75                  80

Glu Ser Gly Val Pro Asp Arg Phe Met Gly Ser Gly Ser Gly Thr Asp
                85                  90                  95

Phe Thr Leu Thr Ile Ser Asn Val Gln Ala Glu Asp Leu Ala Asp Tyr
            100                 105                 110

Phe Cys Gln Gln His Phe Ser Thr Pro Tyr Thr Phe Gly Gly Gly Thr
        115                 120                 125

Lys Leu Glu Ile Arg
    130

<210> SEQ ID NO 48
<211> LENGTH: 139
<212> TYPE: PRT
<213> ORGANISM: Mus musculus
<220> FEATURE:
<221> NAME/KEY: SIGNAL
<222> LOCATION: (1)..(19)

<400> SEQUENCE: 48

Met Asn Phe Val Leu Ser Leu Ile Phe Leu Ala Leu Ile Leu Lys Gly

-continued

```
                1               5                  10                 15
Val Gln Cys Glu Val Gln Leu Val Glu Ser Gly Gly Gly Leu Val Lys
                20                 25                 30

Pro Gly Gly Ser Leu Lys Leu Ser Cys Ala Val Ser Gly Phe Thr Phe
                35                 40                 45

Lys Thr Tyr Ile Met Ser Trp Val Arg Gln Ser Pro Glu Lys Arg Leu
    50                 55                 60

Glu Trp Val Ala Thr Ile Asn Ser Gly Gly Tyr Tyr Thr Ile Tyr Pro
65                 70                 75                 80

Asp Ser Val Lys Gly Arg Phe Thr Ile Ser Arg Asp Asn Ala Lys Asn
                85                 90                 95

Thr Leu Tyr Leu Gln Met Ser Ser Leu Arg Ser Glu Asp Thr Ala Met
                100                105                110

Tyr Tyr Cys Ala Arg Gln Glu Gly Trp Ser Ser Ala Trp Phe Ala Tyr
                115                120                125

Trp Gly Gln Gly Thr Leu Val Thr Val Ser Ala
                130                135

<210> SEQ ID NO 49
<211> LENGTH: 127
<212> TYPE: PRT
<213> ORGANISM: Mus musculus
<220> FEATURE:
<221> NAME/KEY: SIGNAL
<222> LOCATION: (1)..(20)

<400> SEQUENCE: 49

Met Ser Val Leu Thr Gln Val Leu Ala Leu Leu Leu Leu Trp Leu Thr
1               5                  10                 15

Gly Ala Arg Cys Asp Ile Gln Met Ser Gln Ser Pro Ala Ser Leu Ser
                20                 25                 30

Ala Ser Val Gly Glu Thr Val Thr Ile Thr Cys Arg Ala Ser Gly Ser
                35                 40                 45

Ile His Asn Tyr Leu Ala Trp Tyr Gln Gln Lys Gln Gly Lys Ser Pro
    50                 55                 60

Gln Leu Leu Val Tyr Asn Ala Glu Thr Leu Ala Asp Gly Val Pro Ser
65                 70                 75                 80

Arg Phe Ser Gly Ser Gly Ser Gly Thr Gln Tyr Ser Leu Lys Ile Ser
                85                 90                 95

Ser Leu Gln Pro Glu Asp Phe Gly Thr Tyr Tyr Cys Gln His Phe Trp
                100                105                110

Ile Thr Pro Trp Thr Phe Gly Gly Gly Thr Lys Leu Glu Ile Lys
                115                120                125

<210> SEQ ID NO 50
<211> LENGTH: 141
<212> TYPE: PRT
<213> ORGANISM: Mus musculus
<220> FEATURE:
<221> NAME/KEY: SIGNAL
<222> LOCATION: (1)..(19)

<400> SEQUENCE: 50

Met Glu Cys Asn Trp Ile Leu Pro Phe Ile Leu Ser Val Thr Ser Gly
1               5                  10                 15

Val Tyr Ser Gln Val Gln Val Gln Gln Ser Gly Ala Glu Leu Ala Arg
                20                 25                 30

Pro Gly Ala Ser Val Lys Leu Ser Cys Lys Ala Ser Gly Tyr Thr Leu
                35                 40                 45
```

```
Thr Arg Tyr Trp Met Gln Trp Val Lys Gln Arg Pro Gly Gln Gly Leu
    50                  55                  60

Glu Trp Ile Gly Ala Ile Tyr Pro Arg Asp Gly Asp Thr Arg Tyr Ser
65                  70                  75                  80

Gln Lys Phe Lys Gly Lys Ala Thr Leu Thr Ala Asp Lys Ser Ser Thr
                85                  90                  95

Thr Ala Tyr Met Gln Leu Ser Ser Leu Ala Ser Glu Asp Ser Ala Val
            100                 105                 110

Tyr Tyr Cys Ala Tyr Pro Asp Gly Ser Tyr Ala Ala Pro Asn Gly Met
        115                 120                 125

Glu Tyr Trp Gly Gln Gly Ser Ser Val Thr Val Ser Ser
    130                 135                 140

<210> SEQ ID NO 51
<211> LENGTH: 5
<212> TYPE: PRT
<213> ORGANISM: Mus musculus

<400> SEQUENCE: 51

Arg Tyr Trp Met Gln
1               5

<210> SEQ ID NO 52
<211> LENGTH: 17
<212> TYPE: PRT
<213> ORGANISM: Mus musculus

<400> SEQUENCE: 52

Ala Ile Tyr Pro Gly Asp Gly Asp Thr Arg Tyr Ser Gln Lys Phe Lys
1               5                   10                  15

Gly

<210> SEQ ID NO 53
<211> LENGTH: 13
<212> TYPE: PRT
<213> ORGANISM: Mus musculus

<400> SEQUENCE: 53

Pro Asp Gly Tyr Tyr Ala Ala Pro Tyr Gly Met Asp Tyr
1               5                   10

<210> SEQ ID NO 54
<211> LENGTH: 11
<212> TYPE: PRT
<213> ORGANISM: Mus musculus

<400> SEQUENCE: 54

Arg Ala Ser Gly Asn Ile His Asn Tyr Leu Ala
1               5                   10

<210> SEQ ID NO 55
<211> LENGTH: 7
<212> TYPE: PRT
<213> ORGANISM: Mus musculus

<400> SEQUENCE: 55

Asn Ala Lys Thr Leu Ala Asp
1               5

<210> SEQ ID NO 56
<211> LENGTH: 9
<212> TYPE: PRT
```

<213> ORGANISM: Mus musculus

<400> SEQUENCE: 56

Gln His Phe Trp Ser Thr Pro Trp Thr
1               5

<210> SEQ ID NO 57
<211> LENGTH: 17
<212> TYPE: PRT
<213> ORGANISM: Mus musculus

<400> SEQUENCE: 57

Thr Ile Tyr Pro Gly Asp Gly Asp Thr Arg Tyr Ser Gln Lys Phe Lys
1               5                   10                  15
Gly

<210> SEQ ID NO 58
<211> LENGTH: 17
<212> TYPE: PRT
<213> ORGANISM: Mus musculus

<400> SEQUENCE: 58

Ala Ile Tyr Pro Arg Asp Gly Asp Thr Arg Tyr Ser Gln Lys Phe Lys
1               5                   10                  15
Gly

<210> SEQ ID NO 59
<211> LENGTH: 13
<212> TYPE: PRT
<213> ORGANISM: Mus musculus

<400> SEQUENCE: 59

Pro Asp Gly Ser Tyr Ala Ala Pro Asn Gly Met Glu Tyr
1               5                   10

<210> SEQ ID NO 60
<211> LENGTH: 11
<212> TYPE: PRT
<213> ORGANISM: Mus musculus

<400> SEQUENCE: 60

Arg Ala Ser Gly Ser Ile His Asn Tyr Leu Ala
1               5                   10

<210> SEQ ID NO 61
<211> LENGTH: 7
<212> TYPE: PRT
<213> ORGANISM: Mus musculus

<400> SEQUENCE: 61

Asn Ala Glu Thr Leu Ala Asp
1               5

<210> SEQ ID NO 62
<211> LENGTH: 9
<212> TYPE: PRT
<213> ORGANISM: Mus musculus

<400> SEQUENCE: 62

Gln His Phe Trp Ile Thr Pro Trp Thr
1               5

<210> SEQ ID NO 63
<211> LENGTH: 5

```
<212> TYPE: PRT
<213> ORGANISM: Mus musculus

<400> SEQUENCE: 63

Thr Phe Ile Met Ser
1               5

<210> SEQ ID NO 64
<211> LENGTH: 17
<212> TYPE: PRT
<213> ORGANISM: Mus musculus

<400> SEQUENCE: 64

Thr Ile Asn Ser Gly Gly Tyr Tyr Thr Phe His Pro Asp Ser Val Lys
1               5                   10                  15

Gly

<210> SEQ ID NO 65
<211> LENGTH: 11
<212> TYPE: PRT
<213> ORGANISM: Mus musculus

<400> SEQUENCE: 65

Gln Glu Gly Trp Ser Ser Ala Tyr Phe Ser Tyr
1               5                   10

<210> SEQ ID NO 66
<211> LENGTH: 17
<212> TYPE: PRT
<213> ORGANISM: Mus musculus

<400> SEQUENCE: 66

Lys Ser Ser Gln Ser Leu Leu Asn Gly Ser Asn Gln Lys Asn Tyr Leu
1               5                   10                  15

Ala

<210> SEQ ID NO 67
<211> LENGTH: 7
<212> TYPE: PRT
<213> ORGANISM: Mus musculus

<400> SEQUENCE: 67

Phe Ala Ser Thr Arg Asp Ser
1               5

<210> SEQ ID NO 68
<211> LENGTH: 9
<212> TYPE: PRT
<213> ORGANISM: Mus musculus

<400> SEQUENCE: 68

Gln Gln His Tyr Asp Thr Pro Tyr Thr
1               5

<210> SEQ ID NO 69
<211> LENGTH: 5
<212> TYPE: PRT
<213> ORGANISM: Mus musculus

<400> SEQUENCE: 69

Thr Tyr Ile Met Ser
1               5

<210> SEQ ID NO 70
```

```
<211> LENGTH: 17
<212> TYPE: PRT
<213> ORGANISM: Mus musculus

<400> SEQUENCE: 70

Thr Ile Asn Ser Gly Gly Tyr Tyr Thr Leu Tyr Pro Asp Ser Val Lys
1               5                   10                  15

Gly

<210> SEQ ID NO 71
<211> LENGTH: 11
<212> TYPE: PRT
<213> ORGANISM: Mus musculus

<400> SEQUENCE: 71

Gln Glu Gly Trp Ser Ser Ala Trp Phe Ala Tyr
1               5                   10

<210> SEQ ID NO 72
<211> LENGTH: 17
<212> TYPE: PRT
<213> ORGANISM: Mus musculus

<400> SEQUENCE: 72

Asn Ser Ser Gln Ser Leu Leu Asn Ser Asn Gln Lys Asn Tyr Leu
1               5                   10                  15

Ala

<210> SEQ ID NO 73
<211> LENGTH: 7
<212> TYPE: PRT
<213> ORGANISM: Mus musculus

<400> SEQUENCE: 73

Phe Ala Ser Thr Gly Glu Ser
1               5

<210> SEQ ID NO 74
<211> LENGTH: 9
<212> TYPE: PRT
<213> ORGANISM: Mus musculus

<400> SEQUENCE: 74

Gln Gln His Phe Ser Thr Pro Tyr Thr
1               5

<210> SEQ ID NO 75
<211> LENGTH: 5
<212> TYPE: PRT
<213> ORGANISM: Mus musculus

<400> SEQUENCE: 75

Ser Phe Val Met Ser
1               5

<210> SEQ ID NO 76
<211> LENGTH: 17
<212> TYPE: PRT
<213> ORGANISM: Mus musculus

<400> SEQUENCE: 76

Thr Ile Asn Ser Gly Gly Tyr Tyr Ser Phe His Pro Asp Ser Val Lys
1               5                   10                  15

Gly
```

<210> SEQ ID NO 77
<211> LENGTH: 17
<212> TYPE: PRT
<213> ORGANISM: Mus musculus

<400> SEQUENCE: 77

Lys Ser Ser Gln Ser Leu Leu Asn Ser Ser Asn Gln Lys Asn Tyr Leu
1               5                   10                  15

Ala

<210> SEQ ID NO 78
<211> LENGTH: 7
<212> TYPE: PRT
<213> ORGANISM: Mus musculus

<400> SEQUENCE: 78

Phe Thr Ser Thr Arg Glu Ser
1               5

<210> SEQ ID NO 79
<211> LENGTH: 17
<212> TYPE: PRT
<213> ORGANISM: Mus musculus

<400> SEQUENCE: 79

Thr Ile Asn Ser Gly Gly Tyr Tyr Thr Ile Tyr Pro Asp Ser Val Lys
1               5                   10                  15

Gly

<210> SEQ ID NO 80
<211> LENGTH: 5
<212> TYPE: PRT
<213> ORGANISM: Mus musculus

<400> SEQUENCE: 80

Thr Tyr Trp Ile Glu
1               5

<210> SEQ ID NO 81
<211> LENGTH: 17
<212> TYPE: PRT
<213> ORGANISM: Mus musculus

<400> SEQUENCE: 81

Glu Ile Leu Pro Gly Arg Gly Thr Thr Asn Tyr Asn Ala Lys Phe Gln
1               5                   10                  15

Gly

<210> SEQ ID NO 82
<211> LENGTH: 9
<212> TYPE: PRT
<213> ORGANISM: Mus musculus

<400> SEQUENCE: 82

Glu Ser Lys Leu Gly Asp Asp Asp Tyr
1               5

<210> SEQ ID NO 83
<211> LENGTH: 10
<212> TYPE: PRT
<213> ORGANISM: Mus musculus

<400> SEQUENCE: 83

Ser Ala Ser Ser Val Ser Tyr Met His
1               5                  10

<210> SEQ ID NO 84
<211> LENGTH: 7
<212> TYPE: PRT
<213> ORGANISM: Mus musculus

<400> SEQUENCE: 84

Asp Thr Thr Lys Leu Ala Ser
1               5

<210> SEQ ID NO 85
<211> LENGTH: 9
<212> TYPE: PRT
<213> ORGANISM: Mus musculus

<400> SEQUENCE: 85

Phe Gln Gly Ser Glu His Pro Leu Thr
1               5

<210> SEQ ID NO 86
<211> LENGTH: 106
<212> TYPE: PRT
<213> ORGANISM: Mus musculus

<400> SEQUENCE: 86

Glu Asn Val Leu Thr Gln Ser Pro Ala Ile Met Ser Ala Ser Pro Gly
1               5                   10                  15

Glu Arg Val Thr Met Thr Cys Ser Ala Ser Ser Val Ser Tyr Met
            20                  25                  30

His Trp Tyr Gln Gln Lys Ser Ser Asn Ser Pro Lys Leu Trp Ile Tyr
            35                  40                  45

Asp Thr Thr Lys Leu Ala Ser Gly Val Pro Gly Arg Phe Ser Gly Ser
        50                  55                  60

Gly Ser Gly Asn Ser Tyr Ser Leu Thr Ile Ser Ser Met Glu Ala Glu
65                  70                  75                  80

Asp Val Ala Thr Tyr Phe Cys Phe Gln Gly Ser Glu His Pro Leu Thr
                85                  90                  95

Phe Gly Gly Gly Thr Thr Leu Glu Ile Lys
            100                 105

<210> SEQ ID NO 87
<211> LENGTH: 120
<212> TYPE: PRT
<213> ORGANISM: Mus musculus

<400> SEQUENCE: 87

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Thr Phe
            20                  25                  30

Ile Met Ser Trp Val Arg Gln Ser Pro Glu Lys Arg Leu Glu Trp Val
            35                  40                  45

Ala Thr Ile Asn Ser Gly Gly Tyr Tyr Thr Phe His Pro Asp Ser Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Ile Tyr Tyr Cys
                85                  90                  95

```
Ala Arg Gln Glu Gly Trp Ser Ser Ala Tyr Phe Ser Tyr Trp Gly Gln
            100                 105                 110

Gly Thr Leu Val Thr Val Ser Ala
        115                 120

<210> SEQ ID NO 88
<211> LENGTH: 118
<212> TYPE: PRT
<213> ORGANISM: Mus musculus

<400> SEQUENCE: 88

Gln Val Gln Leu Gln Gln Ser Gly Pro Glu Leu Met Lys Pro Gly Ala
1               5                   10                  15

Ser Val Lys Ile Ser Cys Lys Ala Thr Gly Tyr Thr Phe Ser Thr Tyr
            20                  25                  30

Trp Ile Glu Trp Ile Lys Gln Arg Pro Gly His Gly Leu Glu Trp Ile
        35                  40                  45

Gly Glu Ile Leu Pro Gly Arg Gly Thr Thr Asn Tyr Asn Ala Lys Phe
    50                  55                  60

Gln Gly Lys Ala Thr Phe Thr Ala Glu Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Thr Thr Glu Ser Lys Leu Gly Asp Asp Asp Tyr Trp Gly Gln Gly Thr
            100                 105                 110

Thr Leu Thr Val Ser Ser
        115

<210> SEQ ID NO 89
<211> LENGTH: 101
<212> TYPE: PRT
<213> ORGANISM: Mus musculus
<220> FEATURE:
<221> NAME/KEY: misc_feature
<222> LOCATION: (64)..(64)
<223> OTHER INFORMATION: Xaa can be any naturally occurring amino acid

<400> SEQUENCE: 89

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Ser Ser
            20                  25                  30

Ser Asn Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Glu Ser Gly Xaa
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Leu Tyr Tyr Cys Gln Gln
                85                  90                  95

His Tyr Ser Thr Pro
            100

<210> SEQ ID NO 90
<211> LENGTH: 98
<212> TYPE: PRT
<213> ORGANISM: Mus musculus

<400> SEQUENCE: 90
```

-continued

| | | | | | | | | | | | | |
|---|---|---|---|---|---|---|---|---|---|---|---|---|
| Glu | Val | Lys | Leu | Val | Glu | Ser | Gly | Gly | Leu | Val | Lys | Pro | Gly | Gly |
| 1 | | | | 5 | | | | | 10 | | | | 15 | |
| Ser | Leu | Lys | Leu | Ser | Cys | Ala | Ala | Ser | Gly | Phe | Thr | Phe | Ser | Ser | Tyr |
| | | | 20 | | | | | 25 | | | | | 30 | | |
| Thr | Met | Ser | Trp | Val | Arg | Gln | Ser | Pro | Glu | Lys | Arg | Leu | Glu | Trp | Val |
| | | 35 | | | | | 40 | | | | | 45 | | | |
| Ala | Thr | Ile | Ser | Ser | Gly | Gly | Ser | Tyr | Thr | Tyr | Tyr | Pro | Asp | Ser | Val |
| | 50 | | | | 55 | | | | | 60 | | | | | |
| Lys | Gly | Arg | Phe | Thr | Ile | Ser | Arg | Asp | Asn | Ala | Lys | Asn | Thr | Leu | Tyr |
| 65 | | | | | 70 | | | | | 75 | | | | | 80 |
| Leu | Gln | Met | Ser | Ser | Leu | Lys | Ser | Glu | Asp | Thr | Ala | Met | Tyr | Tyr | Cys |
| | | | | 85 | | | | | 90 | | | | | 95 | |
| Thr | Arg | | | | | | | | | | | | | | |